United States Patent [19]

Cone, Jr.

[11] Patent Number: 4,935,450

[45] Date of Patent: * Jun. 19, 1990

[54] CANCER THERAPY SYSTEM FOR EFFECTING ONCOLYSIS OF MALIGNANT NEOPLASMS

[75] Inventor: Clarence D. Cone, Jr., Yorktown, Va.

[73] Assignee: Therapeutical Systems Corporation, Yorktown, Va.

[*] Notice: The portion of the term of this patent subsequent to Feb. 9, 2005 has been disclaimed.

[21] Appl. No.: 234,036

[22] Filed: Aug. 22, 1988

Related U.S. Application Data

[63] Continuation-in-part of Ser. No. 130,563, Dec. 8, 1987, abandoned, and Ser. No. 130,290, Dec. 8, 1987, abandoned, which is a continuation of Ser. No. 792,257, Oct. 28, 1985, Pat. No. 4,724,234, which is a continuation of Ser. No. 419,324, Sep. 17, 1982, abandoned, said Ser. No. 130,563, is a continuation of Ser. No. 634,267, Jul. 25, 1984, Pat. No. 4,724,230, which is a continuation-in-part of Ser. No. 419,324.

[51] Int. Cl.$^5$ .................. A61K 31/045; A61K 31/20; A61K 31/195

[52] U.S. Cl. .................................... 514/728; 514/558; 514/561

[58] Field of Search ....................... 514/728, 558, 561

[56] References Cited

U.S. PATENT DOCUMENTS

| | | | |
|---|---|---|---|
| 4,724,230 | 2/1988 | Cone | 514/558 |
| 4,724,234 | 2/1988 | Cone | 514/728 |

OTHER PUBLICATIONS

White, A., et al., *Prin. of Biochem.*, 6th Ed., McGraw-Hill, New York (1978), p. 1269.
Meares, A., *The Lancet*, Nov. 7, 1981, pp. 1037-1038.
Meares, A., *Med. Journal of Aust.*, Oct. 21, 1978, p. 433.
Meares, A., *Med. J. of Aust.*, Nov. 17, 1979, pp. 539-540.
Meares, A., *Med. J. of Aust.*, Jul. 23, 1977, pp. 132-133.
Meares, A., *Med. J. of Aust.*, Jul. 31, 1976, p. 184.
Meares, A., *Aust. Family Physician*, vol. 9, May 1980, pp. 322-325.
Meares, A., *J. Am. Soc. Psycho., Dentist. and Med.*, vol. 27, No. 2 (1980), pp. 40-41.
Meares, A., *Med. J. of Aust.*, May 12, 1962, pp. 711-714.
Meares, A., *Aust. Family Physician*, vol. 10, Mar. 1981, pp. 218-219.
Meares, A., *The Practitioner*, vol. 222, Jan. 1979, pp. 119-122.
Simonton, O. et al., *J. Transpersonal Psychol.*, vol. 7 (1975), pp. 29-47.
LeShan, L., *Psychiat. Quarterly*, vol. 35, pp. 314-330.
G. Weber, "Biochemical Strategy of Cancer Cells and the Design of Chemotherapy: G.H.A. Clowes Memorial Lecture", *Cancer Research* 43:3466-3492 (Aug. 1983).
R. I. C. Wesdorp et al., "Cancer Cachexia and Its Nutritional Implications", *Br. J. Sur* 70(6):352-355 (Jun. 1983).
M. M. King et al., "Modulation of Tumor Incidence and Possible Mechanisms of Inhibition of Mammary Carcinogenesis by Dietary Antioxidents", *Cancer Research (Suppl.)* 43: 2485s-2490s (May 1983).
A. E. Rogers, "Influence of Dietary Content of Lipids and Lipotropic Nutrients on Chemical Carcinogenesis in Rats"; *Cancer Research (Suppl.)* 43: 2477s-2484S (May 1983).
S. Weinhouse, S., "Changing Perceptions of Carbohydrate Metabolism in Tumors", *Molecular Interrelations of Nutrition and Cancer*, edited by M. S. Arnott, et al., Raven Press, N.Y. (1982) pp. 167-181.
G. Weber, "Differential Carboxydrate Metabolism in Tumor and Hosts", *Molecular Interrelations of Nutrition*

(List continued on next page.)

*Primary Examiner*—John W. Rollins
*Attorney, Agent, or Firm*—Venable, Baetjer, Howard & Civiletti

[57] ABSTRACT

A method for effecting oncolysis, regression, and control of malignant neoplasms in humans and other mammals without adverse effects on normal body cells is described. An ATP-availability depressor may be combined with a defined nutritional regimen, a fatty acid blocker, an amino acid blocker, a lactate export blocker, or any combination thereof.

172 Claims, 4 Drawing Sheets

OTHER PUBLICATIONS

*and Cancer* edited by M. S. Arnott, Raven Press, New York (1982) pp. 191–208.

D. Kritchevsky, "Lipids and Cancer", *Molecular Interrelations of Nutrition and Cancer,* edited by M. S. Arnott et al., Raven Press, New York (1982) pp. 209–217.

W. R. Kidwell et al., "Effect of Unsaturated Fatty Acids on the Development and Proliferation of Normal and Neoplastic Breast Epithelium", *Molecular Interrelations of Nutrition and Cancer,* edited by M. S. Arnott et al., Raven Press, N.Y. (1982).

K. K. Carroll et al., "The Role of Lipids in Tumorigenesis", *Molecular Interrelations of Nutrition and Cancer,* edited by M. S. Arnott et al., Raven Press, New York (1982) pp. 237–245.

B. B. Lavietes et al., "The Role of Lipid Metabolism in Neoplastic Differentiation", *J. Theor. Biol.* 85:523–542 (1980).

M. S. Wicha et al., "Effects of Free Fatty Acids on the Growth of Normal and Neoplastic Rat Mammary Epithelial Cells", *Cancer Research* 39: 426–435 (Feb. 1979).

C. P. Burns et al., "Utilization of Long-Chain Free Fatty Acids and Glucose by Human Leukemic Blast Cells", *Cancer Research* 37:1323–1327 (May 1977).

M. L. Littman et al., "Effect of Cholesterol-Free, Fat-Free Diet and Hypocholesteremic Agents on Growth of Transplantable Animal Tumors", *Cancer Chemotherapy Reports* 50(1 and 2); 25–45 (1966).

A. Lehninger, "Oxidation of Fatty Acids in Animal Tissues", Chapter 18 (1982).

U. Olowe et al., *The Journal of Biological Chemistry* 257(10):5408–5413 (1982).

B. M. Raaka et al., *The Journal of Biological Chemistry* 254 (9): 3303–3310 (1979).

B. M. Raaka et al., *The Journal of Biological Chemistry* 254(14): 6755–6762 (1979).

J. C. Fong et al., "On the Rate-Determining Step of Fatty Acid Oxidation in Heart Inhibition of Fatty Acid Oxidation by 4-Pentenoic Acid", *The Journal of Biological Chemistry* 253(19); 6917–6922 (1978).

E. B. Feldman et al., "Circulating Lipids and Lipoproteins in Women with Metastaic Breast Carcinoma", *J. Clin. Encrinol. and Metab.* 33:8 (1971).

S. Weinhouse, "Metabolism and Isozyme Alterations in Experimental Hepatomas", Federation Proceedings 32(12): 2162–2167 (1973).

S. Kitada et al., "Characterization of a Lipid Mobilizing Factor from Tumors", *Golden Jubilee International Congress on Essential Fatty Acid and Prostaglandins,* edited by R. T. Holman et al., Pergamon Press, New York (1981).

L. Block-Frankethal et al., "Fatty Acid Oxidation and Ketogenesis in Transplantable Liver Tumors", *Cancer Research* 25(5): 732–36 (1965).

*Merck Index Tenth Ed.,* Merck & Co., Inc. Rahway, N.J. (1983) specific paragraph citations in main text, (pp. 26–27).

P. G. Heatler, *Inhibition of Mitochondrial Functions,* Pergamon (1981).

*Chemical Abstr.* 73:12786f, 1970.

*Chemical Abstr.* 73:18358h, 1970.

*Chemical Abstr.* 69:657371, 1968.

*Chemical Abstr.* 70:1785s, 1969.

H. Busch, *An Introduction to Biochem of Cancer Cell* Ch. 10, 10, Acad. Press, N.Y. 1962.

L. M. Demers et al., *Proc. Soc. Exper. Biol. M.* 140: 724, 1972.

H. C. Hemker, *BBA* 48:221, 1961.

*Haskell Cancer Treatment,* Saunder Co., Pa., 2nd ed. 1985, Chg. to 76, pp. 889–896.

C. P. Burns et al., "Fatty Acid Utilization by L1210 Murine Leukemia Cells", *Cancer Research* 37: 1991–1997 (Jul. 1977).

I. A. Cederbaum et al., "Fatty Acid Oxidation, Substrate Shuttles, and Activity of the Citric Acid Cycle in Hepatocellular Carcinomas of Varying Differentiation", *Cancer Research* 36: 2980–2987 (Sep. 1976).

A. A. Spector et al., "Fatty Acid Metabolism in Tumors", *Progr. Biochem Pharmacol.,* 10: 42–75 (Karger, Basel 1975).

J. R. Sabine, "Defective Control of Lipid Biosynthesis in Cancerous and Precancerous Liver", *Progr. Biochem Pharmacol.,* 10: 269–307 (Karger, Basel 1975).

K. K. Carroll, "Dietary Fat in Relation to Tumorigensis", *Prgr. Biochem. Pharmacol.,* 10:308–353 (Karger, Basel 1975).

J. van Eys, "Nutrition and Neoplasia", *Nutrition Reviews* 40(12); 353–359 (1982).

G. P. Buzby et al., "Host-Tumor Interaction and Nutrient Supply", *Cancer* 45(12):2940–2948 (1980).

Spencer et al., *Biochem J.* 154, 405–414 (1976).

Johnson et al., *Biochem* 19, 3836–3840 (1980).

Belt et al., *Biochem* 18, 3506–3511 (1979).

Smith et al., *Fed Proc* 38, 2150–2153 (1979).

Tutwiler et al., *Diabetes* 28, 242–248 (1979).

CANCER THERAPY SYSTEM FOR EFFECTING ONCOLYSIS OF MALIGNANT NEOPLASMS

CONTENTS

CROSS REFERENCE TO RELATED APPLICATIONS

BACKGROUND OF THE INVENTION
 Table I. Abbreviations and Symbols
BRIEF DESCRIPTION OF THE DRAWINGS DEFINITIONS
 Definitions of the Primary Metabolic Effectors
 Further Definitions
BRIEF DESCRIPTION OF THE INVENTION DETAILED DESCRIPTION OF THE INVENTION
 Actions of the Primary Metabolic Effectors
 Defined Nutritional Regimen (DNR)
 Fatty Acid Blocking Agents (FAB)
 Amino Acid Blocking agents (AAB)
 ATP-Availability Depressor Agents (AAD)
 Lactate Export Blocking Agents (LEB)
 Combinations of the Metabolic Effectors
 Most Preferred Embodiment
ILLUSTRATIVE THERAPY SYSTEM FOR HUMAN PATIENTS EXAMPLES OF CLINICAL EFFECTIVENESS OF METABOLIC EFFECTOR MALIGNANCY THERAPY ACCORDING TO THIS INVENTION (EXAMPLES)
CLAIMS

CROSS REFERENCE TO RELATED APPLICATIONS

This application is a continuation-in-part application of U.S. Ser. No. 130,290, filed Dec. 8, 1987, now abandoned, and U.S. Ser. No. 130,563, filed Dec. 8, 1987, now abandoned. U.S. Ser. No. 130,290 in turn is a continuation application of U.S. Ser. No. 792,257, filed Oct. 28, 1985, now U.S. Pat. No. 4,724,234, issued Feb. 9, 1988, which is a continuation application of U.S. Ser. No. 419,324, filed Sept. 17, 1982, now abandoned. U.S. Ser. No. 130,563 in turn is a continuation application of U.S. Ser. No. 634,267, filed July 25, 1984, now U.S. Pat. No. 4,724,230, issued Feb. 9, 1988, which is a continuation-in-part application of U.S. Ser. No. 419,324, filed Sept. 17, 1982, now abandoned.

Reference is made to Disclosure Document No. 164,585 filed by the present inventor on Feb. 20, 1987, which relates to the present invention. Permanent retention thereof is hereby requested.

BACKGROUND OF THE INVENTION

When the rate of availability of adenosine triphosphate ($\dot{A}TP_A$) for use in satisfying the overall metabolic reactions in a cell is depressed below the level that must be maintained just to satisfy those cellular energy needs for vital metabolic processes, the cell becomes incapable of mitotic division and ultimately dies. The rate of change in the ATP pool size existing in a cell at a particular time is the difference between the rate at which ATP is being produced, primarily by oxidative phosphorylation (O/P) along the Respiratory Chain (RC) in the mitochondria, and the rate at which ATP is being used up (hydrolyzed) to provide for all the energy requirements of the cell. This energy is principally required for all the myriad anabolic and catabolic reactions in the metabolism of the cell, including powering of the "sodium pumps" of the pericellular membrane—whose collective action keeps the intracellular $Na^+$-concentration relatively low despite the continuous leakage of $Na^+$ through the membrane into the cell from the high $Na^+$-concentration extracellular fluid. The fundamental pathway involved in ATP production and usage (hydrolysis) in all normal body cells is depicted in FIG. 1.

The abbreviations and symbols used in FIG. 1 and elsewhere throughout this application are explained in the following table. Definitions of the primary therapeutical factors, the metabolic effectors Defined Nutritional Regimen (DNR), Fatty Acid Blocking Agent (FAB), Amino Acid Blocking Agent (AAB), ATP-Availability Depressor Agent (AAD) and Lactate Export Blocking Agent (LEB) of the present therapy system are given in the section entitled "Definitions of the Primary Metabolic Effectors," infra.

TABLE I

| Abbreviations and Symbols | |
|---|---|
| AA | amino acids |
| AAB | amino acid blocking agent |
| AAD | ATP-availability depressor agent |
| AcCoA | acetyl coenzyme A |
| ADP | adenosine diphosphate |
| ATP | adenosine triphosphate |
| [ATP] | intracellular ATP concentration |
| $\dot{A}TP$ | rate of production or degradation of ATP |
| ATPase | adenosine triphosphatase |
| $\dot{A}TP_A$ | rate of availability of ATP for use in cellular metabolism |
| $ATP_{EMP}$ | ATP produced in the EMP |
| $\dot{A}TP_{EMP}$ | rate of ATP production in the EMP |
| $ATP_G$ | ATP produced by glycolysis |
| $\dot{A}TP_G$ | rate of ATP production by glycolysis |
| $\dot{A}TP_L$ | lethal level of $\dot{A}TP_A$ |
| $\dot{A}TP_O$ | rate of ATP produced by O/P in RC |
| $\dot{A}TP_P$ | overall rate of production of ATP by cell |
| $\dot{A}TP_R$ | rate of utilization of ATP by cell |
| $\dot{A}TP_W$ | rate of wasting of ATP by AAD |
| $\Delta\dot{A}TP_G$ | change in $\dot{A}TP_G$ caused by AAD |
| $\Delta\dot{A}TP_O$ | change in $\dot{A}TP_O$ caused by AAD |
| $\bar{c}$ | "with" (cum) |
| Ca | calcium |
| CAC | Citric Acid Cycle |
| $\dot{C}AC$ | rate of operation of the CAC |
| $Cl^-$ | chlorine ion |

TABLE I-continued
Abbreviations and Symbols

| | |
|---|---|
| $CO_2$ | |
| RC | |
| CoA | coenzyme A |
| cm | centimeter |
| CPK | creatine phosphokinase |
| d | day |
| DFA | DNR + FAB + AAB combination |
| dl | deciliter (100 ml) |
| DNP | 2,4-Dinitrophenol |
| DNR | defined nutritional regimen |
| EMP | Embden-Meyerhof Pathway |
| FA | fatty acids |
| FAB | fatty acid blocking agent |
| g | gram |
| GLY | rate of operation of the Glycolytic (or EMP) Pathway |
| $\Delta$GLY | change GLY caused by AAD |
| H | hydrogen (atomic) |
| hr | hour |
| I | Iodine |
| i | initial value of a quantity (subscript) |
| I.U. | international unit |
| KCl | potassium chloride |
| Kg | kilogram |
| LAC | lactic acid (lactate) |
| $LAC_P$ | rate of production of lactic acid in a cell |
| $LAC_E$ | rate of export of lactic acid from a cell |
| LEB | lactate export blocking agent |
| $lO_2/d$ | liters of $O_2$ consumed metabolically, per day (24 hours) |
| max | maximum |
| min | minute |
| Mg | magnesium |
| mg | milligram |
| ml | milliliter |
| Mn | manganese |
| $Na^+$ | sodium ion |
| NaCl | sodium chloride |
| NADH | reduced nicotinamide adenine dinucleotide |
| $\dot{N}ADH$ | rate of supply of NADH to the RC |
| $O_2$ | molecular oxygen |
| O/P | oxidative phosphorylation (in RC) |
| P | phosphorus |
| PFK | phosphofructokinase |
| pH | intracellular pH (acidity measure) |
| $pH_L$ | lethal level of intracellular pH |
| RC | Respiratory Chain |
| RC | rate of operation of the RC (amount of NADH oxidized per unit time) |
| Se | selenium |
| $T_3$ | triiodothyronine |
| $T_4$ | thyroxine |
| TH | thyroid hormone ($T_4$ and/or $T_3$) |
| UA | uncoupling agent of O/P |
| Zn | zinc |
| $\mu g$ | microgram |
| $\uparrow$ | increase (in a rate) |
| $\downarrow$ | decrease (in a rate) |
| RDA | recommended daily allowance |
| s | "without" (sine) |

In normal (i.e., non-malignant) body ce nutritional component is glucose, from which the primary energy supply for synthesizing ATP is derived. Glucose is transformed by the sequential reactions of the Glycolytic or Embden-Meyerhof Pathway (EMP) into pyruvate. Only about 6% of the total energy available in the original glucose molecule is released in the form of ATP during degradation in the EMP. Subsequently, pyruvate is decarboxylated and forms acetyl coenzyme A (AcCoA) which then enters the Citric Acid Cycle (CAC) in the mitochondria. Here each acetate moiety, after first being incorporated into a molecule of citric acid, is broken down into $CO_2$ and H with H appearing, inter alia, in molecules of reduced nicotinamide adenine dinucleotide (NADH) which then contain a large fraction of the energy contained in the original glucose. This NADH subsequently is oxidized in the mitochondrial Respiratory Chain with the ultimate production of $H_2O$ by terminal reaction of the H with $O_2$. This $O_2$ is supplied by the normal vasculature. The energy obtained by the transport of electrons down the potential gradient of the RC, by a series of redox reactions, is used to produce the ATP of the cell. About 94% of the total energy available in the original glucose molecule is released in the form of ATP during degradation of the AcCoA in the CAC and oxidation of the associated NADH in the RC. Thus, in normal cells, the ATP-stored energy is obtained in the major proportion from nutritional glucose or from carbohydrates (i.e., starches and sugars) which yield glucose upon digestion. Some ATP-energy is obtained in normal cells from the oxidation, in the CAC and RC, of fatty acids and amino acids obtained from nutritional fats and proteins. When adequate glucose is available in the nutriment intake, however, the major ATP-energy needs of practically all normal cells are readily obtainable from glucose alone. The ATP produced in the EMP and RC enters the cellular "ATP Pool", from which it is continuously withdrawn at the net availability rate $\dot{ATP}_A$ to supply the energy needs of total cellular metabolism including energy to power the membrane sodium pumps which keep the intracellular $Na^+$-concentration adequately low by the out-pumping of $Na^+$.

This same general pattern of ATP generation and usage exists in malignant cells, but with one crucial difference (see FIG. 2). It has been extensively demonstrated that the malignant cells of practically all forms of malignant neoplasms possess a common, distinctive metabolic aberrancy, apparently manifested as an innate consequence of their transformation to the malignant state [Niemtzow, R. C. (Ed.), *Transmembrane Potentials and Characteristics of Immune and Tumor Cells* Chapter 9, CRC Press, Boca Raton, Fla., (1985)]. Under in vivo conditions, the malignant cells of essentially all forms of malignant neoplasms do not substantially convert pyruvate to AcCoA (see FIG. 2). The pyruvate instead is essentially quantitatively converted to lactate which is exported from the cell by an effective lactate transport system [Warburg, O., *Uber den Stoffwechsel der Tumoren*, Springer-Verlag, Berlin and New York (1926); Warburg, O., *The Metabolism of Tumors* Constable, London (1930); Burk, D., *Cold Spring Harbor Symposia Quant. Biol.* 7, 420 (1939); Busch, H., *An Introduction to the Biochemistry of the Cancer Cell*, Chapter 10, Academic Press, New York (1962); Racker et al., *Science* 209, 203 (1981); Spencer, T. L. et al., *Biochem. J.* 154, 405 (1976); Belt, J. A. et al., *Biochem.* 18 3506 (1979): Weinhouse, S., *Cancer Res.* 3, 269 (1955); Busch, H. et al., *Cancer Res.* 20 50 (1960); Busch, H., *Cancer Res.* 13 789 (1955); Busch, H. et al., *J. Biol. Chem.* 196, 717 (1952); Nyham, W. L. et al., *Cancer Res.* 16, 227 (1957); Cori, C. F. et al., *J. Biol. Chem.* 64, 11 (1925); Cori, C. G. et al., *J. Biol. Chem.* 65, 397 (1925); Warburg, O. et al., *Klin. Wochschr.* 5, 829 (1926); Muramatsu, M., *Gann.* 52, 135 (1961); Busch, H. et al., *Cancer Res.* 16, 175 (1956)]. The net consequence is that only a small fraction ( ~6%) of the chemical energy in the glucose molecule can be extracted and used by the cancer cell, compared to that available to the normal cell, where glucose is totally oxidized [White, A. et al., *Principles of Biochemistry*, 5th Ed., p. 441 (1973)]. Since nutritional glucose is by far the most prominent and important source of normal cellular ATP energy under normal conditions, this transformation aberrancy puts the malignant cells at a great disadvantage regarding the maximal rates at which they can generate ATP from glucose oxidation via the CAC and RC. This metabolic defect is potentially particularly restrictive for the malignant cells, which generally need an especially abundant availability rate of ATP to support the active anabolic metabolism associated with the frequent mitosis characteristic of these proliferative cells.

However, malignant cells in vivo quite effectively circumvent this energy deficiency under usual nutritional conditions by readily oxidizing fatty acids and amino acids in the CAC and RC [Busch, H. (1962) supra: Medes, G. et al., *Cancer Res.* 17 127 (1957); Allen, A. et al., *J. Biol. Chem.* 212, 921 (1955); Emmelot, C. et al., *Experientia* 11, 353 (1955); Weinhouse, S. et al., *Cancer Res.* 13, 367 (1953); Weinhouse, S. et al., *Cancer Res.* 11, 845 (1951); Kitada, S. et al., *Lipids* 15 168 (1980); Spector, A. A., *J. Biol. Chem.* 240, 1032 (1965)]. Mitochondria possess a very efficient enzyme system capable of effecting the "$\beta$-oxidation" of fatty acids directly to AcCoA, which then enters the Citric Acid Cycle and is oxidized exactly as AcCoA produced from oxidation of glucose in normal cells. The amino acids are, after initial deamination, similarly reduced to AcCoA or other intermediates of the CAC and then oxidized. Thus, some amino acids, after deamination and suitable transformation, which is readily accomplished by the enzyme systems of malignant cells, are capable of entering the Citric Acid Cycle directly at various intermediate points of the cycle [Busch, H. (1962), supra]. Consequently, although substantially deprived of the utilization of glucose as a primary energy source, the malignant cells make full use of the supply of the energy-rich fatty acids, and amino acids, all present in the plasma under usual nutritional intake levels.

Under conditions where the rate of production of ATP by oxidative catabolism of free fatty acids (FA) and amino acids (AA) via the CAC-RC is inhibited in cancer cells (e.g., because of a limited rate of substrate and/or oxygen supply, or presence of an O/P uncoupling agent), or the oxidatively derived ATP-availability rate is otherwise depressed (e.g., by inappropriately stimulated ATPase activity), the cells are able to compensate in part for this energy rate loss by strongly increasing the rate of glycolysis (GLY) per se. This increased GLY results in a pronounced rise in the rate of production of lactic acid ($LAC_P$). The lactate must concomitantly be rapidly exported from the cell in order to prevent the intracellular pH from decreasing to a lethal level because of a buildup in the lactate concentration. Under usual physiological conditions, the lactate export rate ($LAC_E$) capacity of cancer cells is much more than adequate to prevent such an intracellular lactate buildup [e.g., Spencer, T. L. et al. (1976) supra: Belt, J. A. et al. (1979) supra]. Consequently, the cancer cells can operate at relatively high GLY levels when energy is relatively unavailable from oxidative pathways of the CAC and RC.

In accordance with the present invention, the net availability rate of ATP, $ATP_A$, for satisfying the overall metabolic requirements of malignant cells in the body is depressed to a level which is inadequate for the maintenance of the essential metabolic processes required for the continued viability of the cells, without substantially altering the normal $ATP_A$ level in normal cells of the body (see FIG. 3). The malignant cells are thus selectively subjected to a lethal energy deprivation, resulting in cellular death as a consequence of energy starvation. In addition, the present invention provides simultaneously and synergistically for the stimulation of the GLY in malignant cells to a maximum level while concomitantly effectively limiting the maximum $LAC_E$ capability of the cells by inhibition of the lactate export system. The malignant cells are thus selectively subjected to a second alternate lethal action in which cellular death occurs as a consequence of acidity buildup and the depression of the intracellular pH below the level permissible for continued viability.

The most preferred embodiment of the present invention consists of the concurrent administration of five primary metabolic effectors (AAD, LEB, DNR, FAB and AAB), with sites of action as depicted in FIG. 3. For purposes of present dicussion, these metabolic effectors are arbitrarily grouped into three regimens which are, for clarity of presentation, discussed in the order in which they individually act in the metabolic energy pathway of the cancer cells (FIG. 3). As is detailed subsequently, other regimens and combinations of these metabolic effectors, although not constituting the most preferred embodiment for clinical application, are still fully capable of effecting very significant oncolysis.

The first regimen of metabolic effectors (DNR, FAB, AAB) is designed to substantially limit the maximum rate at which NADH can be supplied ($\dot{NADH}$) to the RC of the cancer cells in the body, thus substantially limiting the maximum rate at which ATP can be made oxidatively (i.e., by the CAC-RC) by the cells, without limiting the rate of NADH supply ($\dot{NADH}$) in the normal cells of the body to any significant degree. The second regimen's metabolic effector (AAD) is designed to degrade a substantial portion of such ATP as is produced or is potentially producible by the cancer cells, thus making it unavailable for cellular metabolic requirements. The pronounced deficit in the overall $ATP_A$ imposed by the first and second parts of the therapy, relative to that necessary to supply just the minimal ATP rate requirements of the essential metabolic processes, ultimately reduces the ATP pool selectively in the cancer cells to a lethal level. The third regimen's metabolic effector (LEB) is designed to greatly inhibit the rate at which glycolytically produced lactate can be exported from the cancer cells. The strong $ATP_A$ deficiency imposed by regimen two (supra) causes a pronounced increase in the cellular GLY and consequent $LAC_p$, thus synergistically insuring, in combination with regimen three of the therapy system, an ultimately lethal lactate buildup, which acts by producing a lethal depression of the intracellular pH. The concurrent use of the combination of the three regimens of the present therapy system thus provides two separate, but synergistically related, modes of achieving the destruction of cancer cells in the body, either of which may be the ultimate cause of lethality in a given cancer cell under different physiological conditions.

The first regimen (see FIG. 3) comprises the administration of a defined nutritional regimen (DNR) which consists essentially of a dietary regimen designed to maximize the use of nutritional glucose-yielding carbohydrates as a source of ATP energy, and to minimize the availability of nutritional fatty acids and amino acids for use as a source of ATP energy (FIG. 3). It also comprises the concurrent use of one or more fatty acid blocking agents or "fatty acid blockers" (FAB) and amino acid blocking agents or "amino acid blockers" (AAB) to inhibit the availability of oxidatively obtained (i.e., CAC-RC) ATP-energy from endogenously derived (body depot or plasma) free fatty acids and amino acids for use by the cancer cells.

The second regimen (FIG. 3) comprises the concurrent administration of one or more ATP-availability depressor agents or "ATP-availability depressors" (AAD) which, at adequate levels, results in the lowering or depression to a lethal level in the cancer cells of the net rate of the ATP, $ATP_A$, actually available for satisfying cellular metabolic needs, by directly inhibiting the synthesis rate of ATP per se (e.g., by use of uncoupling agents of O/P) and/or inactivating or hydrolyzing ATP already synthesized (e.g., by use of ATPase-hydrolysis-activity enhancing agents). Administration of the AAD makes unavailable to the cancer cells a large fraction of the maximum potential cellular ATP production per unit time otherwise available, a maximum already severely limited by the reduced availability of NADH resulting from the restriction of energy availability from fatty acids and amino acids by the DNR, FAB and AAB of the first part, and results in cell death by energy starvation. Since the normal cells of the body can make full use of the abundant carbohydrate (glucose) supplied by the DNR for energy purposes, the only effect on the normal cells is an increase in $O_2$ consumption rate (i.e., in increased RC); the potential ATP loss in the normal cells due to the AAD is fully compensated by a higher rate of glucose-derived NADH oxidation (NADH) by the respiratory chain, while the rate of actual ATP production and availability $ATP_A$ remains unchanged at its normal level.

The third regimen (FIG. 3) comprises the administration of one or more lactate export blocking agents or "lactate export blockers" (LEB) which results in a substantial reduction of the maximum rate at which lactate can be exported from the glycolyzing cancer cells in the body. The LEB blocks a substantial portion of the normal maximal lactate export rate capacity of the cancer cells and allows the lactate to build up in the cells adequately to produce a lethal pH level.

Applicant has previously disclosed a related method of effecting oncolysis comprising the use of a defined nutritional regimen (DNR) in combination with one or more O/P uncoupling agents (UA) [U.S. Pat. No. 4,724,234]. That therapy system may be considered as a special, restricted case of the present invention consisting of use of only a DNR and an AAD, wherein the AAD is specifically an uncoupling agent of cellular oxidative phosphorylation. Applicant has also previously disclosed [U.S. Pat. No. 4,724,230] a method for effecting oncolysis consisting of a combination of a DNR and one or more UA, and the concomitant use of fatty acid oxidation inhibiting agents ("FAOI" therein) which result in the inhibition of oxidation in cellular mitochondria of free fatty acids. That system may likewise be considered as a special, restricted case of the present invention, consisting of a DNR, FAB, and AAD, wherein the FAB is specifically an inhibitor of mitochondrial free fatty acid oxidation (FAOI) and the AAD is specifically an oxidative phosphorylation uncoupling agent (UA).

The potentiality of destroying cancer cells in vitro by depressing their intracellular pH to a lethal level by use of substances which inhibit lactate export has been previously addressed, based on in vitro experiments with cancer cell cultures [Johnson, J. H. et al. *Biochemistry* 19 3836 (1980)]. However, no clinical method of effecting oncolysis utilizing lactate inhibiting agents has heretofore been advanced. Ostensibly, this is because of the in vitro finding that cancer cells have an enormous reserve capacity for lactate export, relative to the usual rate of $GLY$ ($LAC_P$) at which they operate. Consequently, the lactate export capability must be almost totally blocked before any lactate buildup and pH decrease occurs [Spencer, T. L. et al. (1976), supra: Belt, J. A. et al. (1979), supra]. Such a high level of blockage would be most difficult to achieve and maintain in vivo. Moreover, it is known that the GLY level decreases significantly as the intracellular pH decreases [Wilhelm, G. et al. *FEBS Lett.* 17, 158 (1971), Belt, J. A. et al. (1979) supra; Suolinna, E.-M. et al., *Cancer Res.* 35, 1865 (1975)], thus making the required degree of blockage essentially total. Without such 100% blockage, the $LAC_p$ and hence the pH decline becomes self-limiting, and it is not possible generally to effect cancer cell death, even in vitro, by use of lactate export inhibiting agents alone. The present invention effectively overcomes these basic problems, since the pronounced depression of the cancer cell $ATP_A$ effected by the combination of parts one (DNR-FAB-AAB) and two (AAD) of the present invention raises the GLY and $LAC_P$ and maintains them at levels several fold greater than that normally existing (i.e., without such therapeutically imposed GLY stimulation) in cancer cells. Consequently, the high $LAC_p$ thereby effected not only ensures the maintenance of a high $LAC_p$ against the depressing tendency of a decreasing intracellular pH, but also thereby reduces substantially the degree of lactate export inhibition which must be effected in order to permit cellular lactate buildup and the intracellular pH to decrease to a lethal level. The present invention thus makes the use of lactate export blocking agents clinically practical and most efficacious.

Applicant has found in evaluative clinical treatment regimens administered according to the present invention utilizing far advanced human cancer patients having histologically verified malignancies representing a wide range of malignancy types (tongue, throat, stomach, cecum, colon, rectum, breast, ovary, uterus, lung, kidney, prostate, pancreas, lymphoma, melanoma, skin, marrow (leukemia), and bone) that very significant oncolysis is effected. These efficacious results were obtained with patients whose disease was found to be uncontrollable with conventional mitoxin chemotherapy and radiotherapy modalities. Throughout the treatment period of the individual patients, the clinical regimen was generally found to be free of discernable toxic side effects, and allowed a very high quality of life, despite the poor entry condition of most of the patients.

The therapy system of the present invention substantially avoids several of the traditional problems and limitations of conventional mitoxin chemotherapy. Mitoxin chemotherapy characteristically acts by the indiscriminate destruction of all mitotically active cells in the body, both normal and malignant. Because of this mass indiscriminate destruction of normal proliferative cells by mitoxin chemotherapy, a host of toxic and treatment-limiting side-effects are experienced, including anemia (marrow destruction), pronounced loss of cellular and humoral immune competence, decrease of blood platelets, gastrointestinal ulceration and denudation with bleeding, vomiting and diarrhea, destruction of salivary gland function, electrolyte imbalance, anorexia, loss of hair, abnormalities of the nervous system, kidney damage, skin rash, liver damage, abnormal heart beat, myocardial toxicity, and damage to the lungs. The present method of metabolic chemotherapy, because it does not adversely affect normal dividing cells in the body, is strikingly free of such toxic effects and therefore permits continued administration until potentially all malignant cells are destroyed, while simultaneously permitting a very high quality of life.

Similarly, since the present method does not destroy blastogenic lymphocytes of the immune system as does mitoxin chemotherapy, the body's immune competence remains unaltered, thus avoiding the pronounced decrease in resistance to infectious diseases usually seen in human patients undergoing mitoxin chemotherapy while maximally enhancing potential immunological cell-mediated and humoral attack on residual tumor cells.

DEFINITIONS

Definitions of the Primary Metabolic Effectors

Figure 1:
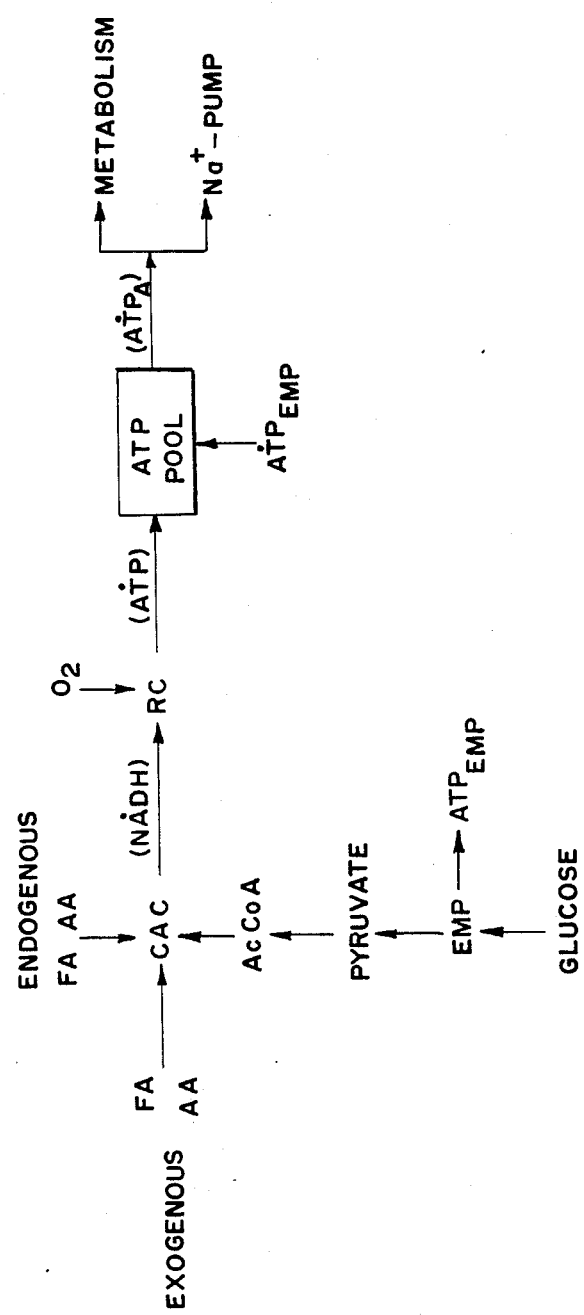
FIG. 1 is a flow diagram depicting the energy pathway for ATP production and usage in normal cells. The (·) over an abbreviation for a quantity denotes the time rate of the quantity, for example, NȦDH denotes the production rate of NADH.

In order to provide a clear and consistent understanding of the terms used in the specification and claims hereof, including the scope given to such terms, the following definitions are provided:

ATP Availability Depressor Agent (AAD): Any clinically tolerable substance, means or procedure whose administration acts directly or indirectly to wastefully prevent energy transfer via oxidative phosphorylation in the RC, or to wastefully hydrolyze ATP already synthesized by the cell or to otherwise make unavailable for cellular metabolic use energy from ATP synthesized by the cell.

Lactate Export Blocking Agent (LEB): Any clinically tolerable substance, means or procedure whose administration results either directly or indirectly in a decrease in the maximum rate at which lactic acid can be exported out of malignantly transformed cells.

Defined Nutritional Regimen (DNR): Any nutritional regimen, oral and/or parenteral, which provides substantially all the daily caloric intake from sources of glucose, is substantially free of fatty acid sources other than of the essential linoleic and linolenic fatty acids, and provides only the minimal amount of protein sources of amino acids required to maintain body nitrogen balance.

Fatty Acid Blocking Agent (FAB): Any clinically tolerable substance, means or procedure whose administration results either directly or indirectly in a decrease in the production rate of ATP energy derived from the overall metabolic oxidative degradation of fatty acids.

Amino Acid Blocking Agent (AAB): Any clinically tolerable substance, means or procedure whose administration results either directly or indirectly in a decrease in the production rate of ATP energy derived from the overall metabolic oxidative degradation of amino acids.

Further Definitions

1. Agent: as used herein, refers to a substance, means or procedure for effecting a particular metabolic result.

2. ATP Hydrolysis: as used herein, refers to the catalyzed breaking down of ATP into adenosine diphosphate and inorganic phosphate, or into adenosine monophosphate and pyrophosphate.

3. ATP Hydrolyzer: as used herein, refers to an agent capable of effecting ATP hydrolysis.

4. ATP Wasting: as used herein, refers to an imposed reduction in the rate of availability of ATP for cellular metabolism achieved by a decrease in the rate of production of ATP by wastefully uncoupling oxidation and phosphorylation in the RC, or by wastefully hydrolyzing ATP already made by the cells, or by wastefully preventing already-made ATP from taking part in cellular metabolic reactions.

5. Cancer Cell: as used herein, refers to any malignantly transformed cellular phenotype deriving from a medical malignancy.

6. Malignancy: as used herein, refers to any of the pathological neoplastic disease states medically classified by histological analysis as carcinoma, sarcoma, lymphoma, or leukemia.

7. Mammal: as used herein, refers to any of the class Mammalia of higher vertebrates comprising humans and all other animals that nourish their young with milk secreted by mammary glands.

8. Metabolism: as used herein, refers to the totality of biochemical reactions and processes ongoing in a cell incidental in the support of viability and life.

9. Neoplasm: as used herein, refers to a new growth of tissue serving no physiologic function; a tumor.

10. Oncolysis: as used herein, refers to the elimination, reduction or control of malignant neoplasms by effecting the death and/or proliferation-arrest of the malignant cells therein and thereof.

11. Oxidative Metabolism: as used herein, refers to a hierarchy of cellular biochemical reactions by which energy for ATP synthesis is obtained by degradation of glucose, fatty acids and amino acids, especially in the Citric Acid Cycle and associated Respiratory Chain of mitochondria.

12. Peg: as used herein, refers to the maximum level of a rate above which the rate cannot increase or be increased.

13. Primary Metabolic Effector: as used herein, refers to an agent capable, upon administration, of detrimentally altering the usual metabolism of a cancer cell by retarding substrate availability to a pathway, decreasing ATP availability, and/or inhibiting membrane transport functions; herein they include the ATP-availability depressor agents, lactate export blocking agents, defined nutritional regimen, fatty acid blocking agents and amino acid blocking agents.

14. Regimen: as used herein, refers to a systematic course or plan of treatment directed toward effecting oncolysis; such plan embraces diet, drugs, metabolic effectors and/or therapeutic procedures.

BRIEF DESCRIPTION OF THE INVENTION

The present invention affords a novel method of substantially eliminating, reducing or controlling (collectively referred to in this disclosure as oncolysis) a wide variety of malignant neoplasms in humans and other mammals. The effect on the malignancy (i.e., carcinoma, sarcoma, lymphoma, leukemia) is oncolysis, and is the result of the death and/or proliferation-arrest of malignant cells therein and thereof.

Figure 3:
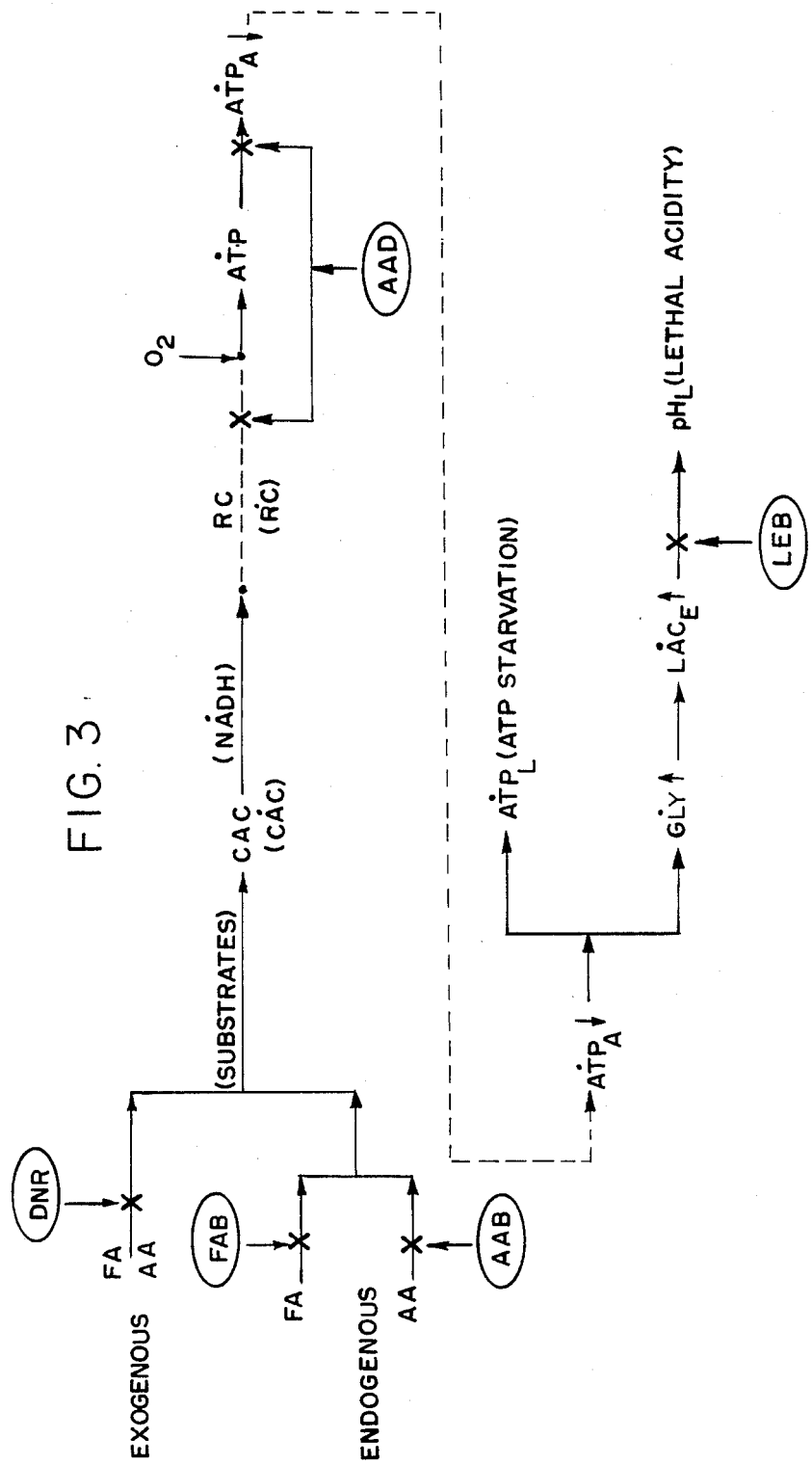
FIG. 3 is a flow diagram depicting the integrated regulatory system of interacting metabolic effectors utilized to produce death in malignantly transformed cells in the body by the method of the present invention.

In accordance with the present invention, the net availability rate of ATP ($ATP_A$) for satisfying the overall metabolic requirements of malignant cells in the body is depressed to a level which is inadequate for the maintenance of the essential metabolic processes required for the continued viability of the cells, without substantially altering the normal $ATP_A$ level in the normal cells of the body (see FIG. 3). The malignant cells are thus selectively subjected to a lethal ATP-energy deprivation, resulting in cellular death as a consequence of energy starvation. In addition, the present invention provides in its preferred embodiments simultaneously and synergistically for the stimulation of the GLY in malignant cells to a maximum level while concomitantly effectively limiting the maximum $LAC_E$ capability of these cells by inhibition of the lactate export system. The malignant cells are thus selectively subjected to a second lethal action in which cellular death occurs as a consequence of acidity buildup and the depression of the intracellular pH below the level permissible for continued viability.

In the present invention, the oncolysis of malignant neoplasms is effected by administration of an ATP-availability depressor agent (AAD), or a combination of an AAD and one or more additional metabolic effectors. Each such combination contains an effective amount of ATP-availability depressor agent (AAD). Other metabolic effectors which may be present in the combination include one or more of the following:

(1) an effective amount of a lactate export blocking agent (LEB) for limiting the rate at which lactic acid is exported from the malignant cells;

(2) an effective amount of a defined nutritional regimen (DNR) for limiting the amount of exogenously derived free fatty acids (FA) and amino acids (AA) available to the malignant cells, while providing calorically adequate glucose for metabolism in the normal cells of the body;

(3) an effective amount of a fatty acid blocking agent (FAB) for limiting the rate of availability of energy to the malignant cells from endogenously derived free fatty acids; and (4) an effective amount of an amino acid blocking agent (AAB) for limiting the rate of availability of energy to the malignant cells from endogenously derived amino acids.

The present invention comprises either (1) administering an AAD solely, or (2) concurrently administering an AAD and at least one other metabolic effector from among the LEB, DNR, FAB and AAB. See FIG. 3 for reference to the sites of action of these metabolic effectors in the energy metabolism pathway of the cancer cells. The AAD is designed to degrade a substantial portion of the ATP that is produced or is potentially producible by the cancer cells, thus making it unavailable for supporting cellular metabolic requirements. The AAD may comprise one or more agents which result, in adequate amount, in the lowering or depression to a lethal level in the cancer cells of the net rate at which ATP ($ATP_A$) is actually available for satisfying cellular metabolic needs, by directly inhibiting the synthesis rate of ATP per se (e.g., by use of uncoupling agents of O/P) and/or inactivating or hydrolyzing ATP already synthesized (e.g., by use of ATPase hydrolysis-activity enhancing agents).

The additional primary metabolic effectors (LEB, DNR, FAB, AAB) which can be used in combination with the AAD are designed to enhance the basic effects of the AAD per se and to further enhance the destruction of the malignant cells. One or more of the additional metabolic effectors can be used in combination with the AAD. These metabolic effectors include:

(1) one or more Lactate Export Blocking agents (LEB) for limiting the rate at which lactic acid is exported from malignant cells;

(2) a Defined Nutritional Regimen (DNR) which consists essentially of a dietary regimen designed to maximize the use of nutritional glucose-yielding carbohydrates as a source of ATP energy and to minimize the availability of nutritional fatty acids and amino acids for use as a source of ATP energy;

(3) one or more Fatty Acid Blocking agents (FAB) for limiting the rate of availability of energy to the malignant cells from endogenously derived free fatty acids; and (4) one or more Amino Acid Blocking agents (AAB) for limiting the rate of availability of energy to the malignant cells from endogenously derived amino acids.

In the present invention, it is preferred to use an AAD in combination with an LEB. It is most preferred to use all five components, i.e., AAD, LEB, DNR, FAB and AAB, in concurrently administered combination.

The efficacy of the method of this invention and the absence of toxic or untoward side effects have been demonstrated clinically with far advanced, previously judged "terminally ill" human cancer patients. Patients with histologically diagnosed malignancies representing a wide variety of malignant neoplasia types, including all malignancy types of major clinical frequency, have all responded clinically to the therapy system of the present invention. Because of the substantial absence of any toxic or debilitating side effects, the method has great promise for effectively treating many malignancies that are substantially uncontrollable by currently practiced treatment methods.

DETAILED DESCRIPTION OF THE INVENTION

In accordance with the therapy system of the present invention, the net availability rate of ATP ($ATP_A$) for satisfying the overall metabolic requirements of malignant cells in the body is depressed to a level which is inadequate for the maintenance of the essential metabolic processes required for the continued viability of the cells, without substantially altering the normal $ATP_A$ level in normal cells of the body (see FIG. 3). The malignant cells are thus selectively subjected to a lethal energy deprivation, resulting in cellular death as a consequence of energy starvation. In addition, the present invention in its most preferred embodiment provides simultaneously and synergistically for the stimulation of the GLY in malignant cells to a maximum level while concomitantly effectively limiting the maximum $LAC_E$ capability of the cells by inhibition of the lactate export system. The malignant cells are thus selectively subjected to a second alternate lethal action in which cellular death occurs as a consequence of acidity buildup and the depression of the intracellular pH below the level permissible for continued viability. At adequate levels of $ATP_A$ depression, but above those required for effecting cancer cell death, the present invention results in the arrest of mitotic activity because of energy insufficiency, and hence in the arrest of tumor growth and progression.

In the therapy system of the present invention, the destruction or proliferation stasis of malignant cells is achieved by utilizing an AAD alone, or a combination of an AAD and one or more additional metabolic effectors. Each such combination contains an effective amount of ATP-availability depressor agent (AAD). Other metabolic effectors which may be present in the combination include one or more of the following:

(1) an effective amount of Lactate Export Blocking agent (LEB) for limiting the maximum rate at which lactic acid can be exported from the malignant cells;

(2) an effective amount of a Defined Nutritional Regimen (DNR) for limiting the amount of exogenously derived fatty acids and amino acids available to the malignant cells while providing calorically adequate glucose for the metabolism of the normal cells;

(3) an effective amount of a Fatty Acid Blocking agent (FAB) for limiting the rate of availability of energy to the malignant cells from endogenously derived free fatty acids;

(4) an effective amount of an Amino Acid Blocking agent (AAB) for limiting the rate of availability of energy to the malignant cells from endogenously derived amino acids.

The present invention consists of either (1) administering an AAD solely, or (2) concurrently administering an AAD and at least one other metabolic effector from among the LEB, DNR, FAB and AAB. See FIG. 3 for reference to the specific loci of action of these effectors in the energy-metabolism chain of malignant cells. The AAD per se is designed to degrade a substantial portion of the ATP as is produced or is potentially producible by the cancer cells, thus making it unavailable for use in supporting cellular metabolic requirements. The AAD may comprise one or more ATP-availability depressor agents or "ATP-availability depressors" (AAD), which result, at an adequate level of administration, in the lowering or depression to a lethal level in the cancer cells of the net rate at which ATP ($ATP_A$) is actually available for satisfying cellular metabolic needs, by directly inhibiting the synthesis rate of ATP per se (e.g., use of uncoupling agents of O/P) and/or inactivating or hydrolyzing ATP already synthesized (e.g., by use of ATPase hydrolysis-activity enhancing agents).

The additional metabolic effectors that can be used in combination with the AAD are designed to enhance the oncolytic effectiveness of the AAD, and permit achievement of malignant cell destruction in the body with lower levels of administration of the AAD per se. One or more of the additional metasbolic reflectors can be used in combination with the AAD. These metabolic reflectors include:

(1) one or more Lactate Export Blocking agents (LEB) for limiting the maximum rate at which lactic acid can be exported from malignant cells;

(2) a Defined Nutritional Regimen (DNR) which consists essentially of a dietary regimen designed to maximize the use of nutritional glucose-yielding carbohydrates as a source of ATP energy and to minimize the availability of nutritional fatty acids and amino acids for use as a source of ATP energy;

(3) one or more Fatty Acid Blocking agents (FAB) for limiting the rate of availability of energy to the malignant cells from endogenously derived free fatty acids; and (4) one or more Amino Acid Blocking agents (AAB) for limiting the rate of availability of energy to the malignant cells from endogenously derived amino acids.

In the regimens in which the combination of metabolic effectors used includes both the AAD and the LEB (with or without the other metabolic effectors), death of the malignant cells is effected by imposition of a lethally low intracellular pH ($pH_L$).

In the present invention, it is preferred to use an AAD in combination with a LEB. It is most preferred to use all five components, i.e., AAD, LEB, DNR, FAB and AAB, in concurrently administered combination.

Any of several regimens employing the metabolic effectors can be used, within the scope of the present invention, to effect oncolysis. These regimens include, but are not limited to, the administration of (a) AAD, (b) AAD+LEB, (c) AAD+DNR, (d) AAD+LEB+DNR, (e) AAD+DNR+FAB, (f) AAD+LEB+DNR+FAB+AAB, (g) AAD+DNR+AAB, and the like. It is preferred to use a regimen of AAD+LEB. It is most preferred to use a regimen of AAD+LEB+DNR+FAB+AAB.

Actions of the Primary Metabolic Effectors

In order to provide a clear and comprehensive understanding of the fundamental metabolic precepts and salient therapeutical features of the present invention, the following narrative of this section presents a detailed account of the direct actions and synergistic interactions of the metabolic effectors. For this purpose, the actions and interactions are discussed for the particular case of the most preferred embodiment of the invention so as to demonstrate the individual action of each effector and the actions of all the effectors in combination. For purposes of illustrative clarity, the effectors are arbitrarily grouped into three concurrently administered regimens and discussed in the order of their specific action loci along the energy metabolism pathway of the cancer cells (FIG. 3).

In normal (i.e., non-malignant) cells in the body, as depicted schematically in FIG. energy for ATP production is derived primarily from the sequential catabolism of glucose via the EMP, CAC and RC. Secondary sources of energy are fatty acids and amino acids which, after degradation to acetyl coenzyme A or intermediary metabolites of the CAC, enter the CAC for further catabolism. The relatively small amount of energy (per glucose molecule) deriving from the degradation of glucose to pyruvate in the EMP passes, along with that from the CAC and RC, in the form of ATP into the cellular ATP pool, from which it is withdrawn continuously to support overall cellular metabolism.

Figure 2:
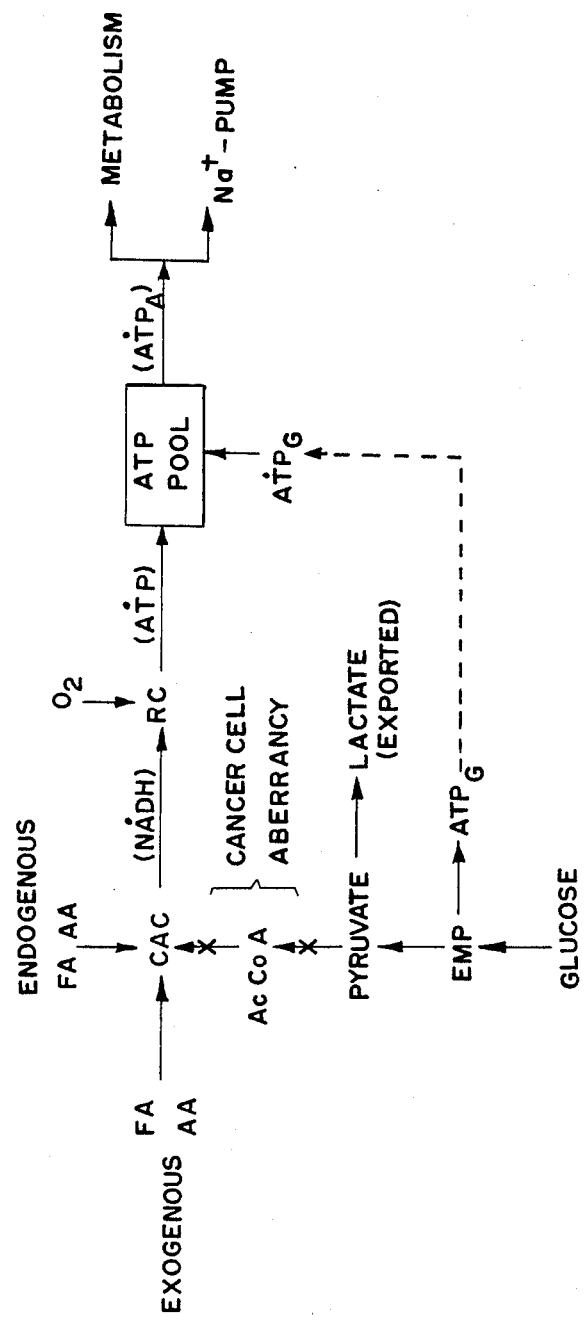
FIG. 2 is a flow diagram depicting the energy pathway for ATP production and usage in malignant cells. The ( —X→ ) means a substantially reduced rate of flow or inhibition of pathway.

As illustrated schematically in FIG. 2, malignant cells in the body are substantially unable to convert pyruvate, derived from glucose degradation in the EMP, to AcCoA, converting it instead to lactic acid which is excreted from the cell without further degradation. However, the malignant cells are fully capable of complete oxidation of FA and AA via the CAC-RC for ATP-energy production, when such substrates are available. When FA and AA availability is restricted, the cancer cells are able to generate ATP at an appreciable rate by strongly increasing the rate of glycolysis GLY (i.e., the rate of conversion of glucose to lactic acid in the EMP), producing overall two molecules of ATP for each molecule of glucose glycolyzed (as compared to 32 molecules of ATP produced in normal cells by oxidation of the pyruvate from each molecule of glucose in the CAC-RC). This high rate of cancer-cell GLY requires a commensurately high rate of lactate export to prevent the buildup of acidity in the cells to a lethal level.

The integrated mechanism by which cancer cells in the body are selectively destroyed by administration of the most preferred embodiment of the present therapy system is illustrated schematically in FIG. 3. This diagram shows the specific points in the energy-production chain of cancer cells where the five primary metabolic effectors DNR, FAB, AAB, AAD, and LEB of the present invention, act. The first major provision in the most preferred embodiment of the present therapy system is a regimen for imposing a limit on the maximum rate of supply of NADH (NADH) to the RC of the cancer cells. This requires that the rate of availability of the principal oxidative energy-yielding substrates for the CAC of the cancer cells, FA and AA, be minimized as much as clinically possible. FA and AA for the cancer cells are obtained from two sources, dietary and/or parenteral intake (exogenous sources), and mobilization from internal body depots or stores (endogenous sources). The latter sources include plasma FA which are maintained by continuous turnover of adipose fat stores and plasma AA which are derived from the continuous turnover and degradation of tissue proteins.

The control of exogenous FA and AA availability is readily achieved by administration of a defined nutritional regimen (DNR) which provides orally and/or parenterally the lowest possible level of FA other than the essential fatty acids linoleic and linolenic, AA sources such as protein, adequate only to maintain body nitrogen balance, and carbohydrate sources of glucose which supply substantially all of the daily caloric intake required for the daily caloric balance of the body. The DNR thus effectively restricts the dietary (exogenous) availability of FA and AA to the cancer cells, while providing adequate glucose for the normal cells to calorically satisfy overall body energy needs. This pegging of the rate of supply of exogenous FA and AA for ultimate metabolism in the CAC of the cancer cells, with consequent limitation of the maximum rate of NADH supply to the mitochondrial RC, is shown schematically in FIG. 3. (CAC in FIG. 3 denotes the rate of operation of the Citric Acid Cycle, i.e., the rate at which NADH is produced, e.g., $\mu$mol/min.) The daily amount of DNR caloric intake (Kcal/d) is readily determined by measurement of the individual patient's resting metabolic rate (i.e., patient's oxygen consumption per 24 hours under resting conditions) and estimation or similar measurement of the active metabolic rate corresponding to the level of activity in which the particular patient engages during the day. The minimum daily caloric intake is then calculated as one-half of the sum of the resting and active metabolic rates in $lO_2/d$ converted to its caloric equivalent in Kcal/d. Detailed procedures for precise DNR compositional and caloric balance determinations, suitable for use in the present therapy system, are given in U.S. Pat. No. 4,724,234.

Although control of exogenous FA and (to a lesser extent) AA intake is most advantageous in order to limit the availability of these energy substrates to the cancer cells, control of the availability of energy from FA and AA from endogenous sources is equally important. It has been found clinically that cancer patients exhibit in general a pronounced elevation of the free fatty acid concentration in the plasma, ranging from 200% to well over 400% above the average normal human plasma level of 190 $\mu$g/ml, as well as a substantial elevation in the plasma free amino acid level (particularly in patients in advanced malignant disease states). The major cause of these endogenous FA and AA elevations in cancer patients appears to be the generally existing psychological and physiological stress fostered by the disease and, in many cases, by the treatment regimen itself, particularly if the treatment is toxic and unduly stressful. Sustained elevated secretion rates of stress-responsive adrenal hormones (e.g., epinephrine and cortisol) fostered by conditions of chronic stress can act to maintain a chronic elevation of FA and AA in the plasma. Epinephrine, for example, is the most potent known mobilizer of free fatty acids from body adipose tissue and fat depots, while the sustained action of the adrenal cortex cortisol results (through pronounced inhibition of cellular protein synthesis) in an appreciable elevation in the plasma AA concentration, as well as directly producing an elevation in plasma FA from adipose depots. Consequently, the overall restriction of the FA and AA oxidative energy to the cancer cells requires the administration of agents that effectively inhibit the availability or oxidative metabolism of endogenously derived FA and AA, in addition to the concurrent administration of the DNR.

In the present invention, oxidative use of endogenously derived FA by the cancer cells for ATP-energy production is effectively inhibited by administration of one or more free fatty acid blocking agents (FAB), acting at the point shown in FIG. 3. A most effective and preferred FAB, for example, is long-acting or lente insulin, which is injected intramuscularly on a daily basis. Medically, at present, lente insulin is conventionally used almost exclusively for control of the plasma glucose concentration level in diabetic individuals. However, insulin has long been known also to impose a profound inhibition of free fatty acid mobilization from body adipose tissues. It has been found in detailed clinical studies by the present inventor, for example, that administration of a daily dose as small as 10 to 15 I.U. of lente insulin readily decreases the plasma FA level of cancer patients from some 400 to 900 $\mu$g/ml to as low as 70 $\mu$g/ml, and maintains this low level for nearly 24 hours in the presence of concurrently administered DNR, while the plasma glucose concentration remains within the normal physiological range. Thus, lente insulin is capable of reducing the maximum free fatty acid availability by some 92%, a most significant reduction considering that the endogenously derived free fatty acids constitute the primary energy source of the cancer cells after the DNR administration. In principle, regular or short-acting insulin could readily be used as a FAB, but has the clinical disadvantage of requiring more frequent injections in a 24-hour period. In the use of lente insulin as the FAB of the present invention, the desired inhibition of FA use for energy production by the cancer cells is achieved by means of a pronounced reduction in the rate at which endogenous FA can be mobilized from adipose depots.

An example of another effective type of FAB that has been evaluated clinically, but which acts by an entirely different mechanism from that of insulin, is the fatty acid oxidation inhibitor, of which the agent 2-tetradecylglycidate is representative [Tutweiler, G. F. et al., *Federn. Proc.* 37 1308 (1978); Tutweiler, G. F. et al., *Clin. and Exper. Metabolism* 27 1539 (1978)]. These FAB act by inhibiting directly one or more enzymes in the mitochondrial β-oxidation pathway of cancer cells or, as is the case with methyl 2-tetradecylglycidate, by inhibiting transport of the FA into the mitochondria for degradation and oxidation by the CAC. The point of action of the FAB is shown in FIG. 3, which schematically depicts the FAB as blocking or inhibiting endogenously derived FA from being used as substrates for the CAC, thereby decreasing the maximum rate CAC at which the CAC can operate in producing NADH for the RC.

Although the oxidation of FA constitutes the major source of the oxidatively (CAC-RC) derived energy of cancer cells, considerable evidence exists demonstrating the concomitant oxidation of AA for energy production in these cells under adverse nutrient-availability conditions. Consequently, inhibition of the availability of endogenously derived AA for oxidation by administration of an amino acid blocking agent (AAB) provides an additional means in the present invention for reducing the overall rate at which the cancer cells can produce NADH for their energy needs. Generally, actively proliferating cancer cells conserve AA for use primarily in protein synthesis, and utilize the energy-rich FA for ATP energy production [see U.S. Pat. No. 4,724,234]. Under conditions of low FA-energy availability, as imposed by the DNR and the FAB of the present therapy system, oxidation of AA may become of considerable importance for cancer cell survival, and utilization of the AAB becomes beneficial oncolytically. In the present therapy system, the imposed AAB results either directly or indirectly in a decrease in the production of ATP energy derived from the oxidative degradation of endogenously supplied AA. An example of an AAB that has been effectively utilized clinically in the present therapy system is the drug aminoglutethimide. This agent acts indirectly by inhibiting the first step in the synthesis of cortisol from cholesterol in the adrenal cortex. As previously discussed, the primary cause of elevated plasma AA concentrations in cancer patients generally is chronically elevated cortisol, and both the plasma cortisol and AA levels in cancer patients are substantially lowered by administration of aminoglutethimide. Another example of an AAB which acts in part by means of a plasma cortisol level reduction, accomplished by a quite different physiological action, is stress-relieving psychotherapy. Chronically elevated cortisol levels due to stress are often significantly lowered by such psychotherapeutical regimens, which act to relieve or ameliorate the high mental stress levels of cancer patients, with resultant reduction in plasma AA (and FA) levels. Similarly, drugs which act to relieve or ameliorate stress per se constitute indirectly acting AAB. The point of action of the AAB in the present therapy system is shown in FIG. 3, which schematically depicts the AAB as blocking or inhibiting endogenously derivable AA from being used as substrates for the CAC, thereby decreasing the rate CAC at which the CAC can operate in producing NADH for the RC.

The individual and combined actions of the DNR, FAB, and AAB thus result in a lowering of the maximum rate CAC at which the CAC can operate due to the limited or pegged rate of substrate availability from combined exogenous and endogenous FA and AA, and consequently in a marked lowering of the maximum rate NADH at which NADH can be supplied to the RC in the cancer cells. This action in turn results in the pegging or limitation of the maximum rate of ATP production possible in the RC of cancer cells by oxidation of NADH. Simultaneously, the NADH of the normal cells of the body is not limited in any way by the administration of the DNR, FAB, and AAB, since these cells can fully oxidize the abundant glucose provided by the DNR. The cancer cells are thus selectively and effectively limited with respect to the maximum rate at which NADH can be provided to and oxidized in their RC (i.e., limited in their maximum RC), and consequently in the maximum rate at which ATP can be produced by the RC.

The second major provision in the most preferred embodiment of the present therapy system is a regimen for lowering, selectively in the cancer cells, the overall rate $\hat{ATP}_A$ at which ATP is available for supporting the total cellular metabolic energy needs. This $\hat{ATP}_A$ lowering is accomplished by the administration of one or more ATP-availability depressor agents (AAD). The ultimate action thereof (at adequately high levels of administration) is to lower the $\hat{ATP}_A$ to a level which is inadequate to sustain even the minimal vital metabolic processes of the cancer cells required to maintain viability, and consequently to effect death and lysis of these cells by energy starvation. This lowering of the $\hat{ATP}_A$ is accomplished by the AAD, for example, by decreasing the rate of production of ATP per se by uncoupling O/P in the RC, or by wastefully hydrolyzing ATP already made, or by sequestering the existing ATP molecule so as to make it unreactive in energy-requiring metabolic reactions. These actions of the AAD are collectively referred to herein as "ATP wasting," since they all result in the wasteful removal of ATP from the ATP pool and thus prevent its availability for use in satisfying cellular metabolic needs. Since, in the cancer cells, the rate of NADH oxidation in the RC is limited to a low level by the DNR-FAB-AAB imposed restriction on the availability rate of NADH, the RC cannot increase above this pegged level as ATP is wasted by the administered AAD. Consequently, the AAD-wasted ATP cannot be compensated for, in the cancer cells, by an increase in the operational rate of the RC, i.e., an increase in the rate RC of NADH oxidation to produce ATP at a greater rate. As a result, as the level of AAD action is increased, the net available-ATP rate, $\hat{ATP}_A$, for accommodating cellular metabolic reactions and processes decreases, ultimately reaching a lethal level of depression, $\hat{ATP}_A = \hat{ATP}_L$, at an adequate level of AAD administration. In the normal cells, the AAD also acts to waste ATP, but since the normal cells can fully utilize the abundant glucose of the DNR, they experience no restrictive limit on the CAC or NADH to the RC. Consequently, the RC increases as much as is necessary to compensate for the AAD-wasted ATP, thus insuring maintenance of a normal level of the $ATP_A$ for satisfying all normal cellular metabolic needs. The normal cells are thus unaffected energywise by the administration of the AAD, while the cancer cells are energy-starved to a lethal level, $ATP_L$, at an adequately high level of AAD.

As the $ATP_A$ in the cancer cells is depressed by the action of the AAD, the concentration of cellular ATP will ultimately begin to decrease, since the rate of useup of ATP is then transiently greater than the rate at which it can be supplied. This ATP concentration decrease stimulates an increase in the rate of glycolysis (GLY) which yields additional usable ATP (2 moles of ATP per mole of glucose glycolyzed). The overall AAD wasting action must be adequate, therefore, to also overcome the increased availability of this glycolytically derived ATP. In general, however, the production of ATP by glycolysis is very inefficient and metabolically demanding. For example, to fully compensate for the AAD wasting in the malignant cells of a malignant neoplasm of the ATP derived from complete oxidation via the CAC-RC of the energy equivalent of one mole of glucose per unit time would require the glycolytic degradation of 16 moles of glucose per unit time, with the concomitant production of 32 moles of lactic acid, which must be immediately exported. Consequently, the GLY would have to increase 1,600% and the $LAC_p$ 1,600%. In general, the LAC export rate capability of cancer cells is very large, so that it is most likely in the usual situation that the GLY per se will reach a maximum limit (peg), as $ATP_A$ decreases, before the LAC export capability becomes saturated. Consequently, the $LAC_p$ will reach a maximum and there will be no lethal buildup of acidity in the cells; $ATP_A$ will continue to decrease to the lethal level $ATP_L$ and the cancer cells will die from energy starvation. It is possible, in principle, that under certain conditions GLY may not reach a rate-limited state before the LAC export capability becomes saturated (i.e., before $LAC_E$ becomes maximally rate-limited or pegged), whence the cells will die from a lethal acidity buildup, $pH = pH_L$, before $ATP_A$ reaches the $ATP_L$ level. However, cancer cell death by $pH_L$ would not generally be expected because of the large LAC export capability. Thus, the cancer cells will generally die from energy starvation rather than from a lethal pH depression to $pH_L$ when exposed to the DNR-FAB-AAB-AAD metabolic effector combination of the present therapy system. However, great therapeutical advantage is taken of the strong stimulation of the GLY by the AAD-mediated $ATP_A$ depression by additional administration in the present system of lactate export blocking agents (LEB), as is described subsequently.

An example of one very effective class of AAD which has been extensively evaluated in clinical administrations of the present therapy system comprises agents which uncouple phosphorylation from oxidation in the mitochondrial RC (i.e., the so-called O/P uncoupling agents (UA)). The clinical use of this form of AAD has been described in detail previously [U.S. Pat. No. 4,724,234]. The UA act to release the energy derivable from the oxidation of NADH in the RC of cells as heat, thereby preventing synthesis of an equivalent amount of ATP. In the normal cells, the CAC and RC increase so as to exactly maintain a normal $ATP_A$, since these cells can fully use the abundant glucose provided by the DNR. In the cancer cells, since the CAC and RC are rate-limited (or pegged) by the DNR-FAB-AAB, the UA results in a net decrease in $ATP_A$ (once the ATP available from the increased GLY becomes maximal). Another example of a highly preferred AAD is thyroid hormone (TH). The administration of TH (i.e., $T_4$ and/or $T_3$, or their pharmacological equivalent in thyroglobulin or dessicated thyroid gland) results in an increase of the overall pericellular membrane $Na^+/K^+$-dependent ATPase activity of cells, which results in an increased rate of active outpumping of $Na^+$ through the pericellular membrane to accommodate a concomitant increase in membrane permeability to $Na^+$ [Smith, T. J. et al. *Federn. Proc.* 38 2150 (1979); Guernsey, D. L. et al. *Molecular Basis of Thyroid Hormone Action* Chapter 10, Academic Press, New York (1983)]. This action produces the pronounced calorigenesis characteristic of thyroid hormone elevation in the body, and serves as a primary means for maintaining body temperature in warm blooded animals by wasting already-synthesized ATP. In the present therapy system, when used as an AAD, TH indirectly effectively hydrolyzes and wastes cellular ATP after it is synthesized, for wasteful (calorigenic) out-pumping of $Na^+$. This ATP-wasting in the cancer cells acts in the present therapy system to strongly depress the $ATP_A$, since their CAC and RC are already rate limited by the DNR-FAB-AAB. In normal cells, this TH-mediated ATP-wasting is precisely compensated for by a commensurate increase in the CAC and RC using glucose supplied by the DNR. For the purposes of the present invention, any clinically tolerable agent (i.e., substance, means or procedure) which acts to waste the energy of potentially synthesizable or already synthesized ATP or to prevent its use for usual and necessary cellular metabolic reactions constitutes an AAD. Thus, possible AAD include, but are not limited to, O/P uncoupling agents which waste the energy of potentially synthesizable ATP, intracellular introduction of inappropriate foreign ATPases, substances or means which inappropriately increase the activity of natural cellular ATPases, chemical agents that cause direct, generalized wasting-hydrolysis of ATP within the cell, agents that selectively bind to and energetically inactivate ATP, and molecular species which generally competitively inhibit existing ATP participation in normal metabolic reactions.

In FIG. 3, the AAD is shown as acting at the RC level to wastefully inhibit ATP synthesis (as with the UA) and at the level of the already-made ATP (as with the TH). The various AAD may be used singly, or in combination in order to maximize overall effectiveness while maintaining a relatively low level of each particular AAD. The therapeutical result is the depression of the $ATP_A$ ($ATP_A \downarrow$) to the lethal level, $ATP_A \leq ATP_L$. This condition of death by energy starvation is depicted in FIG. 3 by the upper terminal branch of the diagram.

The third major provision of the most preferred embodiment of the present therapy system is the administration of a lactate export blocking agent (LEB) concurrently with the DNR-FAB-AAB-AAD combination of metabolic effectors. The LEB acts to effectively inhibit the export of lactate from the cancer cells, with the consequence that with the AAD of the present therapy system the ensuing buildup of lactic acid within the rapidly glycolyzing cell ultimately results in the depression of the intracellular pH to a lethal level $pH_L$. As depicted in the lower terminal branch of FIG. 3, the AAD-depressed $ATP_A$ level causes a decrease in the intracellular concentration of ATP (decreased ATP pool, suora) which then stimulates an increase in the GLY by stimulation of increased phosphofructokinase (the rate-limiting enzyme of the EMP) activity in the Embden-Meyerhof pathway. This results in a commensurate increase in $LAC_p$. In the presence of the LEB, the maximum $LAC_E$ is effectively lowered due to inactivation of part of the available export capacity. When, through imposition and maintenance of adequate levels of AAD and LEB, $LAC_p$ exceeds the maximum $LAC_E$ possible, LAC concentration continuously increases in the cancer cells and the intracellular acidity ultimately reaches a lethal level ($pH=pH_L$). The action of the LEB strongly decreases the maximum possible $LAC_E$ by binding to and inactivating a portion of the lactate-exporting molecular moieties in the cell membrane [Spencer, T. L. et al. (1976), supra; Belt, J. A. et al. (1979), supra], while the high GLY stimulated by the AAD depression of the $ATP_A$ greatly increases the $LAC_P$; ultimately $LAC_p > LAC_E$ maintains and lethal acidity buildup ensues in the cancer cells. Adequate levels of LEB ensure that $LAC_p$ will become greater than the pegged $LAC_E$ at GLY levels before the maximum operational GLY level is reached, and hence that the cancer cells will die of a lethal pH depression.

The importance of the $ATP_A$ decrease, obtainable with the AAD of the concurrently administered DNR-FAB-AAB-AAD combination of the present invention, is paramount in securing the LEB effectiveness. The $ATP_A$ can be continuously decreased with adequate AAD increase, to exert an increasingly stronger GLY stimulation so as to maintain the increased GLY against the GLY-increase-limiting effect of the decreasing intracellular pH per se, so that the intracellular acidity continues to increase in the presence of the LEB. The decreasing intracellular pH otherwise exerts an increasingly strong inhibiting effect on enzymes of the EMP as the pH decreases below the normal intracellular pH level of ~7.0, with a consequent decrease in the maximum GLY level attainable as the pH decreases.

In general, it is not possible to achieve a full 100% blockage of the lactate export capacity of cancer cells with a LEB, and hence not possible to achieve a $pH_L$ with a LEB alone. Also, the concentration of LEB required to effect a given percentage blockage of the initial maximum export capacity (i.e., that without any LEB) increases very rapidly as the percentage blockage is increased. For example, the average LEB concentration increase per percent-unit of lactate export blockage in going from 80% to 95% blockage is 10-fold greater than that required in going from 40% to 80% blockage. The low $ATP_A$ attainable by the DNR-FAB-AAB-AAD (or AAD by itself) of the present therapy system therefore acts to permit and ensure a lethal level of effectiveness of the LEB, which otherwise would not be attainable at clinically practicable levels of LEB. The high GLY and $LAC_p$ fostered by the AAD-mediated $ATP_A$ decrease thus ensures saturation of the LAC export rate capacity (i.e., $LAC_p > LAC_E$) of the cancer cells at moderate LEB levels much below the clinically unattainable 100% blockage required to effect complete saturation with the LEB alone. Lethal pH levels can thus be attained with relatively low levels of LEB administration, which may be clinically quite beneficial with certain LEB agents, and use of LEB which cannot achieve high levels of transport blockage becomes possible. Alternately, the use of the LEB markedly reduces the degree to which the $ATP_A$ would have to be depressed, to otherwise produce lethality by $ATP_A \leq ATP_L$ (energy starvation), and hence considerably lowers the overall body metabolic rates (due to ATP wasting in normal cells) which would otherwise exist during treatment. These important synergistic interactions are summarized in FIG. 3 in the lower terminal branch of the diagram. The $ATP_A$ causes the GLY to increase, giving a higher $LAC_p$ and $LAC_E$. With administration of the LEB, the maximum $LAC_E$ possible becomes pegged at a low level, whence with continuing LAC production at an elevated rate the intracellular pH ultimately decreases to a lethal level $pH_L$.

An example of a most preferred LEB which has great clinical efficacy when used in the present therapy system is the naturally occurring plan flavonoid quercetin (3,5,7,3',4'-Pentahydroxyflavone). The first comprehensive study of lactate export inhibition in a cancer cell form in vitro utilized quercetin [Spencer, T. L. et al.(1976), supra]. Subsequently, many bioflavonoids have been shown in vitro to be effective inhibitors of lactate export in malignant cells [Belt, J. A. et al. (1979), supra]; however, they have not previously been shown to be capable per se of effecting the death of malignant cells in vitro or in vivo.

Figure 4:
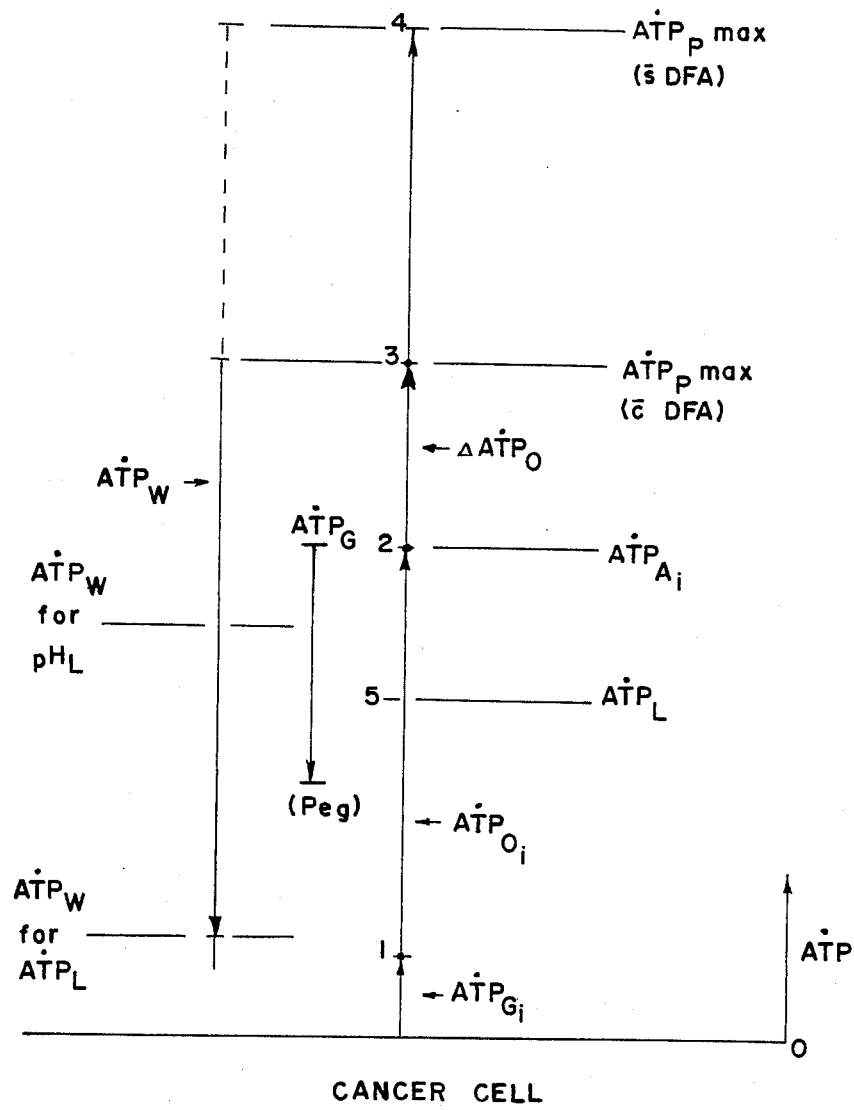
FIG. 4 is a schematic summary of the coordinated effect of all five primary metabolic effectors in terms of rates of ATP production and degradation. DFA indicates the combination of DNR-FAB-AAB.

These coordinated and advantageously synergistic actions of the primary metabolic effectors (AAD, DNR, FAB, AAB and LEB) are summarized schematically in FIG. 4 in terms of cancer cell ATP production and wasting rates (e.g., μmol ATP/min/Kg cells). Level 1 is the rate ($ATP_{Gi}$) at which the cancer cell is producing ATP via glycolysis initially, prior to therapeutical intervention. Level 2 is the initial total rate ($ATP_{Ai}$) at which ATP is available for use by the cell for its ongoing metabolic requirements. $ATP_{Ai}$ is the sum of the initial glycolytic ATP production rate $ATP_{Gi}$ and the initial O/P ATP production rate via the CAC-RC oxidative pathway, $ATP_{Oi}$. $ATP_{Ai}$ is equal to $ATP_{Ri}$, the initial overall rate at which ATP is being metabolically used up by the cell. Upon administration of the AAD in increasing dosage (mg/Kg), or activity level, the level of $ATP_O$ will increase ($\Delta ATP_O$) commensurately, due to a slight transient decrease in $ATP_A$ (below $ATP_{Ai}$ and $ATP_{Ri}$) and to the associated decrease in [ATP], the concentration of ATP in the cell, to precisely compensate for the rate $ATP_W$ at which ATP is being wasted by the AAD. Without the DNR+FAB+AAB (collectively denoted as "DFA" in FIG. 4), the total ATP production rate ATPP would rise to level 4 ($ATP_{pmax}$sDFA) as the AAD dosage level is continuously increased, where it pegs (becomes maximized) due to a natural limit on the rate of availability of FA and AA for the CAC. With the administration of the DNR+FAB+AAB, however, $ATP_p$ can rise only to level 3 ($ATP_{pmax}$cDFA) before becoming pegged due to a more limited rate of FA and AA availability for the cancer cell CAC. Thus, administration of the DNR+FAB+AAB significantly lowers the maximum rate at which the cancer cell can produce additional compensating ATP ($\Delta ATP_O$) by oxidative-phosphorylation as the AAD dosage is continually increased.

When $ATP_p$ reaches level 3 with increasing AAD administration, a further increase in AAD results in a transient decrease of $ATP_A$ below $ATP_{Ai}$ (and $ATP_{Ri}$) and of [ATP] below $[ATP]_i$. This further decrease in [ATP] then drives phosphofructokinase (PFK), the rate-limiting enzyme of the EMP, to a higher level of activity and GLY and $\Delta ATP_G$ increase steadily to compensate for the increased $ATP_W$ wasting as the AAD is increased. All during this overall AAD increase, [ATP] remains slightly less than $[ATP]_i$, by an amount that is just sufficient to replace the $\dot{ATP}_W$ loss by stimulating an increased rate of ATP production, first by the $\dot{ATP}_O$ increase $\Delta\dot{ATP}_O$ (until its peg is reached) and then by increased GLY, $\Delta\dot{ATP}_G$. Without administration of the LEB, at a sufficiently high level of AAD administration GLY will ultimately peg (i.e., the EMP will reach its maximum operational capacity), whence further increase in AAD will force $\dot{ATP}_A$ to decrease strongly (below $\dot{ATP}_{Ai}$), since both $\Delta\dot{ATP}_O$ and $\Delta\dot{ATP}_G$ are now pegged, until the lethal energy starvation level $\dot{ATP}_A\dot{ATP}_L=$ is reached. In the presence of an adequate level of LEB, however, imposing a substantial percentage blockage of the cell's normal maximum lactate export capacity, the high $\dot{LAC}_p$ of the greatly increased GLY soon exceeds the maximum possible $\dot{LAC}_E$ as the AAD is increased, whence the cellular pH decreases to a lethal level, $pH_L$. Consequently, with the LEB the cancer cell dies of lethal acidity substantially before the $\dot{ATP}_L$ starvation level can be reached.

The total rate of ATP wasting by the AAD required to produce lethality without the LEB ($\dot{ATP}_W$ for $\dot{ATP}_L$) and with the LEB ($\dot{ATP}_W$ for $pH_L$) are denoted in FIG. 4, along with the associated increases in the glycolysis-ATP rate $\Delta\dot{ATP}_G$ which must be overcome. The significant decrease in the overall level of $\dot{ATP}_W$ generated by the AAD required to produce lethality with the coadministered DNR-FAB-AAB-LEB combination of metabolic effectors versus that without the LEB (and with or without the DNR-FAB-AAB) is evident. Moreover, since the overall $\dot{ATP}_W$ level of ATP wasting is also experienced by the normal cells, with a commensurate rise in their CAC-RC to provide glucose-derived compensating $\dot{ATP}$ (to keep their $\dot{ATP}_A$ essentially equal to their $\dot{ATP}_{Ai}$ and to their $\dot{ATP}_{Ri}$), the pronounced decrease in required AAD effected by the coadministered DNR-FAB-AAB-LEB combination also results in a significant reduction in the overall whole body resting metabolic rate (i.e., $O_2$ consumption rate) increase during treatment. As the initial $\Delta\dot{ATP}_O$ increase takes place, a small increase in $\Delta\dot{ATP}_G$ also concurrently occurs because of the small decrease in [ATP], but this is included in the overall $\Delta\dot{ATP}_G$ in FIG. 4. $\dot{ATP}_R$ remains equal to $\dot{ATP}_{Ri}$ during the rise of $\dot{ATP}_W$ to its maximum (i.e., until cell death), provided the AAD action is imposed rapidly enough.

In the unlikely event that the increase in $\Delta\dot{ATP}_G$ (i.e., in $\Delta GLY$) becomes pegged in a cancer cell before the intracellular $pH_L$ is reached, death by lethal acidity buildup will not occur. Such pegging of $\Delta GLY$ could conceivably occur in some cells, since GLY is inhibited by lower pH levels [Spencer at al. (1976), supra: Belt, J. A. et al. (1979), supra]. However, a pegging of GLY in the present therapy system would simply mean that the overall $\Delta\dot{ATP}_G$ that the $\dot{ATP}_W$ had to overcome was less, whence the $\dot{ATP}_L$ (lethal energy starvation) level could be reached sooner (i.e., at a lesser level of AAD administration). In effect, such a pH-imposed peg of $\Delta GLY$ constitutes a selective blockage of the EMP specifically in the cancer cells and hence permits an easier attainment of the $\dot{ATP}_L$ level with the AAD. Interestingly, in such a case the LEB actually serves to enhance cancer cell death by energy starvation, rather than by lethal acidity ($pH_L$). Clinically, the important point is that with the present therapy system, cancer cell death is insured, whether $\Delta GLY$ becomes pegged or not with the LEB.

While the foregoing therapeutic principles described herein are clearly applicable to mammals generally, the treatment regimen as elucidated in detail hereinafter ("Illustrative Therapy System for Human Patients") is of specific applicability to humans and other mammals with comparable active and resting metabolic rate ranges—i.e., other primates. Specific adaptation of this invention to other mammals, e.g., with significantly higher or lower active and resting metabolic rate ranges is within the scope of this invention and can, using the principles herein described, be effected by those skilled in the requisite technology without departing from the invention. It is indeed contemplated that the therapy of the invention, with suitable adaptation to take account of the active and resting metabolism of the animal to be treated such as to maintain daily caloric balance, will be particularly useful in the treatment of malignant neoplasms in valuable agricultural animals, pets, zoo animals, race horses and other pedigreed stock, et cetera.

Defined Nutritional Regimen (DNR)

The essential features of the DNR of the present invention, independent of the overall therapeutical regimen thereof which is utilized, are the provision of (a) an absolute minimum of fat, which the cancer cells can use for ATP-energy production, so as to supply substantially only the minimal levels of the essential fatty acids, (b) a minimum of protein, which the cancer cells can use for ATP-energy production and for mitogenic anabolism, albeit an amount which is adequate on the average to maintain the whole-body nitrogen balance without excess during the overall treatment period, and (c) an allowance of carbohydrate which, after subtraction of the total fat and protein caloric contributions, provides glucose sufficient to furnish the remaining daily calories required to satisfy the total daily caloric requirements of the body. The amount of DNR given should avoid any substantial excess, since excess glucose would be converted to fatty acids which would then be readily available to the cancer cells for ATP-energy production in the absence of adequate FAB; malignant cells have been demonstrated to possess full capability for converting glucose to fatty acids [Abraham, S. et al., *Proc. Am. Assoc. Cancer Res.* 2, 89 (1956); Begg, R. W. et al., *Fed, Proc.* 15, 216 (1956); Medes, G. et al., *Cancer Res.* 13, 27 (1953)].

The total daily caloric requirement (Kcal/d) of the individual patient may be determined simply by increasing the caloric amount of the DNR to a level which prevents a successive daily loss or gain of body weight. Alternately, the daily caloric requirement can be determined precisely by performing an actual measurement of the resting metabolic rate (i.e., $O_2$ consumption rate), converting this measurement value to its caloric equivalent for the DNR being administered, and adding in an appropriate caloric allowance for the daily activity level of the patient. (U.S. Pat. No. 4,724,234 presents a detailed discussion of metabolic rate measurements for precise DNR caloric calculations.) Actual metabolic rate measurements are preferred when using UA as AAD in the present invention because of their pronounced capability to elevate body metabolic rate.

In Phase I of the preferred treatment protocol of the present therapy system (see "Illustrative Therapy System for Human Patients", infra), the essential fatty acids, protein, and carbohydrate components of the DNR are derived from essentially pure sources or sources of known analysis, and the DNR is administered in the form of liquid-suspension cocktails at periodic intervals over the day. The preferred component sources are:

(1) for essential fatty acids: linoleic and linolenic acids at 1% of the patient's normal daily caloric requirements from sources such as primrose oil, or a mixture of safflower and linseed oils, (2) for protein: casein or egg protein, and (3) for carbohydrate: a mixture of pure dextrose, sucrose, and starch. The protein source used should provide a high quality amino acid complement. That is, the relative proportions of the amino acids should be those corresponding to average human protein composition; otherwise amino acids which are below their human proportionate equivalent will result in the inability of the anabolic use of the other amino acids (which will be in proportionate excess), whence they will become available as oxidative energy sources for the cancer cells. Non-nutritive bran (nominally 0.45 g/Kg of body weight) may be added to the DNR to provide fiber and bulk, along with a vitamin and mineral mix, prior to blending. The vitamin and mineral allowance also contains KCl (65 mg/Kg) and NaCl (60 mg/Kg) since the purified preferred sources supply very little K and Na, along with at least twice the Recommended Daily Allowance (RDA) of all water-soluble and lipid-soluble vitamins, and appropriate levels of Ca, P, Mg, Mn, I, and Se, and choline.

In Phase II of the preferred treatment protocol, the DNR is provided in specific solid-food menus of natural food elements of defined nutrient content formulated so as to give the nitrogen-balance level of high quality protein, and as minimal an amount of fat as possible by the choice of low-fat food elements. The required carbohydrate allowance is composed of that occurring in the protein-supplying natural food elements, plus supplementation from substantially total-carbohydrate sources (candies, custards, and flavored carbohydrate beverages) to satisfy the total therapeutical caloric level necessary to an ambulatory patient or outpatient. Supplementary non-nutritive bran, if desired, and vitamins and minerals at the minimum RDA level or higher, are also provided in the completely specified DNR for Phase II of the preferred protocol.

Although the oral route is preferred for administration of the DNR, the use of total or partial parenteral alimentation procedures to administer substantially the nutrient equivalent of the DNR in a form suitable for infusion can readily be used when clinical conditions so demand. In such cases, administration of amino acids in pure and balanced form is of course required. An example is the case where, because of a malignant growth blocking the esophagus, a patient cannot swallow even semi-solid foods or liquids at the start of the therapy. Once the tumor mass has been regressed by the therapy, and swallowing of the DNR cocktails or tube-feeding is possible again, the preferred DNR cocktail ingestion procedure can resume. Additionally, total or partial parenteral administration can be used for particular elements of the DNR and/or particular vitamins and minerals which cannot be absorbed adequately when taken by the oral route in special patients.

When using relatively high dosages of or particularly potent AAD (such as UA, for example), the resting metabolic rate may temporarily elevate to levels above that which can be calorically balanced with the DNR. For short periods (i.e., 24 hours), this condition poses no problems since the most metabolically active normal tissue, viz., muscle, readily utilizes its internal creatine phosphate store to produce ATP, a store which, like liver glycogen, is particularly high from the DNR administered during periods of lower (i.e., calorically balanced) metabolic rates. For longer periods, supplementation with glucose infusion can be used. Under such conditions of temporary caloric intake deficiency, it is particularly desirable to administer a FAB in adequate dosage to prevent energy availability from an otherwise potentially gross (and oncolytically detrimental) rise in plasma free fatty acids from mobilized body fat depots.

Fatty Acid Blocking Agents (FAB)

The primary purpose of the FAB is to significantly inhibit energy production from endogenously derived body FA in the cancer cells. FAB may act at one or more of several metabolic levels, and one or more FAB may be used in combination in the present therapy system. Examples of some forms of FAB are as follows:

(1) FA Mobilization Inhibitors (FAB which act by inhibiting mobilization of free fatty acids from body adipose stores) include but are not limited to insulin (e.g., 5 to 45 I.U. of lente insulin per day, intramuscular injection) and epinephrine $\beta$-receptor blockers (e.g., Inderal).

(2) FA Transport Inhibitors (FAB which act by inhibiting the transport of FA into cells or into cellular mitochondria) include but are not limited to 2-tetradecylglycidic acid, methyl 2-tetradecylglycidate, malonyl CoA, D-acetylcarnitine, D-carnitine, deoxycarnitine, deoxynorcarnitine, L-carnitine, D-palmitoylcarnitine, D-decanoylcarnitine, crontonyl CoA, $\Delta 2,3$-hexadecenoyl CoA, p-chloromercuribenzoic acid and N-ethylmalemide.

(3) FA Metabolism Inhibitors (FAB which act by inhibiting specific enzyme-mediated reactions in the $\beta$-oxidation of FA for energy purposes) include but are not limited to orotic acid, dichloroacetic acid, 4-pentenoic acid, $\alpha$-amanitin, valproic acid, bromstearic acid, 2-bromooctanoic acid, hydrazine monohydrate, 1-phenyl-3-pyrazolidone, phenylpyruvic acid, $\alpha$-ketoisocaproic acid, methylenecyclopropylacetic acid and biguanides.

The foregoing is intended to be a representative but not exhaustive listing of FAB agents which can be used in practicing the present invention, commensurate with their clinical tolerability at effective dosage levels. Any one or any combination of such agents may be employed as the FAB of the present invention, commensurate with the tolerability of their in vivo use.

Provision of FAB to inhibit energy production from free fatty acids in cancer cells is particularly desirable in the present therapy system due to the ready and copious availability of fatty acids mobilizable from body stores when needed, and particularly under conditions of stress. Without such endogenous FA-availability restriction, levels of the AAD required to produce an adequately low $ATP_A$ for effecting cancer cell death by either energy starvation ($ATP_L$) or lethal pH depression ($pH_L$) with an LEB may not always be possible to impose clinically, at least not without undesirably high body metabolic rate elevations associated with the compensation for the AAD-wasted ATP by normal cells.

Amino Acid Blocking Agents (AAB)

The primary purpose of the AAB is to inhibit the use of endogenously-derived AA for energy production in the cancer cells. This inhibition of AA use is particularly desirable when endogenous FA use is effectively restricted, since the alternate oxidation of AA by the cancer cells could in principle provide in some cases an adequate rate of oxidative ATP production to preclude achieving cancer cell death by energy starvation or lethal pH. In general, it is the condition of an excessive plasma concentration of AA that is to be controlled, since AA from dietary proteins are normally rapidly taken up and utilized by the normal cells of the body. Elevated patient plasma concentrations of AA derive primarily from a chronic elevation of plasma cortisol, usually because of a continuing condition of physiological and/or psychological stress in the cancer patient. Consequently, the most effective AAB currently clinically available act indirectly by reducing the cortisol concentration to a more normal state, both in magnitude and duration of the elevation. Examples of some currently available forms of AAB are as follows:

(1) Agents which reduce the chronically elevated plasma cortisol levels by directly inhibiting cortisol synthesis in the adrenal cortex, including but not limited to aminoglutethimide (3-(4-aminophenyl)-3-ethyl-2,6-piperidinedione).

(2) Agents which enhance reduction of chronically elevated plasma cortisol levels by degradative removal in the liver, including but not limited to thyroid hormone ($T_4$ and $T_3$).

(3) Agents which reduce plasma cortisol levels by inhibiting excessive stimulation of the adrenal cortex by pituitary adrenocorticotropic hormone (ATCH), including but not limited to synthetic cortisol analogs and cyclic AMP inhibitors.

(4) Procedures which reduce chronically elevated plasma cortisol levels by inhibiting or normalizing excessive hypothalamic stimulation of hypophyseal ACTH release, including but not limited to stress-relieving psychotherapy.

ATP-Availability Depressor Agents (AAD)

The basic purpose of the AAD, alone or in combination with other metabolic effectors, in the present therapy system is to effect a reduction, selectively in the cancer cells, of the maximum rate at which ATP is available for supporting essential metabolic energy requirements. The AAD depresses the ATP availability rate $A\dot{T}P_A$ of the cancer cells to a level which permits attainment of a state of lethal cancer cell starvation ($A\dot{T}P_A = A\dot{T}P_L$), or lethal pH depression ($pH = pH_L$) when utilized with a LEB. Examples of some of the forms of AAD are as follows:

(1) Agents which inhibit the oxidative ATP production rate by uncoupling oxidation and phosphorylation in the RC: O/P uncoupling agents, UA, including but not limited to 4-hydroxy-3,5-diiodobenzonitrile; benzotriazoles, such as 5-nitrobenzotriazole, 5-chloro-4-nitrobenzotriazole, or tetrachlorobenzotriazole; benzylidenemalononitriles, such as 4-hydroxybenzylidenemalononitrile [4-OH-BMN], 3,5-ditertbutyl-4-hydroxybenzylidenemalononitrile, 3,5-ditertbutyl-4-acetoxybenzylidenemalononitrile, or α-cyano-3,5-tert-butyl-4-hydroxycinnamic acid methyl ester; 1,3,6,8-tetranitrocarbazole, 2,6-dihydroxyl,1,1,7,7,7-hexafluoro-2,6-bis (trifluoromethyl)-heptanone-4-[bis(hexafluororoacetonyl)acetone]; free fatty acids, such as long chain aliphatic monocarboxylic acids, n-tetradecanoic acid [myristic acid], or cis-9-octadecenoic acid [oleic acid]; phenols, such as 4-chlorophenol, 2,4,6-trichlorophenol [TCP], 2,4,6-tribromophenol, pentachlorophenol [PCP], 4-nitrophenol, 2,4-dinitrophenol [DNP], 2,6-dinitrophenol [2,6-DNP], 4-isobutyl-2,6-dinitrophenol, 4-isooctyl-2,6-dinitrophenol, 4,6-dinitrocresol, or 2-azido-4-nitrophenol; phenylanthranilic acids, such as N-phenylanthranilic acid, N-(3-nitrophenyl)anthranilic acid, N-(2,3-dimethylphenyl)anthranilic acid [mefenamic acid], N-(3-chlorophenyl)anthranilic acid, or N-(3-trifluoromethylphenyl)anthranilic acid [flufenamic acid]; 2-(phenylhydrazono)nitriles, such as carbonyl cyanide phenylhydrazone (phenylhydrazonomalononitrile) [CCP], carbonyl cyanide 3-chlorophenylhydrazone [m-Cl-CCP;CCCP], carbonyl cyanide 4-trifluoromethoxyphenylhydrazone [p-CF$_3$O-CCP;FCCP], carbonyl cyanide 4-(6'-methyl-2'-benzothiazyl)phenylhydrazone [BT-CCP], the methyl ester of phenylhydrazonocyanoacetic acid, the methyl ester of (3-chlorophenylhydrazono)cyanoacetic acid, 2-(3'-chloro-phenylhydrazono)-3-oxobutyronitrile, 2-(2',4-dinitrophenylhydrazono)-3-oxo-4,4-dimethylvaleronitrile, or 2-[3',5-bis(trifluoromethyl) phenylhydrazono]-3-oxo-4,4-dimethylvaleronitrile; salicylanilides such as salicylanilide, 2',5-dichloro-4'-nitrosalicylanilide [S-3], 4',5-dichloro-3-(p-chlorophenyl)salicylanilide [S-6], 2',5-dichloro-3-(p-chlorophenyl)-5'-nitrosalicylanilide [S-9], 2',5-dichloro-3-tert-butyl-4'-nitrosalicylanilide [S-13], 3,5-dichlorosalicylanilide, 3,5-dichloro-4'-methylsalicylanilide, 3,5-dichloro-4'-nitrosalicylanilide, or 3,4',5-trichlorosalicylanilide [DCC]; tribromoimidazole [TBI]; trifluoromethylbenzimidazole, such as 2-trifluoromethylbenzimidazole [TFB], 5-chlorotrifluoromethylbenzimidazole [CTFB], 4,5-dichlorotrifluoromethylbenzimidazole, 4,7-dichlorotrifluoromethylbenzimidazole, 4,5,6-trichlorotrifluoromethylbenzimidazole, 4,5,6,7-tetrachlorotrifluoromethylbenzimidazole (TTFB), 4-(2-chlorophenylhydrazono)-3-methyl-5-isoxazolone, 3-acetyl-5-(4-fluorobenzylidene)-2,5-dihydro-4-hydroxy-2-oxothiophene, 2-amino-1,1,3-tricyano-1-propene, n-decylamine, anilinothiophenes, such as 2-(2,6-dimethylanilino)-3,4-dinitro-5-chlorothiophene [DDCT], or 2-(4-chloroanilino)-3,4-dinitro-5-bromothiophene [BDCT], arsenate ion, arsenite ion, cadmium ion, 2-chloro-5-nitrobenzyldidenemalononitrile, decachloro-1,2-carborane [decachlorobarene], desaspidin, diethylstilbestrol [DES], gramicidin D, merphalan (sarcolysine), thyroxine, tetraphenylboron ion [TPB], trialkyltin ion, tributyltin ion, and valinomycin.

As discussed previously, supra, for appropriate clinical use in the present therapy system, an O/P uncoupling agent must not only be capable of producing an adequate degree of uncoupling action to achieve desired therapeutic levels of oncolysis, but must also be substantially free of any detrimental, toxic, or otherwise significantly undesirable side effects, and must also be physiologically tolerable by the patient in order to be used in the therapy treatment of this invention.

High $pK_a$ Uncoupling Agents

Most UA, particularly those of the so-called "classical" group [Heytler, P. G. *Inhibitors of Mitochondrial Functions* (p.203) Pergamon Press, New York (1981)] are acids which dissociate, or ionize, in solution. As is well known pharmacodynamically, the total concentration of such agents in a cell (i.e., the concentration of the dissociated anionic moiety plus the concentration of the undissociated molecule) is dependent upon the pK of the UA molecule and the extracellular pH and intracellular $pH_L$ of the cell, for a given extracellular total UA concentration. (The $pK_a$ is the negative of the logarithm of the acidic dissociation constant Ka of the molecule.) For a given $pK_a$ UA, the total concentration of UA in the cell decreases as the intracellular pH decreases, in accord with the Henderson-Hasselbalch relation [e.g., see Goodman, L. S. et al. (Ed.) *The Pharmacological Basis of Theraoeutics*, 5th Ed., Ch. 1, Macmillan Pub. Co., New York (1975)]. The effectiveness of a given intracellular pH change in reducing the total UA concentration in the cell depends very much on the $pK_a$; UA with smaller $pK_a$ constants are much more susceptible to being moved out of the cell (i.e., decrease in total UA concentration) as the intracellular pH decreases than UA with relatively high $pK_a$ values (e.g., $pK_a \geq 7$).

For example, a cancer cell that has a given initial total concentration of an UA with a $pK_a=4.0$ and an initial intracellular pH=7.0 will have that concentration reduced by 89.9% if the intracellular pH decreases to 6.0 due to acidity buildup in the cell. The desirable uncoupling action of the UA will thus be reduced steadily in the cancer cell as it becomes increasingly acid, until at pH=6.0 only about 10% of the initial uncoupling (i.e., AAD) activity remains. Since the UA concentration variation is logarithmically related to the pH change, even small decreases in intracellular pH can produce relatively large changes in UA concentration, and hence in O/P uncoupling activity. Thus, a cancer cell that has a given initial total concentration of an UA with a $pK_a=4.0$ and an intracellular pH=7.0 will have that concentration reduced 50% if the intracellular pH decreases by only 0.3 of a pH unit. The uncoupling activity in the cancer cell would thus be reduced by 50% by the relatively small pH change in going from pH=7.0 to pH=6.7, for an UA with a $pK_a=4.0$. This means that much or most of the O/P uncoupling effectiveness in the cancer cell, with a UA having a $pK_a=4$ used as the AAD, would be lost as the cell becomes progressively more acid, as is particularly the case when the UA (as the AAD) is used in combination with a LEB. This loss of uncoupling activity acts in turn to decrease the pH decline per se, so that a point may ultimately be reached by the cancer cell when no further decrease in pH can occur, whence the desired $pH_L$ cannot be reached, even with both the UA and the LEB present. The result of using a low $pK_a$ UA as the AAD, therefore, could be in some cases that the cancer cells experience only a small fraction of the uncoupling activity simultaneously experienced by the normal cells of the body, which do not become acid. The resultant clinical situation would then be one wherein the body is at the maximum tolerable metabolic rate permissible with the low $pK_a$ UA, but the cancer cells simultaneously are not experiencing enough uncoupling to reach the $pH_L$ level, whence cancer cell death does not occur, although cancer cell proliferation may be arrested. As has been experienced clinically, the same situation might maintain also in cases where a LEB is not utilized, but the cancer cells still become sufficiently acid to peg the maximum uncoupling activity that is attainable, whence $ATP_A ATP_L=$(death by energy starvation) cannot be attained. These adverse potentialities are entirely precluded by use of acidicly dissociable UA with relatively large $pK_a$ values, substantially $pK_a \geq 7$. At $pK_a$ values above about 7, the sensitivity of the intracellular UA concentration to physiologically expectable intracellular pH changes (i.e., $5.5 \leq pH \leq 7.5$) becomes increasingly smaller as the $pK_a$ increases, reaching practically zero at $pK_a=9.0$ and above.

Consequently, regarding the use of ionically dissociable UA as AAD in the present invention, most especially when they are used in combination with the LEB thereof to effect a lethal pH depression, it is desirable, advantageous, and preferred to utilize those acidicly dissociable UA which have a $pK_a$ substantially in the range of $pK_a \geq 7$. More generally, in the case of any acidicly or ionically dissociable molecule used as an AAD under the present invention, it is preferred that such molecule have a $pK_a$ substantially in the range $pK_a \geq 7$. Most generally, in the case of any substance, means or procedure used as an AAD under the present invention, it is preferred that such substance, means or procedure be substantially insensitive, in respect to its ATP-availability depressing action, to changes in the intracellular pH, in order to obtain maximal oncolytic efficacy.

Examples of high $pK_a$ uncoupling agents, together with their respective $pK_a$ values, include but are not limited to the following: 4-nitrophenol (7.01); 4-chlorophenol (9.18), phenylhydrazonocyanoacetic acid, methyl ester (8.40); (3-chlorophenylhydrazono) cyanoacetic acid, methyl ester (7.70); 5-chlorotrifluoromethyl benzimidazole (8.9).

(2) Agents which result in wasting (hydrolysis) of ATP that is already synthesized include but are not limited to (a) Inappropriate stimulation of endogenous cellular ATPase activity: Thyroid hormone (see definition of TH, infra); Protein restriction/restoration cycling (see Example 14, infra).

(b) Exogenously supplied enzymic ATPases and Phosphohydrolases: ASFV ATPase; Azotobacter adenylate kinase; Molybdenum-Iron Protein (*Klebsiella pneumoniae*); recA Protein (*E. coli*).

(c) Exogenously supplied nonenzymic ATPases and chemical hydrolyzers: Perchloric acid.

Thyroid Hormone

Thyroid hormone (TH), for use as an AAD and/or AAB of the present invention, is defined as comprising $T_4$ (thyroxine) and/or $T_3$ (triiodothyronine), in any clinically appropriate form and proportion, and from any clinically appropriate source. It is generally held, pharmacologically, that the active form of thyroid hormone is $T_3$, and that the $T_4$ provided by the thyroid gland is ultimately converted to the active $T_3$ form. Consequently, in the present therapy, TH may be $T_4$ and/or $T_3$, or appropriate sources thereof, such as thyroglobulin or dessicated thyroid gland powder. For TH dosing purposes, the pharmacological convention of relating $T_4$, $T_3$, and $T_4+T_3$ metabolic-effectiveness equivalents to that of 1.0 grain of dessicated thyroid gland powder is followed herein. One grain of dessicated thyroid gland powder contains 50 μg of $T_4$ and 12.5 μg of $T_3$, and in metabolic effectiveness 1.0 μg of $T_3$ is equivalent to 4.0 μg of $T_4$.

(3) Agents which inhibit ATP participation in cellular energy transfer metabolic reactions:

(a) Metabolically competitive analogs of ATP including but not limited to: Adenylyl imidophosphate; adenylyl methylenediphosphate; 2-chloroadenosine; adenosine 5'-ethylcarboxamide; 1-methylisoguanosine; adenosine tetraphosphate; 3'-arylazido-ATP.

(b) Agents which foster abortive energy transfer in ATP reactions including but not limited to: Phenylalanyl-tRNA-synthetase+Phenylalanine+Zn++.

(c) Agents which bind to and energetically inactivate ATP including but not limited to: Chelate formation with Pseudomonas Membrane Protein.

In general, it is advantageous and most preferred in the clinical practice of the present therapy system to include for use as the AAD at least one agent which wastefully hydrolyzes or energetically inactivates already-made ATP (as in (2) ane (3) above), and which additionally is insensitive to intracellular pH when the LEB is used with the AAD. The reason for this inclusion is that such AAD agents are effective in depressing $ATP_A$ deriving from ATP made via O/P and glycolysis, whereas UA (as in (1) above) can depress $A\dot{T}P_A$ only to the extent of ATP deriving from O/P alone. Consequently, UA alone could not appreciably depress $A\dot{T}P_A$, for example, in cancer cells whose ATP production was derived in major proportion from glycolysis per se, whereas wasteful hydrolyzers and inactivators of already-made ATP could readily effect the desired $ATP_A$ depression in such cells, as well as in cells subsisting primarily on O/P-derived ATP prior to therapeutic intervention. Utilization of a combination of a high $pK_a$ UA with an ATP-hydrolyzing agent and/or ATP-inactivating agent as the AAD has the clinical benefit of providing maximum overall AAD effectiveness while reducing the level of administration of both agents, compared to that required when either agent is used alone as the AAD.

Lactate Export Blocking Agents (LEB)

The purpose of the LEB in the present therapy system is to limit the maximum rate of export of lactic acid from the cancer cells, to such an extent that the AAD-mediated increase in lactate production rate $LAC_p$ can lead to a buildup of lactate in the cancer cells sufficient to produce a lethal intracellular pH. Although some early studies indicated the existence of lactate export inhibition properties of certain agents [Harold, F. M. et al., *J. Bacteriol.* 117 1141 (1974); Halestrap, A. P. et al., *Biochem. J.* 148, 97 (1975); Henderson, A. H. et al., *Am J. Physiol.* 217 1752 (1969); Lamers, J. M. et al., *Biophys. Acta* 394, 31 (1975); Watts, D. J. et al., *Biochem. J.* 104 51P (1967)], the first comprehensive study of a cancer cell form with a blocking agent was performed in vitro with the bioflavonoid quercetin [Spencer, T. L. et al., *Biochem. J.* 154, 405 (1976)]. Examples of some forms of LEB include but are not limited to the following:

(1) General chemical substances demonstrating $LAC_E$ inhibition in cancer cells: 4,4'-bis(isothiocyano)-2,2'-stilbenedisulfonate; isobutylcarbonyl lactyl anhydride; α-cyano-4-hydroxycinnamate; α-cyano-3-hydroxycinnamate, DL-p-hydroxy-phenyl-lactate and mersalyl.

(b) Bioflavonoids demonstrating $LAC_E$ inhibition in cancer cells: 5,7,4'-Trihydroxyflavone (apigenin); 3,7,3',4'-quadrahydroxyflavone (fisetin); 3,5,7,2',4'-pentahydroxyflavone (morin); 3,5,7,3',4'-pentahydroxyflavone (quercetin); 5,7,4'-trihydroxy-3,6-OCH$_3$-flavone (K3); 5,7,3'-trihydroxy-3,6,4'-OCH$_3$-flavone.

The naturally occurring plant bioflavonoids, common in many food products, are a preferred class of LEB for use in the present therapeutical system. The bioflavonoid quercetin (3,5,7,3',4'-pentahydroxyflavone) is currently the most preferred LEB for use in the present therapy system, being the most effective (on a weight basis) of the bioflavonoids in regard to producing lactate export inhibition in cancer cells, as well as having a clinically demonstrated absence in the present therapy system of toxicity and untoward side effects at therapeutically effective doses in human cancer patients (see, e.g., Examples through 4, infra). Quercetin exerts its inhibitory action by binding to and deactivating the molecular moieties specifically responsible for the transport of lactate through the pericellular membrane [Spencer, T. L. et al. (1976), supra]. Moreover, quercetin has been demonstrated to exert a remarkable inhibitory influence in blocking mammalian malignant neoplasm promotion by a variety of carcinogenic agents [e.g., Kato, K. et al., *J. Toxicol. Sci.* 9, 319 (1984); Kato, K. et al., *Ecotoxicol. Environ. Safety* 10, 63 (1985); Kato, K. et al., *Carcinooenesis* 4 1301 (1983); Levy, J. et al., *Biochem. Biophys. Res. Commun.* 123, 1227 (1984); Nishino, H. et al. *Oncology* 41, 120 (1984); Nishino, H. *Gann* 75, 113 (1984); Hirose, M., *Cancer Lett.* 21, 23 (1983)]. It has also been shown to possess a potential antimetastatic action in mammals [e.g., Ishikawa, M., *Int. J. Cancer* 15, 338 (1987)].

Combinations of the Metabolic Effectors

The most fundamental metabolic effector of the present invention is the AAD, most preferably AAD substantially insensitive to therapeutically induced intracellular pH decreases in the cancer cells. At adequate levels of administration, the AAD alone is capable of effecting very significant rates and extents of oncolysis (see, e.g., Example 14, infra), albeit with quite high concomitant elevation of the patient whole-body resting metabolic rate. The AAD-alone regimen effects cancer cell death by depressing the $A\dot{T}P_A$ to the lethal $A\dot{T}P_L$ level, i.e., by imposing energy starvation. The LEB is the second most fundamental metabolic effector but, as emphasized previously herein, must be used in combination with the AAD in all cases to be therapeutically effective. With the AAD-LEB combination oer se. cancer cell death is effected by a buildup in intracellular acidity to a point where a lethal $pH_L$ level is reached (see Examples 3 and 4, infra). With the AAD-LEB regimen, the required level of AAD to achieve cancer cell death is decreased relative to the AAD-alone regimen, but may still be appreciable, particularly if the cancer cells have a very high O\P-ATP production rate capability that must be overcome by the AAD, whence the patient wholebody resting metabo)ic rate elevation may still be quite high during treatment. Addition of the metabolic effectors DNR and/or FAB and/or AAB to the AAD regimen serves to decrease the maximum rate at which NADH can be supplied to the RC of the cancer cells (by limiting FA and AA availability for the CAC), and hence commensurately decreases the level of AAD action required to effect oncolysis. This lowered AAD requirement is quite beneficial clinically in that a commensurately lower patient whole-body resting metabolic rate then exists at the AAD level where very significant oncolysis maintains. Thus, while very significant oncolysis can be effected with the AAD-alone regimen and with the AAD-LEB regimen with adequately strong AAD, each regimen can be significantly clinically benefited in terms of permitting a lowered patient whole-body resting metabolic rate elevation by coadministering with them one or more of the DNR, FAB and AAD metabolic effectors. Moreover, they permit attainment of very significant oncolysis clinically with relatively "weak". AAD which otherwise might not be able to depress $\dot{ATP}_A$ adequately at their clinically maximal administration levels. Maximal benefit in this respect is of course obtained by coadministration of the full DNR-FAB-AAB combination in each case. Consequently, the most preferred clinical regimen of the present therapy system is the coadministration of all five metabolic effectors in the combination AAD-LEB-DNR-FAB-AAB.

Most Preferred Embodiment

Although the AAD-alone or the AAD-LEB alone at adequate strength are per se capable of effecting pronounced oncolysis, it is most preferred to utilize the concurrent administration of AAD, LEB, DNR, FAB and AAB.

Although the concurrent administration of the overall combination of all five of the basic metabolic effectors AAD-LEB-DNR-FAB-AAB is considered the most preferred embodiment of the present therapy system for clinical purposes, it must be clearly emphasized that the AAD-alone or the AAD-LEB alone at adequate strength are per se fully capable of effecting pronounced oncolysis. However, the concurrent administration of the DNR, FAB and AAB, singly or in combinations, with the AAD or with the AAD-LEB serves to lower the rate of availability of NADH to the RC in the cancer cells, and hence to lower the maximum rate at which ATP can be produced via the RC. Consequently, with the coadministration of the DNR and/or FAB and/or AAB with the AAD or with the AAD-LEB, the amount of AAD action required to achieve cancer cell death by $\dot{ATP}_L$ or $pH_L$, respectively, is significantly lowered. This lowering of the required AAD is of appreciable clinical advantage, since with a lower AAD level the patient experiences a commensurately lower whole-body resting metabolic rate elevation during treatment. Additionally, with the coadministration of the DNR and/or FAB and/or AAB, very significant oncolysis can be achieved with AAD that have relatively weak maximal depressor action levels, levels that may be inadequate to effect oncolysis when the AAD or AAD-LEB are used alone. Moreover, very significant oncolysis can be achieved at much lower AAD levels in cancer patients having particularly elevated plasma-free fatty acid and amino acid levels due to disease-fostered stress, when the DNR-FAB-AAB is coadministered with the AAD or the AAD-LEB. Thus, although the primary metabolic effectors AAD and AAD-LEB can be used alone at adequately strong levels to effect significant oncolysis, their efficacy is successively enhanced and the whole-body metabolic rate elevation lowered by the coadministration of one or more of the "adjuvant" metabolic effectors DNR, FAB and AAB.

ILLUSTRATIVE THERAPY SYSTEM FOR HUMAN PATIENTS

The following clinical protocol represents a typical administration regimen for implementing the therapy system of the present invention for human cancer patients. Moreover, it constitutes a most preferred embodiment of the present therapy system, one that is particularly suitable for (otherwise) terminal cancer patients for which other treatment modalities have failed. This particular regimen and its combination of specific therapeutical metabolic effectors is exceptionally simple to administer and is free of untoward side effects, allowing it to be utilized with far advanced patients having severe debilitation from their disease and from prior treatment with such modalities as mitoxin chemotherapy and radiotherapy.

The regimen is composed of two clinical phases, administered sequentially. Phase I consists of the administration of the therapy system at a hospital or clinic on an in-patient basis. The duration of Phase I generally ranges from two to four weeks. Upon completion of Phase I, the patient enters Phase II, which consists of a continuation of the same therapy regimen but on an out-patient basis. The duration of Phase II is variable, depending upon the rate of patient responsiveness; treatment is continued as long as the malignant condition is being effectively regressed or controlled.

Phase I

In Phase I, the patient enters the hospital and first receives a thorough physical examination along with complete laboratory tests (i.e., "SMAC-24" or equivalent, with hematology, blood chemistry, enzymology, serology and urinalysis) to rule out the existence of any prohibitively contraindicatory condition or conditions. The therapy is then initiated as soon as the laboratory test results are available and evaluated. The following therapeutical metabolic effectors are administered:

(1) DNR: The patient's resting metabolic rate ($lO_2/d$) is measured at the start of the therapy, and this result is adjusted for physical activity (e.g., by increasing the resting metabolic rate value by 10% to 5%, depending upon the level of activity of the particular patient), to establish the active metabolic rate. The effective metabolic rate is then determined as one-half of the sum of the resting metabolic rate and the active metabolic rate. The total $lO_2/d$ of the effective metabolic rate is converted to its equivalent in Kcal/d of carbohydrate (powder) by multiplying by 5.426 Kcal/d g/d per Kcal/d. One percent of the carbohydrate caloric value is provided as essential fatty acids (0.108 g of essential fatty acids per Kcal). Protein (e.g., casein or egg protein powder) is provided, nominally, at a level of 15 to 20 g/d per 70 Kg of body weight. These ingredients are blended into a suspension along with an appropriate level of vitamins and minerals (as previously described). The DNR is then dispensed to the patient in several nutrient cocktails at intervals over the day. When required, the equivalent DNR can be partially or wholly furnished in appropriate intravenous form parenterally. The effective metabolic rate is determined periodically (daily or weekly) thereafter, and the result used to adjust the DNR to the measured caloric level, to appropriately accommodate such changes in the metabolic rate as may occur during the treatment period of Phase I.

(2) FAB: The FAB in this therapeutical protocol is lente insulin (18–20 hr duration) and is administered by intramuscular injection once per day (at approximately 9:00 AM) at a dose of 10 to 20 I.U., nominally. Prior to such insulin administration, the blood glucose level is determined by use of a drop of blood and conventional glucose test strips available for that purpose. Blood glucose levels may similarly be checked whenever desired. In general, with appropriate DNR levels or glucose intake, blood glucose concentration remains normal or slightly elevated in this insulin dose range. Insulin is, clinically, a particularly good FAB. Not only does it very effectively block FA mobilization from body adipose-cell stores, it also simultaneously aids in insuring a rapid rate of glucose transport into normal cells for energy use, and into cancer cells for maximizing the ΔGLY (for achieving maximal lethality with the LEB).

(3) AAB: In this therapy protocol, the AAB and the AAD are the same, namely thyroid hormone; see "AAD" below.

(4) AAD: The AAD in this therapy protocol is thyroid hormone. TH is administered in tablet form nominally at a dose rate of 1.0 to 3.0 equivalent grains (see definition of TH, supra) per day given orally at 8:00 AM. With higher doses of TH, significant increases in the resting metabolic rate may occur, whence appropriate adjustment of the DNR caloric input is required.

(5) LEB: The LEB in this therapy protocol is the bioflavonoid quercetin, provided in the dihydrate form. The additional potential antimetastatic and anticarcinogenic properties of quercetin have been cited previously herein. Quercetin is administered orally in capsule form, twice daily (at approximately 8:00 AM and 8:00 PM) at a nominal dosage level of 2.0 to 3.0 mg per Kg of body weight per capsule, of the pure (anhydrous) material. The maximum dosage of quercetin may be increased, if required. Quercetin is generally poorly absorbed in the intestinal tract, and elevated dosages may be necessary in particular cases to ensure attainment of adequate plasma levels.

During Phase I, the DNR, FAB (lente insulin), AAD and AAB (thyroid hormone), and LEB (quercetin) are concurrently administered each day at their prescribed times and doses. The first DNR nutrient cocktails are given at 8:00 AM each day and thyroid hormone tablets are given concomitantly. The insulin injection is given one hour later, to allow time for glucose assimilation prior to the insulin administration. Blood glucose measurements, using simple chemical test strips and a drop of blood, are made each morning to insure that the glucose level is adequate, prior to the insulin administration. The body weight is measured daily to insure maintenance of steady weight by increasing or decreasing the daily caloric intake of the DNR. Additionally, the effective metabolic rate may be determined periodically to establish the precise DNR caloric intake requirements under the actual treatment conditions. Laboratory tests, as previously described, are done weekly, to monitor the hemapoietic, electrolyte and enzymic parameters. The adequacy of plasma-free fatty acid depression by the insulin (FAB) can be monitored by use of the plasma creatine phosphokinase (CPK) concentration, if desired. Levels 5% to 10% above the normal CPK range maximum are indicative of effective free fatty acid availability control. The patient may engage in a normal level of activities, but should not over-exert during this period, particularly when the metabolic rate is somewhat elevated. I all is going well with the patient in three to four weeks, the patient proceeds to Phase II (outpatient phase).

Phase II

In Phase II, the outpatient phase, the patient remains on precisely the same therapeutical protocol as in Phase I. However, for variety, the carbohydrate, protein, and essential fatty acids of the DNR may be supplied by regular food items rather than by the dehydrated carbohydrate and protein powders and oils served in suspension form. The food diet may be supplemented with the Phase I type of DNR nutrient cocktails if desired. The patient returns to the clinic or hospital at periodic intervals (every two to three weeks initially) for physical checkups, laboratory tests, and tumor-status evaluations. The patient is continued in Phase II until clinically free of their specific malignancy or for so long as the malignancy remains under control. Concurrently, the patient proceeds with his normal lifestyle and activities.

The foregoing illustration of a typical but specific clinical protocol according to the most preferred embodiment of the present invention demonstrates the essential features thereof and the simplicity of its administration. However, it is understood that the phasing and duration of treatment periods therein are arbitrary, depending on the particular patient and the specific clinical status and condition. Thus, in particular cases, Phase II may constitute the entire treatment program, Phase I being unnecessary. Similarly, the treatment may be interrupted for intervals at any point. Additionally, as emphasized previously herein in the section "Combinations of Metabolic Effectors," supra, in particular cases only the AAD-alone or the AAD-LED combination alone, or either of these regimens in combination with one or more of the DNR, FAB and AAB metabolic effectors, may be administered.

The present therapy system may readily be given concurrently, to appreciable clinical advantage in certain cases, with other cancer treatment modalities presently practiced. For example, full administration of the present therapy system concurrently with a protocol of mitoxin chemotherapy adds a third individual mode of cancer cell destruction, while allowing a pronounced reduction in the toxic and debilitating side-effects of the mitoxin modality by permitting use of smaller doses of the mitoxic drugs. A similarly efficacious result can be obtained from the use of the present therapy system concurrently with oncological radiotherapy, immunotherapy or hyperthermotherapy, in appropriate cases. Moreover, in appropriate cases the present therapy system, as has been demonstrated clinically, can be used to reduce advanced but localized malignant lesions to a size and extent that oncological surgery, including laser surgery and cryosurgery, may be advantageously used, thereby effecting a rapid and complete final removal of a previously inoperable lesion.

In general, the dosage level of each metabolic effector in the present therapy system lies between the minimum required to effect oncolysis and the maximum at which it causes untoward or toxic side-effects in the particular patient.

It should be further noted that, while the foregoing therapeutic principles described herein are directly applicable to humans and other mammals with comparable resting metabolic rate levels, i.e., other primates, specific adaptation of this invention to mammals (and indeed other vertebrates) with significantly higher or lower resting metabolic rates is within the scope of this invention. It can, using the principles herein described, be effected by those skilled in the requisite technology without departing from the invention. It is indeed contemplated that the therapy system of the invention, with suitable adaptation to take account of the resting metabolic rate of the animal to be treated, such as to maintain daily caloric balance, will be particularly useful in the treatment of malignant neoplasms and conditions in valuable agricultural animals, pets, zoo animals, race horses, other pedigreed stock, and the like.

EXAMPLES OF CLINICAL EFFECTIVENESS OF METABOLIC EFFECTOR MALIGNANCY THERAPY ACCORDING TO THIS INVENTION

In Examples 1 and 2, infra, patients with totally different cancer types (i.e., different malignant cell phenotypes and body tumor sites) were identically treated according to Phase I and Phase II of the "Illustrative Therapy System for Human Patients" of the detailed description, supra, comprising the most preferred embodiment of the present invention. In these patient cases, the specific metabolic effectors used were: DNR, FAB (lente insulin), AAB (thyroid hormone), AAD (thyroid hormone), and LEB (quercetin). In these example cases, the AAD and AAB were co-supplied by the same agent, thyroid hormone. The results of these two cases demonstrate the pronounced oncolytic effectiveness of the present invention when all five basic metabolic effectors are used concurrently in synergistic combination, and when the AAD employed is insensitive to intracellular pH changes.

EXAMPLE 1

Example Case No. 1:
Female, 57 years old.
Diagnosis:
Recurrent infiltrating ductal cell carcinoma of the breast; terminal inflammatory stage.
Basis of Diaonosis:
Multiple specimens and histological analyses from excised malignant tumor of right breast.
Therapy Prior to Present Treatment:
Surgery (tumorectomy), extensive radiotherapy (4000 rads), and intensive mitoxin chemotherapy (Cytoxan). Patient had been asymptomatic for nearly three years, following initial treatment.
Tumor Status at Start of Present Treatment:
Right breast significantly swollen and enlarged; rigid, immobile, and painful. Breast has numerous pinkish indurated tumor nodules protruding slightly above skin surface, more frequent in number towards the areola. Areola and periareola area of breast contains many dark tumor nodules; areola is practically covered by thick, merging cancer nodules. Nipple is three-fourths retracted into breast. Breast exhibits marked hyperthermia (temperature elevation) relative to normal left breast. Intense, indurated inflammation area exists in band around breast extending back three inches from edge of areola. A broad area of highly inflammatory involvement extends from the breast over the right thorax, up to right axilla. Left breast is unaffected. A large (5 cm diameter), hard, firmly fixed mass is located in the right axilla; patient cannot lift arm upward from side or lower it completely to side because of axillary tumor involvement. Patient is very apprehensive, but in good general physical condition. Body weight is essentially normal for sex and height. Elevated serum cortisol level of 20 $\mu$g/dl typical of advanced, highly stressed cancer patients.
Treatment Conditions (Phase I):
DNR: Nutrient cocktails
FAB: Lente insulin (10 I.U./d)
AAB: (co-provided by the AAD)
AAD: Thyroid hormone: Thyrolar 1, Armour (2.0 tablets/d)
LEB: Quercetin (1.5 mg/Kg twice per day)
Response to Treatment (Phase I):

Day 10 (Day number denotes number of days since beginning of treatment of patient with present protocol): Extensive elevation and induration of inflammation areas on right thorax and on right breast greatly diminished throughout; skin approaching normal appearance. Previous nodules on breast are disappearing; no new nodules have formed. Large dark nodules in and around areola are strongly suppurating a pale yellow fluid around edges of nodules; the smaller dark nodules appear to be drying out and forming blackish crusts or scabs. Axillar mass is softer to palpation, somewhat smaller, still fixed but not as firmly as initially. Hyperthermia of right breast still considerable. Resting metabolic rate over past 10 days has averaged 1.4 times the patient's standard basal metabolic rate (i.e., Mayo standard basal metabolic rate for her height, weight, sex and age; see U.S. Pat. No. 4,724,234). All laboratory results (i.e., SMAK-24 and urinalysis) normal; cortisol level 12 $\mu$g/dl, having decreased from the 20 $\mu$g/dl level at start of therapy. Weight has increased slightly since Day 1. Patient feels fine; free of any side effects; takes daily walks. All tumor progression arrested; generalized, significant tumor regression in progress.

Day 20: Induration and elevation of former inflammation area on right thorax completely gone; skin is flat, smooth and dry, with brownish pigmentation. Periareola inflammation area now flat, smooth, but still reddish (inflamed). All previous tumor nodules on right breast have disappeared; no new nodules have formed since Day 1. Several of the smaller areola and periareola "scabs" have fallen off; skin beneath appears perfectly normal when viewed under magnification. Larger areola crusts (scabs) are still suppurating; scabs are very hard and firmly adhered to skin surface. Attending medical oncologist feels that "scabs" are dead or dying surface cancerous nodules and will all eventually dry out and fall off when oncolysis is complete. Axillar mass greatly diminished in size; now 2 cm in diameter, a 70.3% reduction in the original tumor mass; now free of chest wall and fully movable; soft. Patient's arm is fully mobile again; can lift right arm over head and hold it flat by side without any difficulty. Hyperthermia of right breast is hardly discernable by touch. Breast is much less swollen; is soft and movable, no longer rigid; not as painful, but remains tender. The resting metabolic rate has averaged approximately 2.0 times the standard basal metabolic rate over the preceding 10 days. All laboratory results are normal; cortisol level still lower, down to 8 $\mu$g/dl. Weight has remained constant during past 10 days. Oncologist says patient in excellent condition physiologically and psychologically. All tumor progression fully arrested, and patient appears clinically free of tumor except for large areola scabs where continuing suppuration indicates still ongoing tumor lysis.

Day 30: Area of periareola inflammation now gone; skin is flat, smooth, and dry; characteristic brownish pigmentation remains. No new tumor nodules have appeared since Day 1. Many more of the blackish scabs in the areola and periareola region of the right breast have fallen, leaving normal skin underneath. Interestingly, there are no depressions or scars left in the region where the tumor nodules have been. Microscopically, the fallen scabs appear to be hard, black shells which covered the local surface tumor masses during oncolysis. Although several scabs remain, only the two larger ones covering the site of the tumorectomy incision have suppuration from time to time, indicative of continuing oncolysis. Breast is fully normal, soft, movable, nonpainful. Previously retracted nipple has egressed out of breast and is now fully normal in size and disposition. No discernable hyperthermia of right breast relative to normal left breast. Axillar mass has decreased further in size, and has resolved into two distinct, palpable lymph nodes. The resting metabolic rate over the past 10 days has averaged 2.0 times basal. All laboratory results normal; cortisol 8.5 μg/dl. Body weight has remained constant. Overall condition of patient remains excellent. Patient continues to take daily walks and is normally active for her age.

Day 40: Nothing has changed significantly from Day 30. A few more dark scabs have fallen from the areola and periareola area of the breast. The two large scabs covering the initial incision continue to have slight suppuration around their margins, but appear to be dryer and harder. Interestingly, the overall regression pattern appears as one in which oncolysis begins simultaneously throughout all of the tumor region, but in which the first recurrent masses (i.e., along the initial tumorectomy incision) take the longest time to eradicate, this despite the fact that the now-normalized axillar mass was initially many-fold larger than the combined peri-incisional surface masses. Laboratory results are normal and weight has remained constant. Patient remains in excellent condition and is asymptomatic.

Day 47: Patient leaves hospital to enter the outpatient treatment stage of Phase II. In Phase II, the patient will resume her normal lifestyle activities but will report back to the attending oncologist at frequent intervals for laboratory tests and physical examinations. The medication schedule will remain exactly the same as in Phase I. The DNR will remain calorically the same, but will be from regular food items, rather than from the Phase I nutrient cocktail suspensions.

Response to Treatment (Phase II):

Day 75: Patient has been on out-patient regimen for 28 days. Treatment protocol has remained exactly the same as in Phase I, except the DNR carbohydrate, protein, and essential fatty acids are provided by normal food items, for palative reasons. Patient's disease remains fully arrested; oncologist reports patient clinically free of discernable tumor activity. All previous inflammation areas are flat and smooth. The two largest scabs at the initial incision site have come off, revealing fully normal skin underneath; the initial incision scar in the areola which they covered is now fully visible. Only a relatively few scabs remain, mostly in the periareola area. These exhibit no suppuration and appear hard and dry. Patient's blood and urine parameters have remained normal and weight constant. Patient has continued usual household activities and lifestyle with no problems; is in excellent condition.

Day 109: Five days after previous examination on Day 75, patient became severely ill with influenza during a vacation trip, and went off the therapy regimen for 14 days. After nine days of being off the regimen and during the height of stress of her illness, two small scabs remaining in the periareola region came off and the red areas beneath began to enlarge and become peripherally inflamed. Following a return to the therapy protocol on Day 94, the inflammation gradually disappeared and the areas became covered over with exactly the same form of blackish scab as seen with lesions in the initial days of the treatment in Phase I; moderate suppuration ensued. These scabs were still present on Day 109, but were free of suppuration, hard, and dry. The patient lost several pounds of weight during the period of her illness, due to lack of food intake. Otherwise, she was in good health after the influenza episode.

Day 183 (six months): Patient was seen by attending oncologist at approximately tri-weekly intervals after Day 75. She has remained in good health and gained back most of the weight lost during her influenza illness. Her malignant disease remains fully arrested. Most of scabs have fallen, leaving normal skin underneath. Several scabs still remain, but appear hard and dry. Detailed examination by attending oncologist reveals no evidence of metastases. (It is germane to note here that another female patient with recurrent breast cancer, presenting to the oncologist at the same time as the present example patient, but in a less advanced disease state, was placed on intensive mitoxin chemotherapy. That patient succumbed approximately three months after resumption of mitoxin chemotherapy.) Present patient's blood and urinary parameters have remained normal, including estrogen level. Cortisol remains at a low level. Patient is in good psychological condition and continues an active lifestyle while remaining on the Phase II therapy regimen.

EXAMPLE 2

Example Case No. 2:
Female, 48 years old.
Diagnosis:
Far advanced basal cell carcinoma of the left face (naso-orbital-cheek area) of 1½ years duration; tumor invading nose, cheek, and left eye; large (1.5 cm diameter) central ulcerated crater.
Basis of Diagnosis:
Histological analyses of three biopsy specimens taken from the upper margins and floor of the open ulcer; all specimens demonstrated malignant keratinocytes (basal cells) disposed in numerous nests in dense fibrous stoma, and in pseudo-glandular arrangements.
Therapy Prior to Present Treatment:
Topical ointments and antibiotics supplied by dermatologist over 1½-year period, with no effect on lesion progression.
Tumor Status at Start of Present Therapy:
Tumor consists of a single, continuous mass extending laterally from the midline of the nose to the left for 4.25 cm and vertically from the left eyelid downward 4.0 cm. A deep, open, ulcerated cavity of approximately 1.5 cm diameter is centered over the point where the small initial "pimple" arose 1½ years ago. A very hard, rigid, fixed, continuous tumor mass, with well-defined margins as determined by palpation, extends under the ulcer and subcutaneously laterally and vertically as described. Skin immediately surrounding ulcer is intensely inflamed for a distance of 0.5 cm; no suppuration or drainage from ulcer currently being experienced by patient. Floor of ulcer bright red, except for black thrombus spots where biopsies were taken seven days previously. The tumor area is raised approximately 0.5 cm above the normal surface of the face, being particularly raised in the region near the eye and causing significant obscuration of the visual field when reading. Conjunctiva of left eye inflamed and irritated, but no obvious tumor invasion of eye orbit yet present. Left nostril is essentially completely closed internally from lateral compression by tumor mass. Xerographic x-ray study indicates tumor has not yet invaded any b one structures. Patient infrequently experiences slight pain in the ulcer region. Patient was referred to a plastic surgeon for treatment, but surgery was ruled out because of extensiveness of lesion and its location (eye, nose involvement); radiotherapy and topical mitoxin chemotherapy also considered untenable treatment modalities in view of patient's condition. Patient is in reasonably good general health, but is excessively obese (excess body weight above her standard body weight for sex and height is 106.4% of standard body weight). Patient has high blood pressure, poor cerebral circulation, moderate hyperglycemia, and is under great emotional stress from several causes.

Treatment Conditions (Phase I):
DNR: Nutrient cocktails
FAB: Lente insulin (15 I.U./d)
AAB: (co-provided by the AAD)
AAD: Thyroid hormone: Thyrolar 1, Armour (2.0 tablets/d)
LEB: Quercetin (1.5 mg/Kg twice per day)

Response to Treatment (Phase I):

Day 2: (Day number denotes number of days since beginning of treatment of patient with present protocol): Pronounced suppuration of pale yellow fluid from the ulcer commenced in the late afternoon and continued all night. Patient reports experiencing an intense "tingling" sensation throughout the entire tumor region. Patient readily consumes total daily DNR content, despite its large volume. Afternoon resting metabolic rate is 1.72 times patient's Mayo standard basal metabolic rate for her sex, age, height, and weight. (Hereinafter the resting metabolic rate is indicated only by its multiple in terms of the Mayo standard basal metabolic rate.)

Day 3: Ulcer crater is completely filled with semidry, yellowish seric material (like dried serum). Resting metabolic rate is now 1.76 times standard basal metabolic rate. Patient feels fine.

Day 5: Pronounced suppuration from ulcer has continued; is especially intense in afternoon and night. Tingling sensation at such times continues. Afternoon resting metabolic rate is 1.92; morning resting metabolic rate is appreciably lower than the afternoon rate, and suppuration in the morning proceeds at a much lower rate. Examination shows that the skin overlying the whole tumor area is now "angry red" with intense inflammation; especially over the area between the ulcer margin and the eye. The induration of this area also appears less and the ulcer diameter smaller. Laboratory test results (blood parameters and urinalysis) all normal, including glucose level.

Day 7: Resting metabolic rate reached 2.13 yesterday afternoon and was accompanied by pronounced afternoon, evening, and night suppuration, along with increased intensity of "itching" and "tingling" over entire tumor region. Increased intensity of suppuration in afternoon closely correlates with increased afternoon elevation in resting metabolic rate level, as well as increase in afternoon metabolic rate level from day to day. Correspondingly, the intensity of tingling and itching correlates directly with the measured resting metabolic rate level. Patient reports that she can no longer discern any tumor protrusion into her reading visual field. Detailed palpation measurements of tumor size by the attending oncologist indicate a pronounced reduction in all dimensions; tumor consistency throughout has become appreciably softer. Measurements by oncologist indicate a 60% reduction in overall tumor mass (volume) in 6½ days on clinical protocol. Maximum elevation of mass is now less than 0.3 cm at any point. These measurements correlate well with the general visual assessment of the tumor region indicating that the tumor region has shrunken noticeably, including the degree of protrusion above the normal surface level of the face. The impression is that the entire tumor mass is shrinking back towards the original ulcerative epicenter; the ulcer diameter itself has decreased 17% and its margins have become flatter. The increased softness in the tumor consistency is indicative of oncolysis throughout the tumor mass, as evidenced by the fact that the ulcer crater quickly becomes filled with yellow seric fluid upon pressing down upon the tumor mass at practically any point. Intranasal examination of the left nostril indicates a pronounced decrease in the former constriction by tumor-imposed external compression; patient reports she now breathes normally through this nostril. Patient doing well generally, but reports periods of "shortness of breath" and resultant anxiety when resting metabolic rate is significantly elevated (that is, >2.0). Patient continues to consume all of daily DNR.

Day 9: Skin over tumor mass continues to remain inflamed, but inflamed area is much smaller than initially, extending out from the ulcer margins.

Day 14: Intranasal examination of left nostril reveals no palpable constriction of air passage by tumor compression.

Day 16: Afternoon resting metabolic rate has averaged 2.50 over previous three days, reaching as high as 2.91. This high resting metabolic rate has been accompanied by copious suppuration from the ulcer each afternoon, evening and night, and by an accompanying "terrible itching" sensation throughout the tumor region. Detailed measurements of tumor dimensions made by attending oncologist reveal a 90.4% decrease in overall tumor mass, relative to that present on Day 1.

The ulcer diameter has decreased approximately 39%. Tumor is softer still, and left nostril is free of any constriction. Patient remains in good condition, but is bothered by periods of shortness of breath when resting metabolic rate is particularly elevated and she is active, as in taking afternoon walks; this condition is to be expected for an individual with such excessive body weight. Results of laboratory tests performed on Day 12 are all normal; cortisol level is 9.0 µg/dl.

Day 20: Margin of ulcer is flatter; overall elevation of surface outside of ulcer is essentially gone. Conjunctival inflammation has disappeared.

Day 23: Detailed measurements of tumor dimensions made by attending oncologist reveal a 96% decrease in overall tumor mass. The only clinically discernable area where tumor may remain is in the area adjoining the upper margin of the ulcer; this area is only 1 to 2 mm in width. Ulcer has diminished in diameter to 0.6 cm, a 41% decrease; its depth has also diminished greatly. Throughout the period of oncolysis the pattern of tumor-mass regression has been one of continuous shrinkage of the overall mass back towards its originating epicenter (the present ulcer crater). Results of laboratory tests made on Day 19 are all normal; cortisol level 12 µg/dl.

Day 24: Patient leaves hospital to enter the outpatient treatment stage of Phase II. In Phase II, the patient will resume normal lifestyle activities but will report back to the attending oncologist at frequent intervals for laboratory tests, physical examinations, and tumor status assessment. The medication schedule will remain exactly the same as in Phase I. The DNR will remain calorically the same but will be from regular food items, rather than from the Phase I nutrient cocktail suspensions.

Response to Treatment (Phase II):

Day 52: Patient has been on out-patient regimen for 28 days. Treatment protocol has remained essentially the same as in Phase I, except the DNR carbohydrate, protein, and essential fatty acids are provided by normal food items, for palatability reasons. The patient is judged clinically free of active tumor by attending oncologist. Small ulcer remains, but margins are smooth and flat. Ulcer depression appears lined with fibrous material. No active suppuration despite continued therapy regimen. Results of laboratory tests have been normal. Patient has resumed usual housewife duties without significant problems.

Day 98 (three months): Examination reveals only the same small, slowly-closing ulcer; no evidence of tumor or tumor activity at clinically observable level. Patient is offered option of surgical removal of ulcer and closure of lesion site but refuses. Patient continues on present Phase II regimen.

In the following Examples 3 and 4, only the AAD and the LEB of the present therapy system were administered. The AAD in each case was a combination of a high $pK_a$ UA (CTFB) and a wasteful ATP-hydrolyzer (TH). The LEB in each case was quercetin (in the dihydrate form). The dietary intake was composed of regular food items, because of the digestive compliance limitations of these patients. The results demonstrate the strong and very rapid oncolytic action attainable with such an AAD combination of agents which are insensitive to intracellular pH conditions and thus are highly effective with the LEB at dosage levels which produce only moderate elevations in the body resting metabolic rate during therapy, and which act separately by inhibiting O/P ATP production and by wasting ATP produced by O/P and glycolysis in the cancer cells.

EXAMPLE 3

Example Case No. 3:
Female, 57 years old.
Diagnosis:
Poorly differentiated to undifferentiated serous papillary cystadenocarcinoma of the ovary, widely metastasized; Stage 3.
Basis of Diagnosis:
Histological analyses of multiple specimens from primary and metastatic tumors, obtained at exploratory laparotomy, of the ovary, sigmoid colon, abdominal wall, liver and diaphragm.
Therapy Prior to Present Treatment:
Surgery (four times), multiagent mitoxin chemotherapy (Cisplatinum, Adriamycin, Cytoxan, Alkeran), extensive radiotherapy.
Tumor Status at Start of Present Therapy:
CAT scan report: "massive retroperitoneal, periportal lymphadenopathy with associated obstruction of right ureter and intraabdominally spread ovarian carcinoma." In addition, patient had a large (8 cm×5 cm) tumor mass completely occupying the left supraclavicular fossa and multiple large palpable tumors in the lower right abdomen Tumors in both sites hard, firmly fixed, and non-painful. Extensive abdominal ascites fluid volume, precluding meaningful dimensional palpation of intraabdominal tumor masses Pronounced edema in right thigh due to intraabdominal compression of iliac artery. Patient very thin, weak, almost totally anorexic with great pain and continued episodes of uncontrollable vomiting.

Treatment Conditions:

Because of the tenuous condition of the patient and inability to ingest adequate food for full caloric balance at elevated metabolic rates, treatment with the present therapy was limited to three periods of two days each, with approximately seven days between treatments. Only regular foods (eggs, milk, cereals, fruits) and the AAD-LEB metabolic effectors were used, the AAD being the high $pK_a$ UA 5-chlorotrifluoromethyl benzimidazole (CTFB), $pK_a=8.9$, combined with TH (Thyrolar-1, Armour), and the LEB being quercetin. CTFB was given orally at a dosage of 5 mg/Kg per capsule, one capsule twice daily, and the Thyrolar-1 at a dosage of 1.5 tablets per day, each day the CTFB was given. The quercetin was given twice daily (8:00 AM and 8:00 PM) at a dosage level of 1.5 mg pure quercetin per Kg per capsule, one capsule each time the CTFB was administered. The food was supplied at the level of 1369 Kcal/d, but only about two-thirds of this caloric level was actually ingested.

Response to Treatment:

In the first treatment period, the CTFB was administered for only 1½ days (one capsule AM and PM of the first day, and one capsule AM of the second day). On the third day, the abdominal ascites fluid volume had decreased significantly, and on the second day following the treatment period the patient had lost over 2 Kg of ascitic fluid; the supraclavicular mass had become softer and more movable. The patient's resting metabolic rate was only 1.3 times her standard Mayo basal metabolic rate during the period. Following treatment, the food intake was equivalent to caloric balance. The patient lost another 1.5 Kg of ascitic fluid in the ensuing three days, and the fluid then began to increase slowly up to the second treatment period. In the second treatment period, the CTFB was administered for two consecutive days. By the third day following the two-day treatment period, the ascites fluid volume had greatly decreased, to the extent that the body weight was decreased by approximately 5%. The body weight remained essentially constant for several days after this initial rapid decrease. The neck tumor mass was softer and more movable, and slightly painful. The masses in the lower abdomen, now palpable, similarly were of soft consistency and movable, and also had become slightly painful upon palpation. The edema in the right leg decreased significantly. The frequency and the volume of urination increased. Overall pain became less severe, in general. The resting metabolic rate immediately following this treatment period rose to 1.5 before subsiding slightly. In the third treatment period, the CTFB was administered for only 1½ days, as in the first period. On the third day, the ascites fluid volume was further decreased, with the abdomen nearing normal size. The neck tumor mass was not only still softer and more movable upon palpation, but had decreased significantly in size. The neck mass had become very painful to palpation. The abdominal masses were also softer in consistency with increased movability, and similarly had become quite painful to palpation, as is characteristic following significant induced oncolysis. The leg edema had disappeared completely. The patient's resting metabolic rate rose to 1.7 during this final treatment period. Throughout the therapy, the patient's hematology, blood chemistry, enzymes, serology and urinalysis remained normal. The patient's overall weight loss (~7%) was attributable to a pronounced decrease in the ascitic fluid mass.

EXAMPLE 4

Example Case No. 4:
Male, 52 years old.
Diagnosis:
Adenocarcinoma of the stomach, with extensive visceral metastases.
Basis of Diagnosis:
Initial gastroscopy; histological analyses of multiple biopsy specimens. Subsequent laparotomy revealed massive tumor of the gastric body and antrum, nearly closing the pilorus; multiple peritoneal metastases; metastases in liver and pancreas; abdominal fluid positive for numerous malignant ascites cells; case judged surgically untreatable and terminal.
Therapy Prior to Present Therapy:
One cycle of combination-drug mitoxin chemotherapy (5-Fluorouracil, Adriamycin, Vincristine); patient experienced violent side-effects and refused further treatment with mitoxin chemotherapy.
Tumor Status at Start of Present Therapy:
Massive tumor (8 cm×18 cm) of the stomach, with extensive metastatic invasion of all viscera and peritoneal cavity; tumor masses very hard and fixed upon palpation; high rate of malignant ascites production. Patient experiencing severe pain and edema in right leg as a result of abdominal compression restriction of circulation. Patient's body weight upon entry (four days prior to treatment) was nearly standard for his sex and height, although he previously was grossly overweight before onset of his illness.
Treatment Conditions:
The primary clinical objective of administering the present therapy was to control the rapidly building ascitic fluid concentration. Patient's body weight had increased 7.4% in the four days preceding the start of therapy, due to ascitic buildup. Because of the tenuous condition of the patient and expected inability to ingest adequate food for caloric balance, treatment with the present therapy was limited to two periods of two days each, with eight days between treatments. Only the AAD and LEB metabolic effectors were used, the AAD being the high $pK_a$ UA 5-chlorotrifluoromethyl benzimidazole (CTFB), $pK_a=8.9$, combined with TH (Thyrolar-1, Armour), and the LEB being quercetin. CTFB was administered orally in capsules at a dosage of 5 mg/Kg/capsule, one capsule twice daily, and the Thyrolar-1 at a dosage of 1.5 tablets per day. The quercetin was administered at a dosage level of 1.5 mg pure quercetin per Kg per capsule; one capsule was given each time a capsule of CTFB was given. The food (eggs, milk, cereals, cooked fruits) was supplied at the level of 1559 Kcal/d, in mash form.
Response to Treatment:
In the first treatment period, the CTFB was administered as follows: two capsules, one in AM and one in PM, on first day, and one capsule, AM, on second day. On the second day following the treatment period, the patient's weight had decreased 1.5% due to decrease in tumoral ascitic fluid and by the eighth day post-treatment, by 6.1%. This decrease in malignant ascites activity was accompanied by an appreciable decrease in abdominal distention. Edema of the right leg also decreased. The resting metabolic rate reached a maximum of only 1.44 on the first day following treatment (up from 1.20 before treatment) and the patient was able to nearly maintain caloric balance with the food diet at the average therapeutical metabolic rate (measured twice daily). In the second treatment period, the CTFB was administered twice each day. Following this second treatment period, the body weight decreased to the patient's standard body weight for his sex and height, evidencing full control by the present therapy of the patient's malignant ascites activity, with only minimal treatment durations and metabolic rate elevations. Abdominal palpation revealed a much softer consistency of visceral masses than upon entry.

In Examples 5 through 12, eight patients were treated with a therapeutical regimen according to the present invention wherein only the DNR and AAD metabolic effectors were administered. The DNR was adjusted daily to ensure caloric balance. The AAD was the O/P uncoupling agent 2,4-Dinitrophenol (DNP), and was administered once daily in capsule form at a nominal dosage level of 1.5 mg/Kg of initial body weight. Patient resting metabolic rates were measured twice daily, AM and PM, to provide data for DNR caloric determinations and to quantitate the level of uncoupling activity (i.e., ATP wasting) being attained. Phase I consisted of 12 days of treatment, followed by a rest interval of 7 to 10 days. Phase II extended for 12 days of treatment, under daily clinical observation. The patients of Examples 5 through 8 were treated in Phase I and Phase II; those of Examples 9 through 12 were treated only in Phase I. The results of these cases illustrate the powerful oncolytic effect of the present therapy system when just the DNR and AAD metabolic effectors are used in adequate levels to produce a major decrease in NADH to the cancer cell respiratory chain while effecting a major depression of their $ATP_A$ by wasting via O/P uncoupling with DNP, a relatively low pKa uncoupling agent.

EXAMPLE 5

Example Case No. 5:
Female, 54 years old.
Diagnosis:
Adenocarcinoma (clinically colon), far advanced, infiltrating viscera; extensive liver metastases.
Basis of Diagnosis:
Ultrasound scans with biopsy of protrusive tumor mass; laparotomy with multiple histological specimens and analyses. (Tumor inoperable due to wide involvement).
Therapy Prior to Present Treatment:
None.
Tumor Status at Start of Present Treatment:
Huge tumor mass occupying the epi- and mesogastrium region (X-ray), tumor compressing lower esophagus to near closure (barium esophagram), stomach compressed and displaced to left; left lobe of liver essentially replaced by tumor, right lobe with numerous metastases (liver scan); hard, fixed, palpable tumor mass measuring 10 cm (vertical)×7 cm (horizontal) protruding superficially from abdomen in region corresponding to left lobe of liver. Patient weak, thin, rapidly losing weight, pain and intense feeling of pressure in tumor area; able to swallow only liquids, which must be taken very slowly; stomach accommodates only small volume before feeling of satiation occurs. (Dimension and mass changes given in the following Response to Treatment data are for the protruding 10 cm×7 cm abdominal tumor mass.)
Response to Treatment (Phase I):

Day 1: Patient starts on DNR; no DNP. Tumor: 10.0 cm.

Day 2: Patient starts on DNP.

Day 3: Patient reports she is feeling much better; abdominal pain and pressure sensation are definitely decreasing; swallowing is easier.

Day 6: Oncologist reports tumor is becoming softer in consistency. Tumor: 8.5 cm; 38% reduction.

Day 8: Patient reports all pain and pressure sensations have disappeared; swallowing fully normal.

Day 10: Oncologist reports tumor still decreasing in size; has become still softer in consistency.

Day 12: Final day of Phase I treatment. Resting metabolic rate was 3.24 during the final 16 hours of the period.

Day 13: Patient in excellent condition; reports feeling fine. Vital signs, blood parameters all normal; tumor greatly shrunken, non-protrusive, flat, difficult to palpate. No signs whatever of toxemia despite large initial tumor mass and rapid rate of tumor lysis on Day 12. Tumor: 6.0 cm; 78.4% reduction.

Day 16: Oncologist reports tumor has continued to shrink despite cessation of treatment and return to normal protein level; overall dimension has decreased 50%. Tumor: 5.0 cm; 87.5% reduction.

The oncologist noted the following: X-rays, liver scan, and esophagram performed on Day 18 indicated a pronounced decrease in the visceral tumor mass and liver metastases, with suggestive regeneration of normal liver normal esophageal transport and emptying into stomach. Throughout the treatment period, the patient's blood pressure, pulse rate, temperature, and blood parameters remained stable and in the normal range. The DNP produced the intended transient increase in metabolic rate; no side effects other than mild sweating due directly to the DNP, were observed. Patient's overall condition has improved greatly.

Response to Treatment (Phase II):

Day 1: Patient on DNR and DNP. Pain, with sensation of intense pressure within tumor region, swallowing difficult. Tumor: 11.0 cm.

Day 3: Patient reports swallowing is easier. Oncologist reports tumor softer and slightly decreased in size.

Day 5: Patient reports abdominal pain much diminished. Oncologist reports tumor continuing to decrease in size; becoming flatter and less protrusive.

Day 6: Patient reports feeling much better; abdominal pressure sensation much decreased as is fullness sensation; no pain in tumor region. Oncologist reports tumor now flat, non-protrusive; continuing to decrease in size. Tumor: 7.0 cm; 74.2% reduction.

Day 12: Final day of Phase II treatment. Patient reports feeling fine; pressure sensation gone; swallowing normal. Vital signs, blood parameters normal. Oncologist reports tumor residue very soft, difficult to palpate. Tumor: 6.0 cm; 83.8% reduction.

Day 13: Blood analyses reveal a significantly elevated level of lactic dehydrogenase commensurate with the pronounced tumor lysis observed in the palpable tumor; the blood urea nitrogen level is normal.

The oncologist noted the following: the patient's body weight remained stable throughout the treatment period, as did the serum total protein level; the red blood cell count increased from 3.9 to $4.1 \times 10^6$. On Day 15, the patient ate normal meals of solid food without encountering swallowing or saturation problems of any kind; was in excellent general condition. Despite the extensive metastatic involvement of the liver, this patient experienced no digestive problems and was able to accommodate and assimilate the DNR quite well, even at high caloric intake levels. The serum lactic dehydrogenase level on Day 13 was elevated nearly ten-fold, indicating the intensity of the tumor lysis of the preceding days. Similarly indicative of the pronounced decrease in overall tumor activity was the fact that the blood urea nitrogen (BUN) level decreased 78% in this semicachexic patient over the "Phase I" treatment period.

EXAMPLE 6

Example Case No. 6:

Male, 57 years old.

Diagnosis:

Epidermoid carcinoma of the larynx (left supraglottic fold and false cords); metastasized to the left neck.

Basis of Diagnosis:

Direct laryngoscopy with multiple biopsies; biopsy of neck metastasis; CT scan and Xerographs of larynx and neck.

Therapy Prior to Present Treatment:

None.

Tumor Status at Start of Present Treatment:

Large tumor of the left supraglottic fold infiltrating the false cords, but not crossing the midline; 2 cm diameter, hard, fixed, protruding metastasis in the left neck, causing severe steady submaxillar pain due to pressure on nerve. Patient unable to eat solid food because of intense pain on swallowing, even liquids cause much pain; voice hoarse, moderately advanced emphysema of both lungs. (Dimension and mass changes given in the following Response to Treatment data are for the protruding 2 cm diameter metastasis in the left neck.)

Response to Treatment (Phase I):

Day 1: Patient begins on DNR; no DNP. Blood parameters (including serum total protein level), liver function tests, urinalysis, and vital signs all normal. Patient has difficulty swallowing because of throat pain, also suffers from intense pain due to pressure on nerve from neck metastasis. Oncologist reports neck tumor hard, fixed, extremely painful. Tumor: 2.0 cm.

Day 2: Patient starts with DNP.

Day 3: Patient reports intense pain in left neck; radiates to left ear.

Day 6: Patient reports pain in left neck has diminished.

Day 9: Patient reports pain in left neck has continued to diminish; feels that neck tumor is definitely decreasing in size. Oncologist has not measured tumor because of pain upon palpation.

Day 11: Patient's resting metabolic rate increased to 2.97 and remained elevated during whole day.

Day 12: Final day of Phase I treatment. Resting metabolic rate decreased to 2.57, but remained above 2.0 for the remainder of the day. DNP discontinued yesterday.

Day 13: Patient is greatly improved; reports feeling much better. Vital signs all normal. Neck tumor is much less painful upon palpation. Oncologist reports neck tumor drastically decreased over two-day period of elevated resting metabolic rate (87.5% decrease in total tumor mass); tumor much softer in consistency. Tumor: 1.0 cm.

Day 14: Patient reports pain has essentially disappeared in neck, but throat is "sore" at site of primary. Vital signs and blood parameters all normal; resting metabolic rate equals 1.0. Patient feels fine; appetite very good.

Day 18: Oncologist reports neck tumor residue slightly mobile, non-protrusive, hardly palpable; non-painful. Former hoarseness of voice (dysphonia) has greatly diminished. Tumor: 0.8 cm; 93.6% reduction.

The oncologist noted the following: throughout the treatment period the patient's body weight, blood pressure, pulse rate, respiratory rate, temperature and blood cytological and chemical parameters remained stable and within the normal range. The DNP produced the intended increase in metabolic rate; no side effects due directly to the DNP were observed. Despite the fact that this patient had moderately advanced emphysema in both lungs, the elevation of the resting metabolic rate to as high as 2.97 produced no symptoms of respiratory insufficiency.

Response to Treatment (Phase II):

Day 1: Tumor is hard, fixed, immobile, and very painful on palpation; patient is put on DNP (4.5 mg/Kg). Tumor: 4.0 cm.

Day 5: Neck tumor greatly diminished, as is the pain associated with it; burning sensation at site of internal primary, especially upon swallowing. Patient feels very good otherwise, takes DNR well. Tumor: 1.0 cm; 98.4% reduction.

Day 6: Voice hoarseness much diminished.

Day 8: Neck tumor residue hardly palpable; difficult to find; painless. Throat soreness at site of internal primary upon swallowing cold liquids, but no pain with warm liquids or warm semi-solid food. Laryngoscopy of primary site reveals a small, non-bleeding, ulcerative lesion on the left supraglottic fold, with surrounding inflammation. Patient feels fine, vital signs normal; resting metabolic rate equals 1.27. Tumor: 0.8 cm; 99.2% reduction.

Day 11: Voice much clearer; throat pain less upon swallowing. Patient feels fine; is very hungry. Tumor: nonpalpable.

Day 13: Final day of Phase II treatment; DNP discontinued after today. Patient is asymptomatic; feels fine; very hungry; only slight pain at primary site. Tumor: nonpalpable.

Day 16: Patient returns to solid food; no pain in throat after first three swallows; feels fine. Tumor: nonpalpable.

The oncologist noted the following: Throughout the treatment period the patient's body weight, blood pressure, pulse rate, respiratory rate, temperature, and blood cytological and chemical parameters remained clinically stable and within the normal range. The DNP produced the intended increase in metabolic rate; no side effects whatever due to the DNP were observed.

EXAMPLE 7

Example Case No. 7:
Female, 51 years old.
Diagnosis:
Lymphocytic lymphoma (nodular, mixed-cell type); retroperitoneal; infiltrating; far advanced.
Basis of Diagnosis:
Laparotomy with multiple biopsies; CT scans.
Therapy Prior to Present Treatment:
Extensive conventional mitoxin chemotherapy; laetrile.
Tumor Status at Start of Present Treatment:
Huge retroperitoneal tumor mass with hard, fixed, nonpainful portion 14 cm (vertical)×10 cm (lateral) protruding superficially in the epi- and mesogastrium region; protruding mass easily palpable, with well-defined margins; central tumor mass displacing viscera outwards and downwards; liver, lungs, lymph nodes and marrow negative for metastases; blood free of blast cells. Patient extremely thin (cachexic), pale, anemic, tired, nervous; blood pressure slightly below normal (110/60); reports strong sensation of pressure in tumor region; severe abdominal pain at times; lumbar spinal pain, often radiating into legs. (Dimension and mass changes given in the following Response to Treatment data are for the superficially protruding 14 cm×10 cm tumor mass.)

Response to Treatment (Phase I):

Day 1: Patient begins on DNR; no DNP. Tumor: 14.0 cm.

Day 2: Patient begins on DNP; complains of allergy activation (skin rash) because of corn-containing food she ate just prior to Day 1; claims long-standing allergy to corn products.

Day 9: Some pain in lower back; patient's resting metabolic rate has increased to therapy level (1.68) for first time. Tumor: 14.0 cm.

Day 11: Patient reports all pain has subsided; all pain medication stopped; blood test shows anemia has improved; allergy symptoms completely gone; resting metabolic rate equals 1.68.

Day 12: Final day of Phase I treatment; resting metabolic rate has increased to 2.47.

Day 13: Patient feels much better; all pain has diminished greatly; pressure sensation in tumor region has disappeared. Vital signs, blood parameters normal. Resting metabolic rate equals 1.0. Hemoglobin has increased 16% since starting treatment. Oncologist reports dramatic decrease in tumor size in just one day at elevated resting metabolic rate (2.47); tumor much softer; no longer protrusive; difficult to palpate. Tumor: 8.5 cm; 77.6% reduction.

Day 14: Patient in excellent state; feels very happy; has much more energy. Blood parameters normal except serum total protein level still slightly low. Oncologist reports abdominal tumor mass has continued to decrease in size; has regressed inward and is very difficult to palpate; dramatic rate and extent of tumor reduction verified independently by three different oncologists. Tumor: 5.5 cm; 93.9% reduction.

Day 18: Patient in excellent state; no pain whatever; vital signs all normal. Oncologist reports X-rays of abdomen show tumor opacity much reduced; viscera seen more clearly.

Day 20. Patient in excellent condition; good appetite; skin and mucosal color much improved; pain-free. Oncologist reports previously protrusive residue still decreasing; is much softer; has sunk inward; residue can be detected only with deep palpation.

The oncologist noted the following: Throughout the treatment period the patient's body weight, blood pressure, pulse rate, respiratory rate, temperature, and blood cytological and chemical parameters remained stable and within the normal range. The DNP produced the intended transient increase in metabolic rate; no side effects due to the DNP were observed.

Response to Treatment (Phase II):

Day 1: Patient with DNR and DNP; strong pressure sensation in central tumor site; feels very weak. Tumor: 11.0 cm.

Day 4: Patient reports diminishing of pressure sensation in tumor site; some back pain. Oncologist reports tumor appears to be decreasing in size and becoming softer; no measurement given.

Day 6: Patient reports pain minimal. Vital signs normal, except blood pressure which is characteristically low (90/60).

Day 9: Oncologist reports tumor shape is changing; can now palpate what feels like individual lymph nodes; difficult to palpate tumor as it appears to be breaking up and flattening out; 8 cm is maximum extent of flattened residue. Tumor: 8.0 cm; 61.5% reduction.

Day 13: Final day of Phase II treatment period; patient reports minimal pain; slept well.

Day 14: Oncologist reports tumor has lost shape and coherency; former mass seems to be disintegrating; more mobile; much softer consistency.

Day 15: Oncologist reports tumor residue very ill-defined and flattened; maximum dimension of diffuse residue is 7.5 cm. Patient resumed eating regular food without any problem; hemoglobin has increased 24.8% over initial level; blood parameters are normal including platelet concentration; blood is free of blast cells.

The oncologist noted the following: Throughout the treatment period the patient's body weight, pulse rate, respiratory rate, temperature, and blood cytological and chemical parameters remained stable and within the normal range; the blood pressure was slightly below normal, as is characteristic for this patient. The DNP produced the intended increase in metabolic rate; no side-effects due to the DNP were observed. The average dosage of DNP over the 13-day treatment period was only 2.0 mg/Kg; the average resting metabolic rate was correspondingly low, 1.30. Still, in the presence of the relatively low daily protein intake, the tumor regressed rapidly and ultimately underwent a generalized disintegration; the blood remained entirely free of tumor cells during this disintegration. Even with the reduced level of protein in the DNR, the hemoglobin increased 24.8%.

EXAMPLE 8

Example Case No. 8:
Male, 59 years old.
Diagnosis:
Adenocarcinoma of the prostate (moderately differentiated); infiltrating periprostatic soft tissue, lymph nodes, and wall of urinary bladder, widely disseminated bone metastases.

Basis of Diagnosis:
Cystoscopy with multiple biopsies; right pelvic lymph node dissection with histological analyses; transurethral resection with histological analyses; nephrogram; bone scans.

Therapy Prior to Present Treatment:
Laetrile, Vitamin A, enzymes (IV, orally); hormone therapy; surgery (TURP).

Tumor Status at Start of Present Treatment:
Greatly enlarged, rock-hard, malignant prostate; with tumor widely infiltrating periprostatic soft tissue, including wall of urinary bladder; left kidney semi-occluded due to tumoral obstruction of left ureter at point of entrance into bladder; multiple, widely disseminated bone metastases in cervical, dorsal, and lumbar spine, right, scapula, both iliacs, and both femurs. Patient still in good general condition; no pain, good appetite; moderately obese; chronic hypertension; frequent night and day urinations due to tumor pressure on bladder; difficulty in urinating; urine stream flow greatly reduced; acid phosphatase level nearly twice the normal maximum.

Response to Treatment (Phase I):

Day 1: Patient starts on DNR; no DNP. Tumor: Acid phosphatase level nearly double the normal maximum.

Day 2: Patient starts on DNP. Patient's resting metabolic rate rises to 1.4; vital signs normal; very good appetite.

Day 6: Patient feels fine, resting metabolic rate equals 1.52; blood pressure elevated due to characteristic hypertension. Tumor: Night urinations have decreased to one; starting and maintaining urine flow easier.

Day 9: Patient feels fine; vital signs normal, except blood pressure still elevated; moderate pain in back when lying in bed, disappears in walking.

Day 11: Patient feels fine; resting metabolic rate equals 1.98, blood pressure has decreased with diuretic.

Day 12: Final day of Phase I treatment; patient reports sweating episode during previous night, temperature normal; resting metabolic rate equals 2.30 today.

Day 13: Patient reports he feels great; all pain has disappeared; vital signs are normal, except elevated blood pressure which continues to decrease with diuretic. Tumor: Urine flow significantly improved; stream stronger and more steady.

Day 14: Patient reports he feels great: asymptomatic; blood pressure and blood parameters normal, including serum total protein level. Tumor: Oncologist reports rectal examination shows prostate size has decreased, and consistency is not as hard as originally; acid phosphatase is significantly elevated, 5.3 times normal maximum, due to release from lysed prostatic cells.

Days 15-21: Patient continues to feel fine; entirely asymptomatic. Tumor: Urination continues to improve despite cessation of treatment and resumption of increased protein intake; urination stream steady.

Day 22: Patient continues asymptomatic; blood pressure under control with diuretic. Tumor: Bone scan shows significant reduction of bone metastases; oncologist reports excellent response to treatment period.

The oncologist noted the following: Throughout the treatment period the patient's body weight, pulse rate, respiratory rate, temperature, and blood cytological and chemical parameters remained stable and within normal range; the characteristically elevated blood pressure was controlled with the use of a diuretic. The DNP produced the intended transient increase in metabolic rate; no side effects due to the DNP per se were observed. The patient remains pain-free and in excellent general condition.

Response to Treatment (Phase II):

Day 1: Patient on DNR and DNP; general condition good; moderate pelvic pain. Tumor: Prostate much enlarged and very hard.

Day 4: Patient reports pelvic pain has ceased entirely; feels fine. Tumor: Oncologist reports prostate decreasing in size and becoming softer in consistency.

Day 5: Patient reports greater volume of urine excreted per urination than before treatment started; feels fine. Tumor: Patient reports easier to commence urine flow; has new sensation that bladder now empties completely upon urination.

Day 8: Patient asymptomatic; vital signs normal; blood pressure holding at 170/90 with diuretic. Tumor: Oncologist reports prostate is becoming flatter, more like normal shape. Patient reports stronger urination stream.

Day 9: Patient asymptomatic; feels fine. Tumor: Oncologist reports prostate is flatter and softer.

Day 13: Final day of Phase II treatment period; DNR administration ceased today. Tumor: Oncologist reports prostate still flatter and softer, especially on left side; former vesicle tenesmus has disappeared. Patient reports still better urine flow, without interruption; night urination frequency much less.

Day 15: Patient in excellent condition; asymptomatic. Tumor: Oncologist reports prostate even flatter and softer, with pronounced change on left side; non-painful; steady regression toward normal prostate size. Hemoglobin level has increased 13.4% over the initial level; classically, prostate cancer patients always exhibit anemia. Additionally, the acid phosphatase level (classically taken as the most sensitive indicator of prostate tumor cell activity) is now completely normal.

The oncologist noted the following: Throughout the treatment period the patient's body weight, pulse rate, respiratory rate, temperature, and blood cytological and chemical parameters remained stable and within the normal range; the characteristically high blood pressure was controllable with diuretics. The DNP produced the intended increase in metabolic rate; no side effects due to the DNP were observed. Prostate cancer cells generally proliferate only very slowly, and hence possess a relatively low level of cellular metabolism; still, the tumor burden of the present subject regressed steadily with the present treatment. Equally significant is the fact that the patient was also moderately obese, wherein the malignant cells were given a strong survival advantage via the availability of a nonprotein energy source; yet, the present treatment was still able to impose a steady and effective rate of oncolysis. The previously elevated acid phosphatase level, the standard indicator of prostate tumor activity, became completely normal. Even with the protein intake reduced to the equilibrium level, the hemoglobin increased 13.4%. The pronounced increase in urine volume that was experienced is indicative of a removal of the left urethral tumor obstruction; similarly, the return of the sensation of complete emptying of the bladder correlates directly with the palpable reduction in the circumurethral tumor/prostate mass.

EXAMPLE 9

Example Case No. 9:
Female, 65 years old.
Diagnosis:
Adenocarcinoma of the breast (ductal, infiltrating); widely metastasized.
Basis of Diagnosis:
Tumorectomy with histological analyses (on two separate occasions); X-rays; (lungs); liver scans; bone scans.
Therapy Prior to Present Treatment:
Surgery, extensive conventional (mitoxin) chemotherapy; radiation; anti-estrogen drugs.
Tumor Status at Start of Present Treatment:
Widely disseminated metastases; protruding superficial tumor mass, hard, fixed, 3 cm diameter just below left collarbone; protruding superficial tumor, hard, semi-mobile, in surgical scar (1 cm diameter) on left breast; metastases in both lungs; multiple bone metastases: skull, spine, pelvis (extensive destruction), femurs; extensive liver metastases. Patient is in intense pain, primarily pelvic, spinal, and right lower jaw; pain intensifies with movement; pancytopenia; arthritis of many years duration; stomatitis; history of sporadic hypoglycemia; elevated urine estrogen; many emotional problems; vital signs normal. Unable to walk or even get out of bed because of pain.

Response to Treatment:
Day 1: Patient starts with DNR; no DNP. Patient suffers intense pain, especially upon movement; unable to get out of bed or walk. ("cb" denotes the superficially protruding tumor mass below the collarbone; "br" denotes the tumor mass in the surgical scar on the left breast.) Tumor: 3.0 cm (cb), 1.0 cm (br).

Day 2: Starts with DNP. Patient reports pain at all levels is less, although still appreciable.

Day 4: Patient reports that pain at all levels is greatly diminished; is in much better spirits and is more cooperative.

Day 5: Patient reports that pain at all levels has essentially subsided; is walking about with aid of walker; is able to get out of bed by self; is in excellent spirits.

Day 8: Patient remains practically free of pain; walks about easily with aid of walker; reports that she is sure tumors under the collarbone and in surgical scar are diminishing in size.

Day 10: Patient reports slight back pain, but is fine otherwise; still moving about freely with aid of walker; resting metabolic rate equals 1.44.

Day 11: Patient reports perspiring appreciably last night; some shortness of breath; vital signs normal; resting metabolic rate equals 1.73.

Day 12: Final day of treatment period; resting metabolic rate equals 2.19; patient remains in bed.

Day 13: Patient reports feeling tired, but otherwise OK; vital signs normal; oncologist reports dramatic shrinkage of observable tumors over the past two-day period; residual tumor masses much softer; both only slightly protrusive. Tumor: 1.2 cm (cb), 0.4 cm (br); 93.6% regression.

The oncologist noted the following: Throughout the treatment period the patient's body weight, blood pressure, pulse rate, respiratory rate, temperature, and blood cytological and chemical parameters remained stable and within the normal range. The DNP produced the intended transient increase in metabolic rate. No side effects due to the DNP per se were observed. This patient had many family and emotional problems and was intensely unhappy with hospital confinement and regimentation of diet, being unaware of the seriousness of her condition; became most uncooperative and undependable in taking the required DNR; was eventually released at her insistence. Despite this impediment and the extensive metastatic infiltration of the liver, she responded excellently to the treatment regimen; her body weight remained stable and her hemoglobin increased 16%. A bone scan performed on Day 28 (15 days after the completion of the treatment period, and during a time she had been on a normal protein intake) revealed a significant improvement in the various bone metastases with several of the initial lesions having essentially disappeared. Her plasma calcium remained fully normal during her stay at the hospital despite the extensive bone metastases; however, she began to exhibit increasingly severe hypercalcemin within a short time after leaving and resuming her regular diet.

EXAMPLE 10

Example Case No. 10:
Male, 64 years old.
Diagnosis:
Carcinoma of the lung (large-cell, undifferentiated), upper lobe, right lung.
Basis of Diagnosis:

Histological analysis of tumor specimens (two independent analyses); X-rays.

Therapy Prior to Present Treatment:
Laetrile; dietary.

Tumor Status at Start of Present Treatment:
Tumor activity confined to upper lobe of right lung, which X-rays show to be completely opacified due to tumor and atelectasis; no metastases detectable elsewhere (liver, bone, lymph nodes, viscera). Patient is very thin and pale; anemic; suffers a 25% reduction in oxygenation capacity and occasional episodes of shortness of breath; has heart murmur with extrasystole; tires easily; has periodic episodes of coughing; appetite good; no pain; reasonably good general condition; vital signs normal.

Response to Treatment:
Day 1: Patient starts on DNR; no DNP.
Day 2: Patient starts on DNP.
Day 6: Patient in good condition; feels fatigued upon walking; vital signs normal; appetite good.
Day 11: Patient in excellent condition; much improved color in skin and mucosa; red blood cell count has increased; resting metabolic rate rose to 1.93; no complaint of dyspnea.
Day 12: Final day of treatment period. DNP has been discontinued; patient feeling fine; vital signs normal; resting metabolic rate equals 2.70; patient walking about with no complaint of dyspnea. Patient feels fine; color improvement very noticeable; vital signs normal.
Day 14: Patient is in excellent condition. Tumor: Oncologists (two independent examinations) report definite indications of increased ventilation of right lung; detect new sounds ascribed to ventilatory air flow.
Day 20: Patient in excellent condition; reports a feeling of overall well-being. Tumor: Patient is able to take long walks without any occurrence of dyspnea; ventilation much improved in right lung.

The oncologist noted the following: Throughout the treatment period the patient's body weight, blood pressure, pulse rate, respiratory rate, temperature, and blood cytological and chemical parameters remained stable and within the normal range, except for the initial anemia which greatly improved. The DNP produced the intended transient increase in metabolic rate; no side effects due to the DNP per se were observed. The patient's hemoglobin increased 40% during his stay. The ventilation in his right lung continued to improve until departure. No specific identification of tumor masses per se could be made in any of the post-treatment X-rays, which revealed only the same uniform atelectatic opacity of the lobe as seen previously. Because of the significant functional improvement, and pressing family matters, the patient left for home before commencement of the Phase II treatment period.

EXAMPLE 11

Example Case No. 11:
Male, 67 years old.
Diagnosis:
Carcinoma of the lung (oat-cell, undifferentiated); tumor located in left hilum with extensive diffuse infiltration into surrounding lung tissue.
Basis of Diagnosis:
Bronchoscopy with biopsy (at junction of left upper and lower lobes); X-rays.
Therapy Prior to Present Treatment:
None.

Tumor Status at Start of Present Treatment:
Tumor mass centered in the left hilum with extensive diffuse infiltration of surrounding tissue; no evidence of liver, bone or brain metastases on respective scans; lymph node areas negative except for one suspicious 6 mm node in the left base of the neck. Patient is very thin and losing weight rapidly because of nervous anorexia; is extremely nervous and under great emotional strain because of family pressures upon him; has frequent gastritis; has severe spells of violent coughing, which are increasing steadily in frequency and duration; suffers shortness of breath; occasional retrosternal pain; vital signs normal; blood parameters, liver function and urinalysis results normal.

Response to Treatment:
Day 1: Patient starts on DNR; no DNP. Tumor: Patient has frequent violent coughing spells; uses codeine cough syrup, but with little benefit; reports increased retrosternal pain and shortness of breath when excited or agitated.
Day 2: Patient starts on DNP.
Day 6: Patient reports feeling of improvement and overall well-being, despite gastritis induced by emotional upset of family problems. Tumor: Patient reports coughing spells less violent.
Day 7: Resting metabolic rate equals 1.39 today; patient feels fine; no dyspnea. Tumor: Patient reports coughing spells milder and much less frequent.
Day 11: Patient in good general condition despite continuing emotional upset due to family problems; vital signs normal; resting metabolic rate up to 2.03. Tumor: Coughing episodes continue to decrease, in intensity, duration, and frequency. Patient experiences no dyspnea, despite elevated resting metabolic rate and active walking about.
Day 12: Final day of treatment period. DNP discontinued yesterday; resting metabolic rate equals 1.8 today.
Day 13: Vital signs all normal; patient feels fine physically. Tumor: Patient reports retrosternal pain has disappeared.
Day 14: Vital signs all normal; blood parameters normal, including serum total protein level. Tumor: Patient reports coughing episodes are now minimal.
Day 15: Patient reports feeling of well-being and great improvement; appetite has increased. Tumor: Patient reports coughing has completely stopped; retrosternal pain is gone; no shortness of breath even with active walking; blood urea nitrogen level has decreased relative to pretreatment level.

The oncologist noted the following: Throughout the treatment the patient's body weight, blood pressure, pulse rate, respiratory rate, temperature, and blood cytological and chemical parameters remained stable and within the normal range. The DNP produced the intended transient decrease in metabolic rate. No side effects due to the DNP per se were observed. The patient left the hospital soon after completion of the Phase I treatment period because of continuing family problems, and did not receive the Phase II treatment.

EXAMPLE 12

Example Case No. 12:
Female, 57 years old.
Diagnosis:
Adenocarcinoma (poorly differentiated; surgically unidentified primarily because of far advanced visceral spread); (clinically colon): numerous liver and other metastases.

Basis of Diagnosis:
Laparotomy with multiple biopsies; X-rays; scans.
Therapy Prior to Present Treatment:
Extensive semi-continuous conventional (mitoxin) chemotherapy over a prolonged period.
Tumor Status at Start of Present Therapy:
Extensive metastatic tumor activity throughout the body; brain, bones, viscera, liver (extensive metastases), both lungs, lymph nodes. Patient is in late terminal state; in intense general pain (headache, right chest, rib cage, abdomen, spine) even though under heavy sedation; has hypercalcemia; cannot maintain balance or walk; nausea; very weak; anorexic. (Note: Although this patient was clinically considered to be fully terminal, it was decided to attempt to administer the Phase I treatment to the extent that the DNR intake could continue to be reasonably maintained.

Response to Treatment:
Day 1: Patient starts on DNR; no DNP. Patient is in intense pain, especially headache; very restless; semi-confused; confined to bed; vital signs normal; blood parameters normal except moderate hypercalcemia.

Day 2: Patient taking DNR on schedule; no DNP; still feels very weak. Tumor: Headache has decreased in intensity.

Day 3: Patient is much improved; more alert and communicative; no DNP given yet. Tumor: Headache and other pain has diminished greatly; pain medication has been reduced to very low level.

Day 4: Patient in stable state; more cooperative; continues on DNR; starts on DNP. Tumor: Pain continues to diminish at all sites.

Day 5: Patient deemed to be improved sufficiently by oncologist to commence with daily palliative radiation treatments of large brain-metastasis tomorrow; serum calcium has decreased 11%. Tumor: Headache and other pains are essentially gone.

Day 7: Patient is less restless; slept well; vital signs all normal. Patient received first radiation treatment at noon; was very drowsy and semi-confused all afternoon. Tumor: Pain has disappeared at all sites; all pain medicine is stopped.

Day 9: Patient reports feeling much better in morning before radiation treatments; becomes tired, drowsy, confused, and uncooperative after radiation treatments. Tumor: Patient remains pain-free. Patient has been free of any clinical signs of hypercalcemia.

Day 10: Patient better oriented; much less confused; more cooperative; vital signs normal; resting metabolic rate has started increasing (1.26). No radiation treatment today. Tumor: Patient remains free of pain at all sites.

Day 11: Final day of treatment period; DNP discontinued yesterday. Patient greatly improved; is able to carry on coherent conversation with visitors; vital signs normal; resting metabolic rate has elevated to 1.99; no radiation today. Tumor: Patient continues free of pain.

Day 12: Patient is very alert and cooperative prior to radiation treatment; reports feeling very tired after radiation treatment; sleeps most of the afternoon; irritable. Tumor: No pain whatever.

Day 13. Patient requests discontinuance of daily radiation treatment, as she feels much better before treatment and very bad after it; continues to improve generally. Tumor: No pain at any level; no signs of hypercalcemia.

The oncologist noted the following: Throughout the treatment period the patient's body weight, blood pressure, pulse rate, respiratory rate, temperature, and blood cytological and chemical parameters remained stable within the normal range, except for the increasing initial hypercalcemia she had at time of entry. The DNP produced the intended transient increase in metabolic rate; no side effects attributable to DNP per se were observed. The patient was continued on daily radiation treatments by the oncologist for another week after her request that they be stopped. Just prior to the last radiation treatment (Day 19) the patient slipped in the bathroom at night and suffered an orbital hematoma, with apparent additional internal bleeding of undetermined origin, and eventually became comatose therefrom (Day 24). However, she responded rapidly to an infusion of whole blood and improved somewhat, but remained in a state of general malaise and unsteadiness. The hypercalcemic state elevated rapidly during this period, when she was only minimally on the DNR. She was released (Day 27) at the request of her family and did not participate in the Phase II treatment period.

The following Example 13 demonstrates the dramatic rate and extent of oncolysis that are achievable in human cancer patients with otherwise totally refractory malignant neoplasms by use of the present invention. In this case the clinical regimen consisted of a Phase I treatment period only, of 15-day duration. The patient was administered a DNR-AAB-AAD combination of metabolic effectors, wherein the AAD was the O/P uncoupling agent 2,4-Dinitrophenol (DNP) and the AAB was aminoglutethimide (AGT). However, the patient in effect also had an effective FAB acting, in the form of an indigenous enzyme deficiency which precluded $\beta$-oxidation of endogenous free fatty acids at a significant rate.

EXAMPLE 13

Example Case No. 13:
Female, 46 years old.
Diagnosis:
Infiltrating ductal cell carcinoma of left breast; four out of 10 axillary lymph nodes positive for carcinoma.
Basis of Diagnosis:
Multiple biopsy specimens and histological analyses.
Therapy Prior to Present Treatment:
Modified radical mastectomy of left breast, followed by multiagent mitoxin chemotherapy (Cytoxan, Methotrexate, 5-Fluorouracil); patient asymptomatic for four years before recurrence; multiple subcutaneous erythematous tumor nodules recurred along previous mastectomy scar; received intense radiotherapy with Cobalt-60, along with combination Adriamycin and Vincristine mitoxin chemotherapy; disease continued to progress; patient deemed terminal.
Tumor Status at Start of Present Therapy:
Numerous isolated areas of subcutaneous tumor covered by erythematous skin spread over left chest wall and under left arm; new nodules appearing daily and initial lesion sites expanding rapidly; some tumor patches 3 to 5 cm in extent. Cortisol level 22 $\mu$g/dl.
Response to Treatment:
Day 1: Patient started on DNR and received AM and PM doses of DNP adequate to elevate the resting metabolic rate to 3.0 (times basal) in two days, to effect a high level of ATP wastage; daily aminogluethethimide (AGT) administration commenced.

Day 3: Patient's resting metabolic rate rose to and remained at 3.2 (times basal) over a 24-hour period yesterday, following which DNP was suspended for a period of 4 days; regression of all lesions discernable already on Day 3. Patient is consuming all of administered DNR despite high caloric level at high therapeutical resting metabolic rates.

Day 7: Pronounced regression in all tumor areas; all inflammatory areas and patches fading; estimated reduction in overall tumor burden approximately 40%; DNP administration recommenced.

Day 9: Resting metabolic rate rose to and remained at 3.0 over a 24-hour period yesterday. Overall tumor reduction estimated to be 50% on Day 9. DNP administration suspended for two days.

Day 11: DNR administration recommenced. Overall tumor reduction estimated to be 70%.

Day 13: Resting metabolic rate rose to and remained at 3.2 over a 24-hour period yesterday. DNR administration suspended. Overall tumor reduction estimated to be 90%.

Day 15: Patient in excellent condition. Attending oncologists report 100% reduction of tumors and inflammation areas.

Day 20: Attending oncologists declare patient to be in complete remission and clinically free of discernable cancer. Patient's cortisol level 7 μg/dl.

This remarkable result occurred from just three 24-hour duration elevations of the resting metabolic rate (to ~3.0) with the AAD (DNP) within a 15-day period, and the AAB (AGT), which was administered daily throughout the total 15-day period. However, as cited previously, this patient was found to possess a substantial deficiency in ability to oxidize fatty acids at an appreciable rate, demonstrating the classical symptoms of Fatty Acid Oxidation Deficiency Syndrome associated with a genetic deficiency of the enzyme carnitine palmitoyl transferase required for transport of fatty acids into cellular mitochondria (see e.g., Cumming, W. J. K. et al., *Journal of the Neurological Sciences* 30, 247 (1976)). Consequently, she also had, in effect, a very effective (indigenous) FAB simultaneously acting with the administered AAD-AAB-DNR.

The following Example 14 comprises a clinical case in which only the AAD metabolic effector was administered to the patient in order to effect oncolysis. This example is particularly interesting in that it demonstrates the powerful rate and extent of malignant neoplasm regression that can be effected with only the AAD of the present therapy system, when administered rapidly and in adequate intensity relative to the rate at which the cancer cells can generate ATP. It also represents a case where the AAD is a "means" or "procedure" (i.e., a nutritionally mediated protein intake depression/elevation cycle) rather than a substance or agent per se. In this case the AAD utilized the physiologically well-known ability of protein intake depression/sudden elevation to temporarily raise the body-resting metabolic rate to very appreciable levels (>3×basal). This phenomenon is ostensibly mediated by a gross (inappropriate) stimulation of a wide range of anabolic and other cellular ATPases by a sudden pronounced availability of amino acids, following an extended period of relative starvation of amino acids. The sudden and pronounced increase in the rate of use-up of ATP by the ATPases in the cancer cells mediated by the amino acid starvation/restoration cycle far exceeds the very limited ATP supply rate capability ($ATP_A$) under such elevated body metabolic rate conditions, whence the cells rapidly succumb because of energy starvation (i.e., by $ATP_L$). In principle, the AAD in this example acts through inappropriate stimulation of cellular ATPase similarly to thyroid hormone's stimulation of the $Na^+/K^+$-dependent membrane ATPases of the $Na^+$-pump, but to a much broader and more pronounced degree. However, due to the high whole-body resting metabolic rates generated, and the imprecision of controllability of their maximum level and duration, this procedure is not preferred for general use in the present therapy system.

EXAMPLE 14

Example Case No. 14:
Male, 32 years old.
Diagnosis:
Malignant melanoma. Metastatic disease following malignant skin mole excision two years previously. Disease Stage 3.
Basis of Diagnosis:
Initial histological analysis of excised (mole) lesion from right forearm below elbow; present needle biopsies and histological analyses of large lung metastasis and of large (3.4 cm×2.9 cm) tumor mass in lower right neck.
Therapy Prior to Present Treatment:
Surgical excision only.
Tumor Status at Start of Present Therapy:
Large (3.4 cm×2.9 cm) hard, firmly fixed, metastatic mass in lower right neck region; large metastasis in lower lobe of left lung, with two smaller metastases in right lung. Neck and left lung masses proven melanoma metastases by direct biopsy and histological analyses. Neck mass was protrusive and easily measurable. Patient in reasonably good health, but losing weight; neck mass is rapidly increasing in size.
Response to Treatment:
For eight days prior to start of therapy (Day 1 is first day of protein elevation), patient remains on a regular food (vegetarian) diet, but daily protein intake is reduced to 5 g per 70 Kg of body weight or less, by elimination of protein-containing food items (e.g., meats, milk, eggs, et cetera). No medications of any sort are given. Patient's balanced caloric intake is 648 Kcal/d. Resting metabolic rate is 1.01 times Mayo standard basal metabolic rate. On the eighth day before Day 1, just prior to dietary protein restriction, the following enzyme levels were measured: SGOT (aspartate aminotransferase)=117 U/L [Normal range: 0–40]; SGPT (alanine aminotransferase) 113 U/L [Normal range: range: 100–240].

Day 1: Patient's dietary protein intake increased to 40 g/70 Kg per day; otherwise, diet remains the same as for the past eight days. Patient will remain on this increased protein intake for the next five days. AM (8:00) resting metabolic rate is 1.02 (x basal). PM (4:30) resting metabolic rate has risen to 1.70.

Day 2: AM resting metabolic rate has risen to 2.01; dietary caloric intake is increased accordingly, for caloric balance. PM resting metabolic rate has increased to 2.40. Patient feels fine. Blood pressure, pulse rate, temperature, and respiration rate are normal.

Day 3: AM resting metabolic rate has increased to 2.71. Dietary caloric intake is increased to the equivalent of an overall (effective) metabolic rate level of 2.30, which is the maximum the patient can consume orally; he is consequently in negative dietary caloric balance at this point. Right neck mass (AM) is now quite soft, movable, smaller. PM resting metabolic rate has risen still further to 3.21. Patient feels fine. Blood pressure and temperature normal; pulse rate and respiratory rate slightly elevated.

Day 4: AM resting metabolic rate has decreased to normal level of 1.06. Neck tumor has decreased 64% in mass (volume) in three days; is soft and pliable, non-fixed. Patient feels fine. Blood pressure, pulse rate, temperature, and respiration rate are all normal. Patient continues on regular diet with high protein, calorically balanced to an effective metabolic rate of 1650 Kcal/d. LDH has risen to 261 U/L (from 184 U/L before protein restriction began), a 42% increase.

Day 7: Resting metabolic rate has remained at approximately 1.00×basal since Day 4. Body weight has remained constant; daily blood pressure, pulse rate, temperature and respiratory rate have been normal. Neck tumor has decreased 87% in mass since Day 1. Patient is in excellent condition. SGOT has decreased to 22 U/L (81% decline) and SGPT to 54 U/L (52% decline).

EXAMPLE 15

Types of Malignancies Demonstrating Clinical Oncolysis in Response to Therapy System of Present Invention

| Types of Malignancies Demonstrating Clinical Oncolysis in Response to Therapy System of Present Invention | | | |
| --- | --- | --- | --- |
| Patient | Sex | Age | Malignant Neoplasm |
| A | F | 52 | Tongue |
| B | M | 57 | Throat |
| C | M | 70 | Stomach |
| D | F | 47 | Cecum |
| E | F | 54 | Colon |
| F | M | 67 | Rectum |
| G | F | 45 | Breast |
| H | F | 57 | Ovary |
| I | F | 60 | Uterus |
| J | M | 65 | Lung |
| K | M | 65 | Kidney |
| L | M | 59 | Prostate |
| M | M | 49 | Pancreas |
| N | M | 49 | Lymphoma |
| O | M | 47 | Melanoma |
| P | F | 48 | Skin: basal cell |
| Q | M | 66 | Leukemia |
| R | M | 50 | Bone: sarcoma |

The foregoing representative cases illustrate the 18 types of malignant neoplasms whose oncolytic responsiveness to administration of the present therapy system has been evaluated clinically. These 18 types embrace almost all malignant neoplasm forms of major clinical frequency. In every malignancy form evaluated to date, significant oncolysis has been observed, thus demonstrating the clinical validity of the underlying physiological rationale of the present invention, and verifying the results of the voluminous previous findings that malignantly transformed cells of essentially all forms of neoplasms do indeed possess a common metabolic aberrancy, vis. the inability to substantially metabolize glucose for energy purposes beyond the pyruvate stage of the Embden-Meyerhof Pathway under in vivo conditions. Of the 54 advanced-malignancy patients evaluated to date with the present therapy system, the great majority have demonstrated significant oncolysis, while essentially all the rest have experienced at least an arrest of progression of their disease during the treatment period.

While the invention has been described in connection with specific embodiments thereof, it will be understood that it is capable of further modification and that this application is intended to cover any variations, uses, or adaptations of the invention following, in general, the principles of the invention and including such departures from the present disclosure as come within the ordinary skill of the art to which the invention pertains, and as may be applied to the essential features hereinbefore set forth, within the spirit of the invention and the scope of the appended claims.

What is claimed is:

1. A method for effecting in a human or other mammal oncolysis of a malignant neoplasm wherein the malignant cells of said neoplasm are characterized by an in vivo metabolism in which said cells are substantially incapable of utilizing glucose-derived energy for the production of adenosine triphosphate (ATP) by the Citric Acid Cycle-Respiratory Chain oxidative pathway, which method comprises administering an effective amount of an ATP-availability depressor agent for limiting the overall rate of ATP energy availability for supporting the metabolism of the malignant cells.

2. The method of claim 1 wherein the ATP-availability depressor agent is selected from the group consisting of that
   (a) which inhibits the rate of ATP production;
   (b) which wastefully hydrolyzes ATP;
   (c) which inhibits participation of ATP in cellular energy metabolism; and
   (d) combinations thereof.

3. The method of claim 2 wherein the ATP-availability depressor agent is one whose intracellular concentration and intensity of action are substantially unaltered by changes in the intracellular pH within the range of about pH 5.0 to about pH 7.5.

4. The method of claim 2 wherein the agent which inhibits ATP production is an oxidative phosphorylation uncoupling agent having a $pK_a$ greater than or equal to about 7.0.

5. The method of claim 2 wherein the agent which wastefully hydrolyzes ATP is thyroid hormone.

6. The method of claim 4 wherein the ATP-availability depressor agent is selected from the group consisting of 4-nitrophenol, 4-chlorophenol, phenylhydrazonocyanoacetic acid methyl ester, (3-chlorophenylhydrazono)cyanoacetic acid methyl ester, 5-chlorotrifluoromethyl benzimidazole, and combinations thereof.

7. The method of claim 6 further comprising mitoxin chemotherapy, immunotherapy, radiotherapy, hyperthermotherapy, surgery or a combination thereof.

8. The method of claim 6 wherein said agent is administered orally or parenterally.

9. The method of claim 3 wherein the ATP-availability depressor agent is thyroid hormone.

10. The method of claim 9 further comprising mitoxin chemotherapy, immunotherapy, radiotherapy, hyperthermotherapy, surgery or a combination thereof.

11. The method of claim 9 wherein said agent is administered orally or parenterally.

12. The method of claim 1 further comprising mitoxin chemotherapy, immunotherapy, radiotherapy, hyperthermotherapy, surgery or combination thereof.

13. The method of claim 1 wherein said agent is administered orally or parenterally.

14. A method for effecting in a human or other mammal oncolysis of a malignant neoplasm wherein the malignant cells of said neoplasm are characterized by an in vivo metabolism in which said cells are substantially incapable of utilizing glucose-derived energy for the production of ATP by the Citric Acid Cycle-Respiratory Chain oxidative pathway, which method comprises the concurrent administration of
  (a) an effective amount of an ATP-availability depressor agent for limiting the overall rate of ATP energy availability for supporting the metabolism of the malignant cells; and
  (b) an effective amount of a lactate export blocking agent for limiting the rate at which lactic acid is exported from the malignant cells.

15. The method of claim 14 wherein the lactate export blocking agent is one or more of the natural plant bioflavonoids, selected from one group consisting of 5,7,4'-trihydroxyflavone, 3,7,3',4'-quadrahydroxy-flavone, 3,5,7,2',4'-pentahydroxyflavone, 5,7,4'-trihydroxy-3,6-OCH3-flavone, 5,7,3'-trihydroxy- 3,6,4'-OCH-flavone and 3,5,7,3',4'-pentahydroxyflavone.

16. The method of claim 15 wherein the intracellular concentration and intensity of action of said ATP-availability depressor agent are substantially unaltered by changes in the intracellular pH within the range of about pH 5.0 to about pH 7.5 and the ATP-availability depressor agent is substance or selected from the group consisting of that
  (a) which inhibits the rate of ATP production;
  (b) which wastefully hydrolyzes ATP;
  (c) which inhibits participation of ATP in cellular energy metabolism; and
  (d) combinations thereof.

17. The method of claim 16 wherein the agent which inhibits ATP production is an oxidative phosphorylation uncoupling agent having a $pK_a$ greater than or equal to about 7.0.

18. The method of claim 16 wherein the agent which wastefully hydrolyzes ATP is thyroid hormone.

19. The method of claim 17 wherein the ATP-availability depressor agent is selected from the group consisting of 4-nitrophenol, 4-chlorophenol, phenylhydrazonocyanoacetic acid methyl ester, (3-chlorophenylhydrazono)cyanoacetic acid methyl ester, 5-chlorotrifluoromethyl benzimidazole, and combinations thereof.

20. The method of claim 18 wherein the lactate export blocking agent is 3,5,7,3'4'-pentahydroxyflavone.

21. The method of claim 20 further comprising mitoxin chemotherapy, immunotherapy, radiotherapy, hyperthermotherapy, surgery or a combination thereof.

22. The method of claim 20 wherein said agent is administered orally or parenterally.

23. The method of claim 14 further comprising mitoxin chemotherapy, immunotherapy, radiotherapy, hyperthermotherapy, surgery or a combination thereof.

24. The method of claim 14 wherein any of said agents is administered orally or parenterally.

25. A method for effecting in a human or other mammal oncolysis of a malignant neoplasm wherein the malignant cells of said neoplasm are characterized by an in vivo metabolism in which said cells are substantially incapable of utilizing glucose-derived energy for the production of ATP by the Citric Acid Cycle-Respiratory Chain oxidative pathway, which method comprises the concurrent administration of
  (a) an effective amount of an ATP-availability depressor agent for limiting the overall rate of ATP energy availability for supporting the metabolism of the malignant cells;
  (b) an effective amount of a lactate export blocking agent for limiting the rate at which lactic acid is exported from the malignant cells; and
  (c) one or more metabolic effectors selected from the group consisting of:
    (1) an effective amount of a defined nutritional regimen for limiting the amount of exogenously derived free fatty acids and amino acids available to the malignant cells while providing calorically adequate glucose for normal cell metabolism;
    (2) an effective amount of a fatty acid blocking agent for limiting the rate of availability of energy to the malignant cells from endogenously derived free fatty acids; and
    (3) an effective amount of an amino acid blocking agent for limiting the rate of availability of energy to the malignant cells from endogenously derived amino acids.

26. The method of claim 25 the lactate export blocking agent is one or more of the natural plant bioflavonoids, selected from one group consisting of 5,7,4'-trihydroxyflavone, 3,7,3',4'-quadrahydroxy-pentahydroxyflavone, 3,6-OCH3-flavone, 5,7,3,-trihydroxy- 3,6,4'-OCH-flavone and 3,5,7,3',4'-pentahydroxyflavone.

27. The method of claim 26 wherein the intracellular concentration and intensity of action of said ATP-availability depressor agent are substantially unaltered by changes in the intracellular pH within the range of about pH 5.0 to about pH 7.5 and wherein the ATP-availability depressor agent is selected from the group consisting of that
  (a) which inhibits the rate of ATP production;
  (b) which wastefully hydrolyzes ATP;
  (c) which inhibits participation of ATP in cellular energy metabolism; and
  (d) combinations thereof.

28. The method of claim 27 wherein the agent which inhibits ATP production is an oxidative phosphorylation uncoupling agent having a $pK_a$ greater than or equal to about 7.0.

29. The method of claim 27 wherein the agent which wastefully hydrolyzes ATP is thyroid hormone.

30. The method of claim 28 wherein the ATP-availability depressor agent is selected from the group consisting of 4-nitrophenol, 4-chlorophenol, phenylhydrazonocyanoacetic acid methyl ester, (3-chlorophenylhydrazono)cyanoacetic acid methyl ester, 5-chlorotrifluoromethyl benzimidazole, and combinations thereof.

31. The method of claim 27 wherein the lactate export blocking agent is 3,5,7,3',4'-pentahydroxyflavone.

32. The method of claim 27 wherein the defined nutritional regimen provides an amount of amino acids supplying a daily nitrogen intake substantially equal to the minimum total daily nitrogen excreted in urine and a minimum amount of essential fatty acids corresponding to about 1% of the daily caloric requirement at the commencement of administration of the method.

33. The method of claim 32 wherein the daily caloric requirement of the defined nutritional regimen expressed as kilocalories per day is measured at about one-half the sum of resting and active metabolic rates, each expressed in kilocalories per day.

34. The method of claim 27 wherein said fatty acid blocking agent is selected from the group consisting of that
    (a) which inhibits fatty acid mobilization;
    (b) which inhibits fatty acid transport;
    (c) which inhibits fatty acid metabolism, and
    (d) combinations thereof.

35. The method of claim 34 wherein the fatty acid blocking agent is selected from the group consisting of insulin, 2-tetradecylglycidic acid, methyl 2-tetradecylglycidate, and mixtures thereof.

36. The method of claim 35 wherein the insulin is lente insulin with an active duration of 18 hours or greater.

37. The method of claim 27 wherein the amino acid blocking agent is thyroid hormone, aminoglutethimide or both.

38. The method of claim 27 wherein said amino acid blocking agent reduces or enhances reduction of plasma cortisol levels, whereby chronically elevated plasma cortisol levels are lowered to within the normal concentration range of the daily cycle.

39. The method of claim 38 wherein said amino acid blocking agent is a stress-relieving said amino acid blocking agent is a stress-relieving psychotherapy regimen.

40. The method of claim a defined nutritional regimen is administered and wherein the ATP-availability depressor agent and the amino acid blocking agent are both thyroid hormone, the fatty acid blocking agent is lente insulin, and the lactate export blocking agent is quercetin.

41. The method of claim wherein the thyroid hormone is administered orally daily in an amount physiologically equivalent to 0.5 to 5.0 grains of pharmacologically standard desiccated thyroid gland, the lente insulin is of substantially 16- to 20-hour active duration and is administered by intramuscular injection daily in an amount of 5.0 to 50.0 I.U., and the pure quercetin is administered orally at twelve hour intervals in the amount of 1.5 to 8.0 milligrams per kilogram of body weight per administration.

42. The method of claim 40 further comprising mitoxin chemotherapy, immunotherapy, radiotherapy, hyperthermotherapy, surgery or a combination thereof.

43. The method of claim 40 wherein said agent is administered orally or parenterally.

44. The method of claim 25 further comprising mitoxin chemotherapy, immunotherapy, radiotherapy, hyperthermotherapy, surgery or a combination thereof.

45. The method of claim 25 wherein any of said agents is administered orally or parenterally.

46. A method for effecting in a human or other mammal oncolysis of a malignant neoplasm wherein the malignant cells of said neoplasm are characterized by an in vivo metabolism in which said cells are substantially incapable of utilizing glucose-derived energy for the production of ATP by the Citric Acid Cycle-Respiratory Chain oxidative pathway, which method comprises the concurrent administration of
    (a) an effective amount of an ATP-availability depressor agent for limiting the overall rate of ATP energy availability for supporting the metabolism of the malignant cells;
    (b) an effective amount of a defined nutritional regimen for limiting the amount of exogenously derived free fatty acids and amino acids available to the malignant cells while providing calorically adequate glucose for normal cell metabolism;
    (c) an effective amount of a fatty acid blocking agent for limiting the rate of availability of energy to the malignant cells from endogenously derived free fatty acids;
    (d) an effective amount of an amino acid blocking agent for limiting the rate of availability of energy to the malignant cells from endogenously derived amino acids; and
    (e) an effective amount of a lactate export blocking agent for limiting the rate at which lactic acid is exported from the malignant cells.

47. The method of claim 46 wherein the lactate export blocking agent is one or more of the natural plant bioflavonoids, selected from one group consisting of 5,7,4'-trihydroxyflavone, 3,7,3',4'-quadrahydroxyflavone, 3,5,7,2',4'-pentahydroxyflavone, 5,7,4'-trihydroxy-3,6-OCH$_3$-flavone, 5,7,3'-trihydroxy-3,6,4'-OCH-flavone and 3,5,7,3',4'-pentahydroxyflavone.

48. The method of claim 47 wherein the intracellular concentration and intensity of action of said ATP-availability depressor agent are substantially unaltered by changes in the intracellular pH within the range of pH 5.0 to about pH 7.5 and wherein the ATP-availability depressor agent is selected from the group consisting of that
    (a) which inhibits the rate of ATP production;
    (b) which wastefully hydrolyzes ATP;
    (c) which inhibits participation of ATP in cellular energy metabolism; and
    (d) combinations thereof.

49. The method of claim 48 wherein the agent which inhibits ATP production is an oxidative phosphorylation uncoupling agent having a pK$_a$ greater than or equal to about 7.0.

50. The method of claim 48 wherein the agent which wastefully hydrolyzes ATP is thyroid hormone.

51. The method of claim the ATP-availability depressor agent is selected from the group consisting of 4-nitrophenol, 4-chlorophenol, phenylhydrazonocyanoacetic acid methyl ester, (3-chlorophenylhydrazono)-cyanoacetic acid methyl ester, 5-chlorotrifluoromethyl benzimidazole, and combinations thereof.

52. The method of claim 50 wherein the lactate export blocking agent is 3,5,7,3',4'-pentahydroxyflavone.

53. The method or claim 48 wherein the defined nutritional regimen provides an amount of amino acids supplying a daily nitrogen intake substantially equal to the minimum total daily nitrogen excreted in urine and a minimum amount of essential fatty acids corresponding to about 1% of the daily caloric requirement at the commencement of administration of the method.

54. The method of claim 53 the daily caloric requirement of the defined nutritional regimen expressed as kilocalories per day is measured at about one-half the sum of resting and active metabolic rates, each expressed in kilocalories per day.

55. The method of claim 48 wherein said fatty acid blocking agent is selected from the group consisting of that
    (a) which inhibits fatty acid mobilization;
    (b) which inhibits fatty acid transport;
    (c) which inhibits fatty acid metabolism, and
    (d) combinations thereof.

56. The method of claim 55 wherein the fatty acid blocking agent is selected from the group consisting of insulin, 2-tetradecylglycidic acid, methyl 2-tetradecylglycidate, and mixtures thereof.

57. The method of claim 56 wherein the insulin is lente insulin with an active duration of 18 hours or greater.

58. The method of claim 48 wherein the amino acid blocking agent is thyroid hormone, aminoglutethimide or both.

59. The method of claim 48 wherein said amino acid blocking agent reduces or enhances reduction of plasma cortisol levels, whereby chronically elevated plasma cortisol levels are lowered to within the normal concentration range of the daily cycle.

60. The method of claim 59 wherein said amino acid blocking agent is a stress-relieving psychotherapy regimen.

61. The method of claim 46 wherein a defined nutritional regimen is administered and wherein the ATP-availability depressor agent and the amino acid blocking agent are both thyroid hormone, the fatty acid blocking agent is lente insulin, and the lactate export blocking agent is quercetin.

62. The method of claim 61 wherein the thyroid hormone is administered orally daily in an amount physiologically equivalent to 0.5 to 5.0 grains of pharmacologically standard desiccated thyroid gland, the lente insulin is of substantially 16- to 20-hour active duration and is administered by intramuscular injection daily in an amount of 5.0 to 50.0 I.U., and the pure quercetin is administered orally at twelve hour intervals in the amount of 1.5 to 8.0 milligrams per kilogram of body weight per administration.

63. The method of claim 61 further comprising mitoxin chemotherapy, immunotherapy, radiotherapy, hyperthermotherapy, surgery or a combination thereof.

64. The method of claim 61 wherein said agent is administered orally or parenterally.

65. The method of claim 46 further comprising mitoxin chemotherapy, immunotherapy, radiotherapy, hyperthermotherapy, surgery or a combination thereof.

66. The method of claim 46 wherein any of said agents is administered orally or parenterally.

67. A method for effecting in a human or other mammal oncolysis of a malignant neoplasm wherein the malignant cells of said neoplasm are characterized by an in vivo metabolism in which said cells are substantially incapable of utilizing glucose-derived energy for the production of ATP by the Citric Acid Cycle-Respiratory Chain oxidative pathway, which method comprises the concurrent administration of (a) an effective amount of an ATP-availability depressor agent for limiting the overall rate of ATP energy availability for supporting the metabolism of the malignant cells, wherein said ATP-availability depressor agent is selected from the group consisting of that
  (1) which inhibits the rate of ATP production;
  (2) which wastefully hydrolyzes ATP;
  (3) which inhibits participation of ATP in cellular energy metabolism; and
  (4) combinations thereof; and
(b) one or more metabolic effectors selected from the group consisting of:
  (1) an effective amount of a defined nutritional regimen for limiting the amount of exogenously derived free fatty acids and amino acids available to the malignant cells while providing calorically adequate glucose for normal cell metabolism;
  (2) an effective amount of a fatty acid blocking agent for limiting the rate of availability of energy to the malignant cells from endogenously derived free fatty acids, wherein said fatty acid blocking agent is selected from the group consisting of that
    (i) which inhibits fatty acid mobilization;
    (ii) which inhibits fatty acid transport;
    (iii) which inhibits fatty acid metabolism, and
    (iv) combinations thereof;
  (3) an effective amount of an amino acid blocking agent for limiting the rate of availability of energy to the malignant cells from endogenously derived amino acids; and
  (4) an effective amount of a lactate export blocking agent for limiting the rate at which lactic acid is exported from the malignant cells,
with the proviso that (A) when the defined nutritional regimen is utilized as the only metabolic effector, then the ATP-availability depressor agent is not a substance which inhibits the rate of ATP production, and (B) when the defined nutritional regimen and an agent which inhibits either fatty acid metabolism or fatty acid transport are utilized as the only metabolic effectors, then the ATP-availability depressor agent is not a substance which inhibits the rate of ATP production.

68. The method of claim 68 wherein the ATP-availability depressor agent is one whose intracellular concentration and intensity of action are substantially unaltered by changes in the intracellular pH within the range of about pH 5.0 to about pH 7.5.

69. The method of claim 68 wherein the agent which inhibits ATP production is an oxidative phosphorylation uncoupling agent having a $pK_a$ greater than or equal to about 7.0.

70. The method of claim 68 wherein the agent which wastefully hydrolyzes ATP is thyroid hormone.

71. The method of claim 69 wherein the ATP-availability depressor agent is selected from the group consisting of 4-nitrophenol, 4-chlorophenol, phenylhydrazonocyanoacetic acid methyl ester, (3-chlorophenylhydrazono)cyanoacetic acid methyl ester, 5-chlorotrifluoromethyl benzimidazole, and combinations thereof.

72. The method of claim 70 wherein the lactate export blocking agent is 3, 7,3',4'-pentahydroxyflavone.

73. The method of claim 67 wherein the lactate export blocking agent is one or more of the natural plant bioflavonoids, selected from one group consisting of 5,7,4'-trihydroxyflavone, 3,7,3',4'-quadrahydroxyflavone, 3,5,7,2',4'-pentahydroxyflavone, 5,7,4'-trihydroxy-3,6-OCH$_3$-flavone, 5,7,3'-trihydroxy3,6,4'-OCH-flavone and 3,5,7,3',4'-pentahydroxyflavone.

74. The method of claim 67 wherein the defined nutritional regimen an amount of amino acids supplying a daily nitrogen intake substantially equal to the minimum total daily nitrogen excreted in urine and a minimum amount of essential fatty acids corresponding to about 1% of the daily caloric requirement at the commencement of administration of the method.

75. The method of claim 56 wherein the daily caloric requirement of the defined nutritional regimen expressed as kilocalories per day is measured at about one-half the sum of resting and active metabolic rates, each expressed in kilocalories per day.

76. The method of claim wherein the fatty acid blocking agent is selected from the group consisting of insulin, 2-tetradecylglycidic acid, methyl 2-tetradecylglycidate, and mixtures thereof.

77. The method of 76 wherein the insulin is lente insulin with an active duration of 18 hours or greater.

78. The method of claim 67 wherein the amino acid blocking agent is thyroid hormone, aminoglutethimide or both.

79. The method of claim 67 wherein said amino acid blocking agent reduces or enhances reduction of plasma cortisol levels, whereby chronically elevated plasma cortisol levels are lowered to within the normal concentration range of the daily cycle.

80. The method of claim 79 wherein said amino acid blocking agent is a stress-relieving psychotherapy regimen.

81. The method of claim 67 wherein a defined nutritional regimen is administered and wherein the ATP-availability depressor agent and the amino acid blocking agent are both thyroid hormone, the fatty acid blocking agent is lente insulin, and the lactate export blocking agent is quercetin.

82. The method of claim 81 wherein the thyroid hormone is administered orally daily in an amount physiologically equivalent to 0.5 to 5.0 grains of pharmacologically standard desiccated thyroid gland, the lente insulin is of substantially 16- to 20-hour active duration and is administered by intramuscular injection daily in an amount of 5.0 to 50.0 I.U., and the pure quercetin is administered orally at twelve hour intervals in the amount of 1.5 to 8.0 milligrams per kilogram of body weight per administration.

83. The method of claim 81 further comprising mitoxin chemotherapy, immunotherapy, radiotherapy, hyperthermotherapy, surgery or a combination thereof.

84. The method of claim 81 wherein said agent is administered orally or parenterally.

85. The method of claim 67 further comprising mitoxin chemotherapy, immunotherapy, radiotherapy, hyperthermotherapy, surgery or a combination thereof.

86. The method of claim 67 wherein any of said agents is administered orally/or parenterally.

87. A method for effecting in a human or other mammal oncolysis of a carcinoma of the tongue, throat, stomach, cecum, colon, rectum, breast, ovary, uterus, lung, kidney, prostate, pancreas, a melanoma, a basal cell carcinoma of the skin, a leukemia, a lymphoma, or an osteosarcoma, which method comprises administering an effective amount of an ATP-availability depressor agent for limiting the overall rate of ATP energy availability for supporting the metabolism of the malignant cells.

88. The method of claim 87 wherein the ATP-availability depressor agent is selected from the group consisting of that
 (a) which inhibits the rate of ATP production;
 (b) which wastefully hydrolyzes ATP;
 (c) which inhibits participation of ATP in cellular energy metabolism; and
 (d) combinations thereof.

89. The method of claim 88 wherein the ATP-availability depressor agent is one whose intracellular concentration and intensity of action are substantially unaltered by changes in the intracellular pH within the range of about pH 5.0 to about pH 7.5.

90. The method of claim 88 wherein the agent which inhibits ATP production is an oxidative phosphorylation uncoupling agent having a p$K_a$ greater than or equal to about 7.0.

91. The method of claim 89 the agent which wastefully hydrolyzes ATP is thyroid hormone.

92. The method of claim 90 wherein the ATP-availability depressor agent is selected from the group consisting of 4-nitrophenol, 4-chlorophenol, phenylhydrazonocyanoacetic acid methyl ester, (3-chlorotrifluoromethyl benzimidazole, and combinations thereof.

93. The method of claim 88 wherein the ATP-availability depressor agent is thyroid hormone.

94. The method of claim 93 further comprising mitoxin chemotherapy, immunotherapy, radiotherapy, hyperthermotherapy, surgery or a combination thereof.

95. The method of claim 93 wherein said agent is administered orally or parenterally.

96. The method of claim 92 further comprising mitoxin chemotherapy, immunotherapy, radiotherapy, hyperthermotherapy, surgery or a combination thereof.

97. The method of claim 92 wherein said agent is administered orally or parenterally.

98. The method of claim 87 further comprising mitoxin chemotherapy, immunotherapy, radiotherapy, hyperthermotherapy, surgery or a combination thereof.

99. The method of claim 87 wherein any of said agents is administered orally or parenterally.

100. A method for effecting in a human or other mammal oncolysis of a carcinoma of the tongue, throat, stomach, cecum, colon, rectum, breast, ovary, uterus, lung, kidney, prostate, pancreas, a melanoma, a basal cell carcinoma of the skin, a leukemia, a lymphoma, or an osteosarcoma, which method comprises the concurrent administration of
 (a) an effective amount of an ATP-availability depressor agent for limiting the overall rated of ATP energy availability for supporting the metabolism of the malignant cells; and
 (b) an effective amount of a lactate export blocking agent for limiting the rate at which lactic acid is exported from the malignant cells.

101. The method or claim the lactate export blocking agent is one or more or the natural plant bioflavonoids, selected from one group consisting of 5,7,4'-trihydroxyflavone, 3,7,3',4'-quadrahydroxyflavone, 3,5,7,2'4'-pentahydroxyflavone, 5,7,4'-trihydroxy-3,6-OCH$_3$-flavone, 5,7,3'-trihydroxy-3,6,4'-OCH-flavone and 3,5,7,3',4'-pentahydroxyflavone.

102. The method of claim wherein the intracellular concentration and intensity of action of said ATP-availability depressor agent are substantially unaltered by changes in the intracellular pH within the range of about pH 5.0 to about pH 7.5 and wherein the ATP-availability depressor agent is selected from the group consisting of that
 (a) which inhibits the rate of ATP production;
 (b) which wastefully hydrolyzes ATP;
 (c) which inhibits participation of ATP in cellular energy metabolism; and
 (d) combinations thereof.

103. The method of claim 102 wherein the agent which inhibits ATP production/ is an oxidative phosphorylation uncoupling agent having a p$K_a$ greater than or equal to about 7.0.

104. The method of claim 102 wherein the agent which wastefully hydrolyzes ATP is thyroid hormone.

105. The method of claim 103 wherein the ATP-availability depressor agent is selected from the group consisting of 4-nitrophenol, 4-chlorophenol, phenylhydrazonocyanoacetic acid methyl ester, (3-chlorophenylhydrazono)cyanoacetic acid methyl ester, 5-chlorotrifluoromethyl benzimidazole, and combinations thereof.

106. The method of claim 104 wherein the lactate export blocking agent is 3,5,7,3',4'-pentahydroxyflavone.

107. The method of claim 106 further comprising mitoxin chemotherapy, immunotherapy, radiotherapy, hyperthermotherapy, surgery or a combination thereof.

108. The method of claim 106 wherein said agent is administered orally or parenterally.

109. The method of claim 100 further comprising mitoxin chemotherapy, immunotherapy, radiotherapy, hyperthermotherapy, surgery or a combination thereof.

110. The method of claim 100 any of said agents is administered orally or parenterally.

111. A method for effecting in a human or other mammal oncolysis of a carcinoma of the tongue, throat, stomach, cecum, colon, rectum, breast, ovary, uterus, lung, kidney, prostate, pancreas, a melanoma, a basal cell carcinoma of the skin, a leukemia, a lymphoma, or an osteosarcoma, which method comprises the concurrent administration of (a) an effective amount of an ATP-availability depressor agent for limiting the overall rate of ATP energy availability for supporting the metabolism of the malignant cells;

(b) an effective amount of a lactate export blocking agent for limiting the rate at which lactic acid is exported from the malignant cells; and (c) one or more metabolic effectors selected from the group consisting of:
  (1) an effective amount of defined nutritional regimen for limiting the amount of exogenously derived free fatty acids and amino acids available to the malignant cells while providing calorically adequate glucose for normal cell metabolism;
  (2) an effective amount of a fatty acid blocking agent for limiting the rate of availability of energy to the malignant cells from endogenously derived free fatty acids; and
  (3) an effective amount of an amino acid blocking agent for limiting the rate of availability of energy to the malignant cells from endogenously derived amino acids.

112. The method of claim 111 wherein the lactate export blocking agent is one or more of the natural plant bioflavonoids, selected from one group consisting of 5,7,4'-trihydroxyflavone, 3,7,3',4'-quadrahydroxyflavone, 3,5,7,2',4'-pentahydroxyflavone, 5,7,4'-trihydroxy-3,6-OCH$_3$-flavone, 5,7,3'-trihydroxy-3,6,4'-OCH-flavone and 3,5,7,3',4'-pentahydroxyflavone.

113. The method of claim 112 wherein the intracellular concentration and intensity of action of said ATP-availability depressor agent are substantially unaltered by changes in the intracellular pH within the range of about pH 5.0 to about pH 7.5 and wherein the ATP-availability depressor agent is selected from the group consisting of that
(a) which inhibits the rate of ATP production;
(b) which wastefully hydrolyzes ATP;
(c) which inhibits participation of ATP in cellular energy metabolism; and
(d) combinations thereof.

114. The method of claim 113 wherein the agent which inhibits ATP production is an oxidative phosphorylation uncoupling agent having a pK$_a$ greater than or equal to about 7.0.

115. The method of claim 113 in the agent which wastefully hydrolyzes ATP is thyroid hormone.

116. The method of claim wherein the ATP-availability depressor agent is selected from the group consisting of 4-nitrophenol, 4-chlorophenol, phenylhydrazonocyanoacetic acid methyl ester, (3-chlorophenylhydrazono)cyanoacetic acid methyl ester, 5-chlorotrifluoromethyl benzimidazole, and combinations thereof.

117. The method of claim 115 wherein the lactate export blocking agent is 3,5,7,3',4'-pentahydroxyflavone.

118. The method of claim 113 wherein the defined nutritional regimen provides an amount of amino acids supplying a daily nitrogen intake substantially equal to the minimum total daily nitrogen excreted in urine and a minimum amount of essential fatty acids corresponding to about 1% of the daily caloric requirement at the commencement of administration of the method.

119. The method of claim 118 wherein the daily caloric requirement of the defined nutritional regimen expressed as kilocalories per day is measured at about one-half the sum of resting and active metabolic rates, each expressed in kilocalories per day.

120. The method of claim 113 wherein said fatty acid blocking agent is selected from the group consisting of that
(a) which inhibits fatty acid mobilization;
(b) which inhibits fatty acid transport;
(c) which inhibits fatty acid metabolism, and
(d) combinations thereof.

121. The method of claim 120 wherein the fatty acid blocking agent is selected from the group consisting of insulin, 2-tetradecylglycidic acid, methyl 2-tetradecylglycidate, and mixtures thereof.

122. The method of claim 121 wherein the insulin is lente insulin with an active duration of 18 hours or greater.

123. The method of claim 113 wherein the amino acid blocking agent is thyroid hormone, aminoglutethimide or both.

124. The method of claim 113 wherein said amino acid blocking agent reduces or enhances reduction of plasma cortisol levels, whereby chronically elevated plasma cortisol levels are lowered to within the normal concentration range of the daily cycle.

125. The method of claim 124 wherein said amino acid blocking agent is a stress-relieving psychotherapy regimen.

126. The method of claim 111 wherein a defined nutritional regimen is administered and wherein the ATP-availability depressor agent and the amino acid blocking agent are both thyroid hormone, the fatty acid blocking agent is lente insulin, and the lactate export blocking agent is quercetin.

127. The method of claim 126 wherein the thyroid hormone is administered daily in an amount physiologically equivalent to 0.5 to 5.0 grains of pharmacologically standard desiccated thyroid gland, the lente insulin is of substantially 16- to 20-hour active duration and is administered by intramuscular injection daily in an amount of 5.0 to 50.0 I.U., and the pure quercetin is administered orally at twelve hour intervals in the amount of 1.5 to 8.0 milligrams per kilogram of,; body weight per administration.

128. The method of claim 126 further comprising mitoxin chemotherapy, immunotherapy, radiotherapy, hyperthermotherapy, surgery or a combination thereof.

129. The method of claim 126 wherein said agent is administered orally or parenterally.

130. The method of claim 111 further comprising mitoxin chemotherapy, immunotherapy, radiotherapy, hyperthermotherapy, surgery or a combination thereof.

131. The method of claim 111 wherein any of said agents is administered orally or parenterally.

132. A method for effecting in a human or other mammal oncolysis of a carcinoma of the tongue, throat, stomach, cecum, colon, rectum, breast, ovary, uterus, lung, kidney, prostate, pancreas, a melanoma, a basal cell carcinoma of the skin, a leukemia, a lymphoma, or an osteosarcoma, which method comprises the concurrent administration of
(a) an effective amount of an ATP-availability depressor agent for limiting the overall rate of ATP energy availability for supporting the metabolism of the malignant cells;
(b) an effective amount of a defined nutritional regimen for limiting the amount of exogenously derived free fatty acids and amino acids available to the malignant cells while providing calorically adequate glucose for normal cell metabolism;
(c) an effective amount of a fatty acid blocking agent for limiting the rate of availability of energy to the malignant cells from endogenously derived free fatty acids;
(d) an effective amount of an amino acid blocking agent for limiting the rate of availability of energy to the malignant cells from endogenously derived amino acids; and
(e) an effective amount of a lactate export blocking agent for limiting the rate at which lactic acid is exported from the malignant cells.

133. The method of claim 132 wherein the lactate export blocking agent is one or more of the natural plant bioflavonoids, selected from one group consisting of 5,7,4'-trihydroxyflavone, 3,7,3',4'-quadrahydroxyflavone, 3,5,7,2',4'-pentahydroxyflavone, 5,7,4'-trihydroxy-3,6-OCH$_3$-flavone, 5,7,3'-trihydroxy-3,6,4'-OCH-flavone and 3,5,7,3',4'-pentahydroxyflavone.

134. The method of claim 133 wherein the intracellular concentration and intensity of action of said ATP-availability depressor agent are substantially unaltered by changes in the intracellular pH within the range of about pH 5.0 to about pH 7.5 and wherein the ATP-availability depressor agent is selected from the group consisting of that
(a) which inhibits the rate of ATP production;
(b) which wastefully hydrolyzes ATP;
(c) which inhibits participation of ATP in cellular energy metabolism; and
(d) combinations thereof.

135. The method of claim wherein the agent which inhibits ATP production is an oxidative phosphorylation uncoupling agent having a pK$_a$ greater than or equal to about 7.0.

136. The method of claim 134 wherein the agent which wastefully hydrolyzes ATP is thyroid hormone.

137. The method of claim 135 wherein the ATP-availability depressor agent is selected from the group consisting of 4-nitrophenol, 4-chlorophenol, phenylhydrazonocyanoacetic acid methyl ester, (3-chlorophenylhydrazono)cyanoacetic acid methyl ester, 5-chlorotrifluoromethyl benzimidazole, and combinations thereof.

138. The method of claim 136 wherein the lactate export blocking agent is 3,5,7,3',4'-pentahydroxyflavone.

139. The method of claim 134 wherein the defined nutritional regimen provides an amount of amino acids supplying a daily nitrogen intake substantially equal to the minimum total daily nitrogen excreted in urine and a minimum amount of essential fatty acids corresponding to about 1% of the daily caloric requirement at the commencement of administration of the method.

140. The method of claim 139 wherein the daily caloric requirement of the defined nutritional regimen expressed as kilocalories per day is measured at about one-half the sum of resting and active metabolic rates, each expressed in kilocalories per day.

141. The method of claim 134 wherein said fatty acid blocking agent is a substance or procedure selected from the group consisting of that
(a) which inhibits fatty acid mobilization;
(b) which inhibits fatty acid transport;
(c) which inhibits fatty acid metabolism, and
(d) combination thereof.

142. The method of claim 141 wherein the fatty acid blocking agent is selected from the group consisting of insulin, 2-tetradecylglycidic acid, methyl 2-tetradecylglycidate, and mixtures thereof.

143. The method of claim 142 wherein the insulin is lente insulin with an active duration of 18 hours or greater.

144. The method of claim 134 wherein the amino acid blocking agent is thyroid hormone, aminoglutethimide or both.

145. The method of claim 134 wherein said amino acid blocking agent reduces or enhances reduction of plasma cortisol levels, whereby chronically elevated plasma cortisol levels are lowered to within the normal concentration range of the daily cycle.

146. The method of claim 145 wherein said amino acid blocking agent is a stress-relieving psychotherapy regimen.

147. The method of claim 132 wherein a defined nutritional regimen is administered and wherein the ATP-availability depressor agent and the amino acid blocking agent are both thyroid hormone, the fatty acid blocking agent is lente insulin, and the lactate export blocking agent is quercetin.

148. The method of claim 147 the thyroid hormone is administered orally daily in an amount physiologically equivalent to 0.5 to 5.0 grains of pharmacologically standard desiccated thyroid gland, the lente insulin is of substantially 16- to 20-hour active duration and is administered by intramuscular injection daily in an amount of 5.0 to 50.0 I.U., and the pure quercetin is administered orally at twelve hour intervals in the amount of 1.5 to 8.0 milligrams per kilogram of body weight per administration.

149. The method of claim 147 further comprising mitoxin chemotherapy, immunotherapy, radiotherapy, hyperthermotherapy, surgery or a combination thereof.

150. The method of claim 147 wherein said agent is administered orally or parenterally.

151. The method of claim 132 further comprising mitoxin chemotherapy, immunotherapy, radiotherapy, hyperthermotherapy, surgery or a combination thereof.

152. The method of claim 132 wherein any of said agents is administered orally or parenterally.

153. A method for effecting in a human or other mammal oncolysis of a carcinoma of the tongue, throat, stomach, cecum, colon, rectum, breast, ovary, uterus, lung, kidney, prostate, pancreas, a melanoma, a basal cell carcinoma of the skin, a leukemia, a lymphoma, or an osteosarcoma, which method comprises the concurrent administration of
  (a) an effective amount of an ATP-availability depressor agent for limiting the overall rate of ATP energy availability for supporting the metabolism of the malignant cells, wherein said ATP-availability depressor agent is selected from the group consisting of that
    (1) which inhibits the rate of ATP production;
    (2) which wastefully hydrolyzes ATP;
    (3) which inhibits participation of ATP in cellular energy metabolism; and
    (4) combinations thereof; and
  (b) one or more metabolic effectors selected from the group consisting of:
    (1) an effective amount of a defined nutritional regimen for limiting the amount of exogenously derived free fatty acids and amino acids available to the malignant cells while providing calorically adequate glucose for normal cell metabolism;
    (2) an effective amount of a fatty acid blocking agent for limiting the rate of availability of energy to the malignant cells from endogenously derived free fatty acids, wherein said fatty acid blocking agent is selected from the group consisting of that
      (i) which inhibits fatty acid mobilization;
      (ii) which inhibits fatty acid transport;
      (iii) which inhibits fatty acid metabolism, and
      (iv) combinations thereof;
    (3) an effective amount of an amino acid blocking agent for limiting the rate of availability of energy to the malignant cells from endogenously derived amino acids; and
    (4) an effective amount of a lactate export blocking agent for limiting the rate at which lactic acid is exported from the malignant cells,
  with the proviso that (A) when the defined nutritional regimen is utilized as the only metabolic effector, then the ATP-availability depressor agent is not a substance which inhibits the rate of ATP production, and (B) when the defined nutritional regimen and an agent which inhibits either fatty acid metabolism or fatty acid transport are utilized as the only metabolic effectors, then the ATP-availability depressor agent is not a substance which inhibits the rate of ATP production.

154. The method of claim 153 wherein the ATP-availability depressor agent is one whose intracellular concentration and intensity of action are substantially unaltered by changes in the intracellular pH within the range of about pH 5.0 to about pH 7.5.

155. The method of claim 154 wherein the agent which inhibits ATP production is an oxidative phosphorylation uncoupling agent having a p$K_a$ greater than or equal to about 7.0.

156. The method of claim 154 wherein the agent which wastefully hydrolyzes ATP is thyroid hormone.

157. The method of claim 155 wherein the ATP-availability depressor agent is selected from the group consisting of 4-nitrophenol, 4-chlorophenol, phenylhydrazonocyanoacetic acid methyl ester, (3-chlorophenylhydrazono)cyanoacetic acid methyl ester, 5-chlorotrifluoromethyl benzimidazole, and combinations thereof.

158. The method of claim 156 wherein the lactate export blocking agent is 3,5,7,3',4'-pentahydroxyflavone.

159. The method of claim 153 wherein the lactate export blocking agent is one or more of the natural plant bioflavonoids, selected from one group consisting of 5,7,4'-trihydroxyflavone, 3,7,3',4'-quadrahydroxyflavone, 3,5,7,2',4'-pentahydroxyflavone, 5,7,4'-trihydroxy-3,6-OCH$_3$-flavone 5,7,3'-trihydroxy-3,6,4'-OCH-flavone and 3,5,7,3',4'-pentahydroxy-flavone.

160. The method of claim 153 wherein the defined nutritional regimen provides an amount of amino acids supplying a daily nitrogen intake substantially equal to the minimum total daily nitrogen excreted in urine and a minimum amount of essential fatty acids corresponding to about 1% of the daily caloric requirement at the commencement of administration of the method.

161. The method of claim 160 wherein the daily caloric requirement of the defined nutritional regimen expressed as kilocalories per day is measured at about one-half the sum of resting and active metabolic rates, each expressed in kilocalories per day.

162. The method of claim 153 wherein the fatty acid blocking agent is selected from the group consisting of insulin, 2-tetradecylglycidic acid, methyl 2-tetradecylglycidate, and mixtures thereof.

163. The method of claim 162 insulin with an active duration of 18 hours or greater.

164. The method of wherein the amino acid blocking agent is thyroid hormone, aminoglutethimide or both.

165. The method of claim 153 wherein said amino acid blocking agent reduces or enhances reduction of plasma cortisol levels, whereby chronically elevated plasma cortisol levels are lowered to within the normal concentration range of the daily cycle.

166. The method of claim 165 wherein said amino acid blocking agent is a stress-relieving psychotherapy regimen.

167. The method of claim 153 wherein a defined nutritional regimen is a and wherein the ATP-availability depressor agent and the amino acid blocking agent are both thyroid hormone, the fatty acid blocking agent is lente insulin, and the lactate export blocking agent is quercetin.

168. The method of claim 167 wherein the thyroid hormone is administered orally daily in an amount physiologically equivalent to 0.5 to 5.0 grains of pharmacologically standard desiccated thyroid gland, the lente insulin is of substantially 16- to 20-hour active duration and is administered by intramuscular injection daily in an amount of 5.0 to 50.0 I.U., and the pure quercetin is administered orally at twelve hour intervals in the amount of 1.5 to 8.0 milligrams per kilogram of body weight per administration.

169. The method of claim 167 further comprising mitoxin chemotherapy, immunotherapy, radiotherapy, hyperthermotherapy, surgery or a combination thereof.

170. The method of claim 167 wherein said agent is administered orally or parenterally.

171. The method of claim 153 further comprising mitoxin chemotherapy, immunotherapy, radiotherapy, hyperthermotherapy, surgery or a combination thereof.

172. The method of claim 153 wherein any of said agents is administered orally or parenterally.

* * * * *

UNITED STATES PATENT AND TRADEMARK OFFICE
CERTIFICATE OF CORRECTION

PATENT NO. : 4,935,450

DATED : June 19, 1990

INVENTOR(S) : Clarence D. CONE, Jr.

It is certified that error appears in the above-identified patent and that said Letters Patent is hereby corrected as shown below:

On the title page, item [54] and in column 1, lines 1 and 2:

Correct the title of the invention to read -- CONE CANCER THERAPY SYSTEM FOR EFFECTING ONCOLYSIS OF MALIGNANT NEOPLASMS --.

Signed and Sealed this

Third Day of September, 1991

Attest:

HARRY F. MANBECK, JR.

*Attesting Officer*

*Commissioner of Patents and Trademarks*